(12) United States Patent
Yamauchi et al.

(10) Patent No.: US 6,258,811 B1
(45) Date of Patent: Jul. 10, 2001

(54) METHODS FOR PREVENTING, INHIBITING OR TREATING GRAFT REJECTION REACTIONS IN GRAFT-VERSUS-HOST DISEASE (GVHD) AND ORGAN TRANSPLANTATION

(75) Inventors: Toshihiko Yamauchi; Akira Ishibashi; Naoki Tokuhara; Mitsuo Nagai, all of Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/269,924

(22) PCT Filed: Oct. 2, 1997

(86) PCT No.: PCT/JP97/03529

§ 371 Date: Apr. 2, 1999

§ 102(e) Date: Apr. 2, 1999

(87) PCT Pub. No.: WO98/14214

PCT Pub. Date: Apr. 9, 1998

(30) Foreign Application Priority Data

| Oct. 3, 1996 | (JP) | 8-262629 |
| Sep. 11, 1997 | (JP) | 9-246427 |

(51) Int. Cl.$^7$ ................................................ A61K 31/50
(52) U.S. Cl. ............................................................ 514/249
(58) Field of Search ............................................. 514/249

(56) References Cited

U.S. PATENT DOCUMENTS

| 4,703,110 | 10/1987 | Shudo | 534/566 |
| 5,037,825 | 8/1991 | Klaus et al. | 514/233.8 |
| 5,977,108 | * 11/1999 | Kikuchi et al. | 514/495 |

FOREIGN PATENT DOCUMENTS

| 0 284 288 | 9/1988 | (EP) . |
| 0 329 333 | 6/1989 | (EP) . |
| 0 440 503 A1 | 8/1991 | (EP) . |
| 63-255277 | 10/1988 | (JP) . |
| 2-76862 | 3/1990 | (JP) . |
| 6-53684 | 7/1994 | (JP) . |
| 6-340641 | 12/1994 | (JP) . |
| 8-505359 | 11/1996 | (JP) . |
| WO 96/20913 | 7/1996 | (WO) . |
| WO 96/20914 | 7/1996 | (WO) . |
| WO97/02244 | 1/1997 | (WO) . |
| WO 97/13506 | 4/1997 | (WO) . |
| WO 97/34869 | 9/1997 | (WO) . |

OTHER PUBLICATIONS

Kuwabara et al FEBS 16511 Letters 378 (1996) 153–156 Novel Synthetic retinoic acid inhibits rat collagen arthritis and differentially affects serum immunoglobulin subclass levels.

Mangelsdorf et al The Retinoids 2$^{nd}$ ed 1994 pp 319–349 The Retinoid Receptors.

Graupner et al Biochemical and Biophysical Research Communications vol. 179, No. 3, 1991 pp 1554–1561 6'–Substituted Naphthalene–2–carboxylic acid analogs, a new class of retinoic acid etc.

Science, vol. 2, p. 756–758 (1983) Inflammation and Collagenase Production in Rats with Adjuvant Arthritis Reduced with 13 cis–Retinoic Acid.

Murphy et al Bone Marrow Transplantation vol. 18, No. 3, Sep. 1996 (Sep. 1996), pp. 641–642 XXXP000974473 "Successful Use of topical retinoic acid in severe dry eye dou to chronic graft–versus–host disease".

* cited by examiner

*Primary Examiner*—Theodore J. Criares
*Assistant Examiner*—Jennifer Kim
(74) *Attorney, Agent, or Firm*—Nixon & Vanderhye

(57) ABSTRACT

The present invention provides remedies for graft-versus-host disease (GVHD) and graft rejection reactions in organ transplantation which comprise retinoic acid receptor (RAR) agonists as an active ingredient. Main examples thereof include 9-(4-methoxy-2,3,6-trimethylphenyl)-7,8-dimethylnona-2,4,6,8-tetraen-1-oic acid, 4-[(E)-2-(5,6,7,8-tetrahydro-5,5,8,8-tetramethylnaphthalen-2-yl)propenyl]benzoic acid, 4-{2-[5-(4,7-dimethylbenzofuran-2-yl)pyrroyl]}benzoic acid, 4-{2-[5-(5-chloro-7-ethylbenzofuran-2-yl)pyrrolyl]}benzoic acid and 4-{2-[5-(4,7-dimethylbenzothiophen-2-yl)pyrrolyl]}benzoic acid.

7 Claims, 2 Drawing Sheets

METHODS FOR PREVENTING, INHIBITING OR TREATING GRAFT REJECTION REACTIONS IN GRAFT-VERSUS-HOST DISEASE (GVHD) AND ORGAN TRANSPLANTATION

BACKGROUND OF THE INVENTION

1. Field of the Invention

The present invention relates to methods for preventing, inhibiting or treating graft-versus-host disease (GVHD) and graft rejection reactions in organ transplantation.

2. Prior Art

In bone marrow transplantation or blood transfusion, or organ transplantation from a donor to a recipient having no histocompatibility with the donor, the donor's lymphocytes migrate into the recipient. If the recipient cannot reject the donor's lymphocytes, the donor's lymphocytes take and proliferate in the recipient's body. Then the lymphocytes attack tissues with the guidance of antigens carried exclusively by the recipient, thus inducing disorders.

In 1959, Mathe et al. reported for the first time graft-versus-host disease (GVHD) in a leukemic patient after having bone marrow transplantation. The major symptoms of GVHD include frequent fever, anthema, diarrhea, vomiturition, anorexia, abdominal pain and hepatopathy. GVHD breaks out in patients having non-autogenous myeloma cells and induces in some cases lethal diseases such as systemic erythroderma or hepatic insufficiency. When an immunodeficient patient has the transplantation of an organ which is rich in immunocompetent cells, there arises a high risk of the onset of graft-versus-host reactions. Therefore, it is an important problem to prevent and treat GVHD in infants or children who suffer from primary immunodeficiency and are going to have bone marrow transplantation for reconstructing the immune system or patients who are going to have bone marrow transplantation for treating malignant diseases.

Bone marrow transplantation is a therapeutic which comprises breaking a host's hemic system and transplanting the bone marrow, i.e., a mass of cells serving as the basis of the hemic system of a healthy donor to the host so as to reconstruct in the host's body a hemic system originating in the donor. Essential factors for the success in marrow transplantation include the take of a graft, the regulation of graft-versus-host reactions and the immunological reconstruction. About one week after the bone marrow transplantation, the leukocyte count of the host attains the minimum level and thus the host is liable to suffer from bacterial or fungal infection. Acute GVHD frequently breaks out at this stage. To prevent GVHD, it is a practice to give an immunosuppressant cyclosporin A (CsA) optionally together with, for a short period of time, methotrexate (MTX). At the onset of acute GVHD, prednisolone and cyclosporin A are administered. The treatment of acute GVHD with the use of these drugs is restricted due to the side effects thereof, for example, hypertension, renal function disorder and an increase in the recurrence rate of leukemia. Namely, it is believed that cyclosporin A relates to the onset of nephrotoxicity, bone marrow depression, hypertension, hemolytic-uremic syndrome, hyperglycemia, shock, hypomagnesemia, and, in particular, atherosclerosis in heart transplantation. Also, it is known that prednisolone relates to induced infectious diseases, peptic ulcer, etc., while methotrexate relates to bone marrow depression, hepatic/renal function disorder, mucosal disorder, psychoneurosis, interstitial pneumonia, pulmonary fibrosis, etc.

On the other hand, chronic GVHD breaks out 70 to 400 days after transplantation. It is classified into three types of 1) progressive onset following acute GVHD, 2) quiescent occurring once acute GVHD disappears, and 3) de novo newly occurring without the onset of acute GVHD. Compared with acute GVHD, chronic GVHD causes organ derangement over a broad range and thus induces the appearance of autoantibodies in many cases. Although it has been a practice to administer cyclosporin A and prednisolone to treat chronic GVHD, which is known to be observed in 30 to 60% of patients with bone marrow transplantation, no satisfactory effect can be achieved thereby.

Under these circumstances, it has been urgently required to develop remedies for GVHD which are highly efficacious against acute GVHD and chronic GVHD and have a high safety.

The first case of organ transplantation was renal transplantation effected in 1950's. About 30 renal transplantations were performed in USA, France, etc. till 1960. In those days, exposure of patients to radiation was the only method for inhibiting the graft rejection reactions (immune suppression). Thus, the rejection reactions could not be controlled well, which made it impossible to successfully perform the transplantation. The only successful case of renal transplantation was one effected between identical twins where no rejection reaction arose. Subsequently there have been developed immunosuppressants such as azathioprine, prednisolone, cyclosporin A, methotrexate and tacrolimus (FK 506): Inorgan transplantation, in particular, the appearance of cyclosporin A results in a remarkable increase in the ratio of successful transplantations. However, the long-term administration of the immunosuppressants brings about various side effects and complications, which makes the postoperative QOL not always favorable. It is reported that the side effects of azathioprine include bone marrow depression, hepatic disorder, pancreatitis, digestive tract symptoms, cardiopalmus and respiratory disorder, while those of tacrolimus (FK 506) include renal function disorder, shock, elevation of blood pressure, heart failure, pancreatitis, hemolytic-uremic syndrome, thrombotic thrombopenia, purpura and hyperglycemia. Also, prednisolone, cyclosporin A and methotrexate exhibit similar side effects as those described above.

Retinoic acid plays important roles in the growth and retention of functions in animals, for example, specifically regulating the differentiation and proliferation of cells and participating in the morphogenesis of vertebrates. Concerning these physiological functions, retinoic acid has attracted public attention as a carcinostatic or a specific remedy for proliferative skin diseases (psoriasis, keratosis, etc.). Thus, there have been synthesized a number of retinoic acid analogs. Recently, there has been pointed out the presence of more than one retinoic acid receptor subtype, though the physiological meaning thereof has never been clarified so far (The Retinoids, 2nd ed., Raven Press, Ltd., New York, 1994, Sporn, M. B., Roberts, A. B., Goodman, D. S.).

On the other hand, it has been known for a long time that vitamin A closely relates to the immune system. It has been frequently reported that retinoic acid, which is an oxidative metabolite of vitamin A, would exert a suppressive effect on the immune system. For example, Brinckerhoff et al. reported that secondary inflammation in rat adjuvant arthritis was significantly suppressed by administering 13-cis-retinoic acid (Science 221, 756, 1983.). Recently, Kuwabara et al. reported that rat collagen arthritis was significantly ameliorated and the blood anticollagen antibody titer was lowered by administering retinoic acid receptor-α agonists (FEBS Letters, 378, 153, 1996.).

It has been disclosed hitherto that retinoic acid receptor agonists are usable in treating cancers such as leukemia, mammary cancer, prostatic cancer, lung cancer, esophageal and respiratory tract cancer, skin cancer and bladder cancer, skin diseases such as psoriasis, keratosis, eczema, atopic dermatitis, acne and Darier's disease, autoimmune diseases such as rheumatoid arthritis and lupus erythematosus, inflammations in organs over a broad range such as chronic polyarthritis, spondylathritis and arthrosis deformans, and allergic or rheumatic immunological diseases, in U.S. Pat. No. 4,703,110, JP-A-2-76862, JP-A-63-255277, JP-A-8-505359, etc. However, there has been no report suggesting that retinoic acid receptor agonists are applicable to GVHD in bone marrow transplantation or retinoic acid receptor agonists inhibit graft rejection reactions in organ transplantation.

DISCLOSURE OF THE INVENTION

Under these circumstances, the present inventors have conducted extensive studies on the immunosuppressive effects of retinoic acid receptor (RAR) agonists. As a result, they have found out that retinoic acid receptor (RAR) agonists as will be shown hereinbelow, in particular, RARα agonists have GVHD inhibitory effects and inhibit graft rejection reactions in organ plantation, thus completing the present invention.

Accordingly, the present invention relates to methods for preventing, inhibiting or treating graft-versus-host disease or graft rejection reactions in organ transplantation by administering an efficacious amount of retinoic acid receptor (RAR) agonists to patients.

The present invention further relates to the use of retinoic acid receptor (RAR) agonists in the production of drugs for preventing, inhibiting or treating graft-versus-host disease or graft rejection reactions in organ transplantation.

The present invention furthermore relates to drugs for preventing, inhibiting or treating graft-versus-host disease or graft rejection reactions in organ transplantation which contain retinoic acid receptor (RAR) agonists as an active ingredient.

1) Fused-ring carboxylic acid derivatives represented by the following formula (I):

$$\boxed{L\ M}-\boxed{A}-\boxed{B}-D$$

wherein the rings L and M, which have been fused, are the same as or different from each other and represents an optionally substituted aromatic hydrocarbon ring or an optionally substituted heterocycle; the rings A and B independently represent each an optionally substituted aromatic hydrocarbon ring or a heterocycle; and D represents optionally protected carboxy.

2) Heterocyclic carboxylic acid derivatives represented by the following formula (II):

$$A-B-(D)_{n1}-\overset{O}{\underset{\|}{C}}-M$$

wherein A represents a group represented by the following formula:

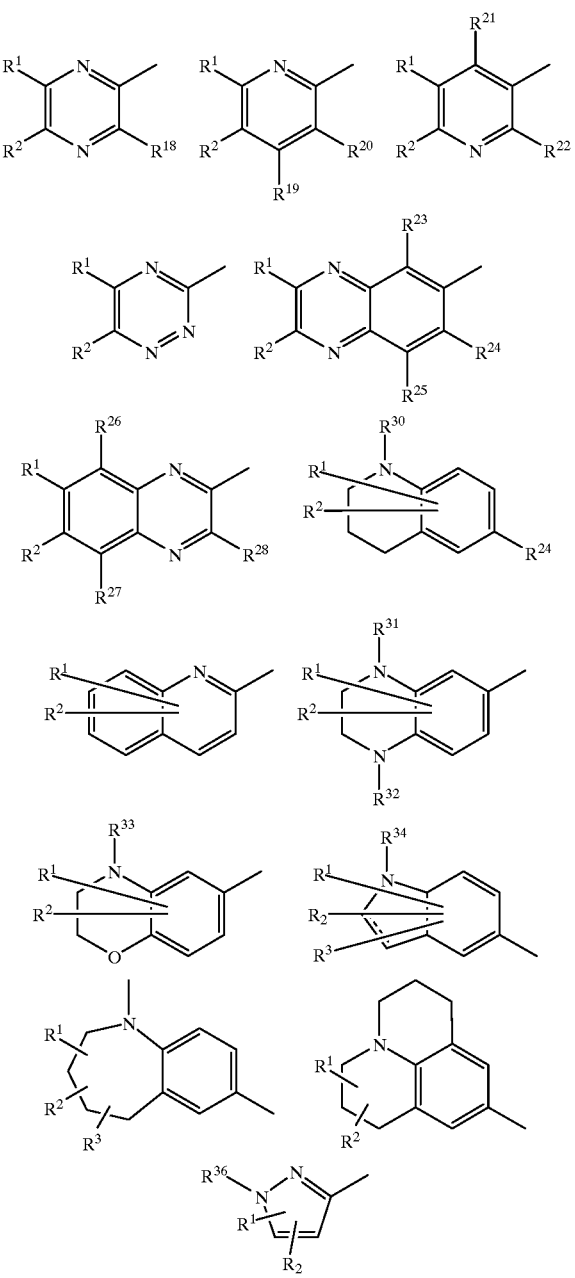

wherein $R^1$ to $R^3$, $R^{18}$ to $R^{28}$ and $R^{30}$ to $R^{36}$ are the same as or different from each other and represent hydrogen, halogeno, a lower alkyl or an optionally substituted phenyl; and ═══ represents either a single bond or a double bond;

B represents an optionally substituted heteroarylene, an optionally substituted arylene, a group represented by the formula —CONH— or a group represented by the formula —CR$^6$═CR$^7$— (wherein R$^6$ and R$^7$ are the same as or different from each other and represent hydrogen, lower alkyl or halogeno);

D represents an optionally substituted arylene, an optionally substituted heteroarylene or a group represented by the formula —CR$^6$═CR$^7$— (wherein R$^6$ and R$^7$ are each as defined above);

n, represents 0 or 1; and

M represents hydroxy, lower alkoxy or a group represented by the formula —NR$^{16}$R$^{17}$ (wherein R$^{16}$ and R$^{17}$ are the same as or different from each other and represent hydrogen, hydroxy, lower alkyl, hydroxyalkyl, aryl or heteroaryl, or R$^{16}$ and R$^{17}$ may form a ring with the nitrogen atom to which they are bonded, and the ring may contain oxygen or sulfur.

3) 4-[(5,6,7,8-Tetrahydro-5,5,8,8-tetramethylnaphthalen-2-yl)pyrrolyl]benzoic acid, 4-[(5,6,7,8-tetrahydro-5,5,8,8-tetramethylnaphthalen-2-yl)furanyl]benzoic acid, 4-[(5,6,7,8-tetrahydro-5,5,8,8-tetramethylnaphthalen-2-yl)thiophenyl]benzoic acid and 4-[(5,6,7,8-tetrahydro-5,5,8,8-tetramethylnaphthalen-2-yl)pyrazolyl]benzoic acid disclosed in JP-A 2-240058.

4) 3,4-Dihydro-2H-1-benzopyranylpropenylbenzic acid derivatives, 3,4-dihydro-2H-1-benzothiopyranylpropenybenzoic acid derivatives, 1,2,3,4-tetrahydroquinolinylpropenylbenzoic acid derivatives, (3,4-dihydro-2H-1-benzopyrancarboxamido)benzoic acid derivatives, (3,4-dihydro-2H-1-benzothiopyrancarboxamido)benzoic acid derivatives and (1,2,3,4-tetrahydroquinolinecarboxamido)benzoic acid derivatives disclosed in JP-A 2-76862.

5) 3,4-Dihydro-2H-1-benzopyranylacetylene derivatives, 3,4-dihydro-2H-1-benzothiopyranylacetylene derivatives and 1,2,3,4-tetrahydroquinolinylacetylene derivatives disclosed in JP-A 63-255277.

6) Tetrahydronaphthylpropenylphenol derivatives disclosed in JP-A 62-267245.

7) Phenylpolyene derivatives disclosed in JP-A 49-126637.

8) All-trans-retinoic acid.

Preferable examples of the compounds according to the present invention include all-trans-retinoic acid and the compounds represented by the following formulae:

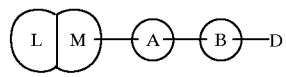

wherein L, M, A, B and D are each as defined above; and

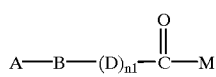

wherein A, B, D, M and n$_1$ are each as defined above.

Still preferable examples of the compounds of the present invention are as follows.

1) 4-{2-[5-(5,8-Dimethylnaphthalen-2-yl)pyrrolyl]}benzoic acid.
2) 4-{2-[5-(8-Methylnaphthalen-2-yl)pyrrolyl]}benzoic acid.
3) 4-{2-[5-(8-Ethylnaphthalen-2-yl)pyrrolyl]}benzoic acid.
4) 4-{2-[5-(8-Isopropylnaphthalen-2-yl)pryyolyl]}benzoic acid.
5) 4-{2-[5-(8-Naphthalen-2-yl)pyrrolyl]}benzoic acid.
6) 4-{2-[5-(8-Phenylnaphthalen-2-yl)pyrrolyl]}benzoic acid.
7) 4-{2-[5-(4,7-Dimethylbenzofuran-2-yl)pyrrolyl]}benzoic acid.
8) 4-{2-[5-(4,7-Dichlorobenzofuran-2-yl)pyrrolyl]}benzoic acid.
9) 4-{2-[5-(5-Chloro-7-ethyl benzofuran-2-yl)pyrrolyl]}benzoic acid.
10) 4-{2-[5-(4,7-Dimethylbenzothiophen-2-yl))pyrrolyl]}benzoic acid.
11) 4-{2-[5-(3-Fluroro-4,7-dimethylbenzofuran-2-yl)pyrrolyl]}benzoic acid.
12) 4-{2-[5-(7-Ethyl-4-methylbenzofuran-2-yl)pyrrolyl]}benzoic acid.
13) 4-{2-[5-(7-Fluoro-4-trifluoromethylbenzofuran-2-yl)pyrrolyl]}benzoic acid.
14) All-trans-retinoic acid.

The term "optionally substituted" as used herein means optionally having substituent(s) selected from among, for example, hydroxy; thiol; nitro; cyano; halogeno such as fluorine, chlorine, bromine and iodine; lower alkyl such as methyl, ethyl, n-propyl and isopropyl; lower alkoxy such as methoxy, ethoxy, n-propoxy, isopropoxy and butoxy; haloalkyl such as fluoromethyl, difluoromethyl, trifluoromethyl and 2,2,2-trifluoroethyl; alkylthio such as methylthio, ethylthio and isopropylthio; acyl such as acetyl, propionyl and benzoyl; hydroxyalkyl such as hydroxymethyl, hydroxyethyl and hydroxypropyl; amino; monoalkylamino such as methylamino, ethylamino and isopropylamino; dialkylamino such as dimethylamino and diethylamino; carboxy; alkoxycarbonyl such as methoxycarbonyl, ethoxycarbonyl and propoxycarbonyl; carbamoyl; alkylcarbamoyl such as methylcarbamoyl and dimethylcarbamoyl; acylamino such as acetylamino and benzoylamino; sulfamoyl; alkylsulfonyl such as methylsulfonyl and ethylsulfonyl; optionally substituted arylsulfonyl such as benzenesulfonyl and p-toluenesulfonyl; optionally substituted aryl such as phenyl, tolyl and anisolyl; optionally substituted heteroaryl such as pyrrol, pyrazolyl, imidazolyl, triazolyl, tetrazolyl, thiazolyl, pyridyl, pyrimidyl and pyradinyl; carboxyalkyl; alkyloxycarbonylalkyl such as methoxycarbonylmethyl, ethoxycarbonylmethyl and methoxycarbonylethyl; carboxyalkoxy such as carboxymethoxy; arylalkyl such as benzyl and 4-chlorobenzyl; heteroarylalkyl such as pyridylmethyl and pyridylethyl; and alkylenedioxy such as methylenedioxy and ethylenedioxy.

The term "aromatic hydrocarbon" means benzene, naphthalene, anthracene, etc.

The term "heterocycle" means groups derived from a monocycle containing one to three heteroatoms of at least one type selected from the group consisting of sulfur, oxygen and nitrogen atoms. Examples thereof include pyrrole, thiophene, furan, thiazole, oxazole, isothiazole, isoxazole, imidazole, pyrazole, thiadiazole, oxadiazole, triazole, pyridine, pyridazine, pyrimidine and pyrazine rings.

The term "halogeno" means fluorine, chlorine, bromine and iodine.

The term "lower alkyl" means linear or branched $C_{1-6}$ alkyl such as methyl, ethyl, n-propyl, n-butyl, isopropyl, isobutyl and n-hexyl.

The term "heteroarylene" means the heterocycle as cited above having two bonds directed outwards.

The term "arylene" means the aromatic hydrocarbon as cited above having two bonds directed outwards.

The compounds represented by the formula (I) can be readily obtained by using methods commonly employed or combining these methods. Next, an example thereof will be described.

The compounds wherein the ring A is a pyrrole ring can be obtained by the following method.

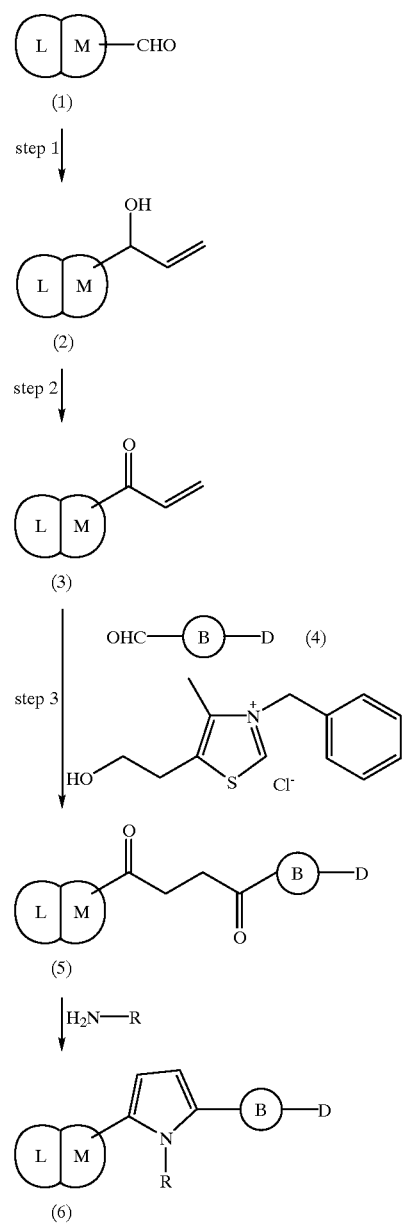

(Step 1)

An aldehyde (1) is reacted with an organometallic reagent in a conventional manner to give an allyl alcohol (2).

Examples of the organometallic reagent include Grignard reagents, organolithium reagents, organozinc reagents and organocopper complexes. As the reaction solvent, use may be made of an arbitrary one so long as it remains inert during the reaction. Examples thereof include etheric solvents such as ether and tetrahydrofuran. The reaction temperature may range from about −78° C. to the boiling point of the solvent, preferably from −78° C. to 20° C.

(Step 2)

In this step, the allyl alcohol (2) obtained in the step 1 is oxidized in a conventional manner to give a vinyl ketone (3).

Although the oxidation may be effected by any conventional method, it is preferable to select a method with the use of an appropriate oxidizing agent. As the oxidizing agent, use may be made of activated manganese dioxide, pyridinium chlorochromate, pyridinium dichromate, Dess- Martin reagent, Swern oxidizing agent, etc. As the reaction solvent, use may be made of an arbitrary organic solvent so long as it remains inert during the reaction. Preferable examples thereof include dichloromethane, chloroform and acetone. The reaction temperature may range from about −78° C. to the boiling point of the solvent, preferably from −78° C. to 20° C.

(Step 3)

In this step, the vinyl ketone (3) and aldehyde (4) obtained in the step 2 are treated by the method of Stetter 5 described in Org. Synth. 65, 26 to give a diketone represented by the formula (5).

Preferable results can be obtained by using a thiazolium salt catalyst in this reaction. In this step, it is preferable to use triethylamine, sodium acetate, etc. as a base. As the reaction solvent, use may be made of methanol, ethanol, N,N-dimethylformamide, etc. The reaction temperature may range from about 60° C. to the boiling point of the solvent.

(Step 4)

In this step, the diketone (5) obtained in the step 3 is treated by a method commonly employed to give a pyrrole compound represented by the formula (6).

The target compound (6) can be obtained by reacting the compound (5) with, for example, an ammonium salt such as ammonium acetate or a primary amine. In this step, use may be made of an alcoholic solvent such as methanol or ethanol, acetic acid, etc. as the reaction solvent. The reaction temperature may range from about 70° C. to the boiling point of the solvent.

The pyrrole compound (6) obtained in the step 4 is hydrolyzed in a conventional manner to give a carboxylic acid. In this step, preferable results can be obtained by using a base. Preferable results can be obtained by using as the base an aqueous solution of lithium hydroxide, sodium hydroxide, potassium hydroxide, etc. As the reaction solvent, use may be preferably made of an alcoholic solvent such as methanol or ethanol, or an etheric solvent such as tetrahydrofuran. The reaction temperature may preferably range from about 20° C. to the boiling point of the solvent.

Processes for producing other compounds are disclosed in JP-A 9-71566, JP-A 2-240058, JP-A 2-76862 and JP-A 63-255277.

The fact that the compounds represented by the formula (I) are retinoic acid receptor (RAR) agonists has been proved by performing a retinoic acid receptor (RAR) binding assay and recognizing the RAR-mediated transcriptional promotion activity. The compounds represented by the formula (II) are described in JP-A 9-71566. Some parts of other compounds are described in The Retinoids, 2nd ed., 85–88 as cited above, G. Graupner, G. Malle et al.; Biochemical and Biophysical Research Communications, 179, 1554–1561 (1991), etc.

Mode for Carrying Out the Invention:

The compounds of the present invention are administered either orally or parenterally. The compounds according to the present invention can be administered in the forms of tablets, dusts, granules, capsules, syrups, troches, suppositories, injections including drips, ointments, nasal drops, cataplasmas, lotions, etc.

The administration dose thereof is not particularly restricted and varies depending on the severity of the symptoms, the age, sex, body weight and sensitivity of the patient, administration method, administration time, dosage schedule, the properties of the medicinal preparation and the active ingredient. In usual, about 1 to 2000 mg/day, preferably 1 to 1000 mg/day, of a compound is administered to an adult. It is a practice to administer the compound in one to several portions per day. In the case of an injection, the daily dose thereof usually ranges from about 1 to 1000 µg/kg, preferably 1 to 300 µg/kg.

EXAMPLES

To illustrate the effects of the present invention, the following Examples will be given, though the present invention is not restricted to these compounds.

A graft-versus-host disease (GVHD) model experiment was effected in accordance with the method reported by Durei et al. (J. Clin. Invest., 94, 1333 1994.).

As the indication of an acute GVHD model (1), use was made of the cytotoxic T cell activity of a donor on a host. As the indication of a chronic GVHD model (2), use was made of the blood antiDNA antibody titer.

Example 1

Acute GVHD Model:

In the transplantation, BDF1 mice (H-2b/d) and C57BL/6N mice (H-2b) were employed respectively as the hosts and donors. 5×10⁷/mouse of donors' spleen cells were transferred into the hosts via the tail vein. 4-{2-[5-(4,7-Dimethylbenzofuran-2-yl)pyrrolyl]}benzoic acid (compound A) was suspended in a 0.5% aqueous solution of methylcellulose and then orally administered to the hosts once a day from the first day of the cell transfer to the day before the measurement of the cytotoxic T cell activity. The 0.5% aqueous solution of methylcellulose alone was similarly administered to the control group. 12 to 13 days after the cell transfer, the spleen of each host animal was taken out and a suspension of the spleen cells to be used as effector cells was prepared. As the target cells, use was made of P-815(H-2d) which were cultured together with the effector cells for 4 hours. The cytotoxicity (%) was expressed as the percentage of $^{51}$Cr liberated into the culture supernatant during this culture time to the total radioactivity.

Figure 1:
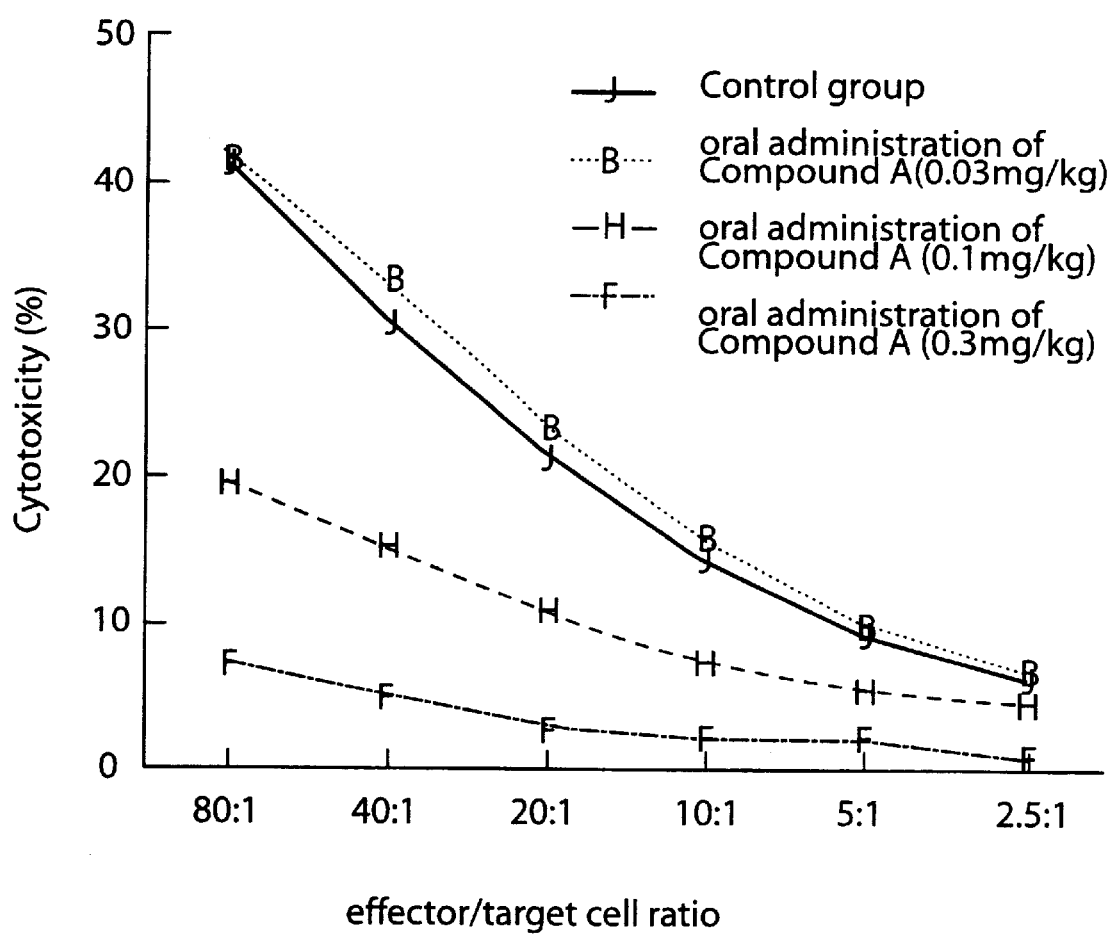
FIG. 1 shows the effect of the compound A on acute GVHD.

FIG. 1 shows the results.

Thus, 4-{2-[5-(4,7-dimethylbenzofuran-2-yl)pyrrolyl]}benzoic acid (compound A) strongly inhibited the induction of the cytotoxic T cell activity dose-dependently from 0.1 mg/kg.

Example 2

Chronic GVHD:

In the transplantation, BDF1 mice (H-2b/d) and DBA/2 mice (H-2d) were employed respectively as the hosts and donors. 5×10⁷/mouse of donors' spleen cells were transferred into the hosts via the tail vein. 4-{2-[5-(4,7-Dimethylbenzofuran-2-yl)pyrrolyl]}benzoic acid was dissolved in a 0.5% aqueous solution of methylcellulose and then orally administered to the hosts once a day from the first day of the cell transfer to the day before the blood sampling. The 0.5% aqueous solution of methylcellulose alone was similarly administered to the control group. Two weeks after the cell transfer, the blood of each host animal was sampled and the serum antiDNA antibody titer (IgG class) was measured by the ELISA method.

Figure 2:
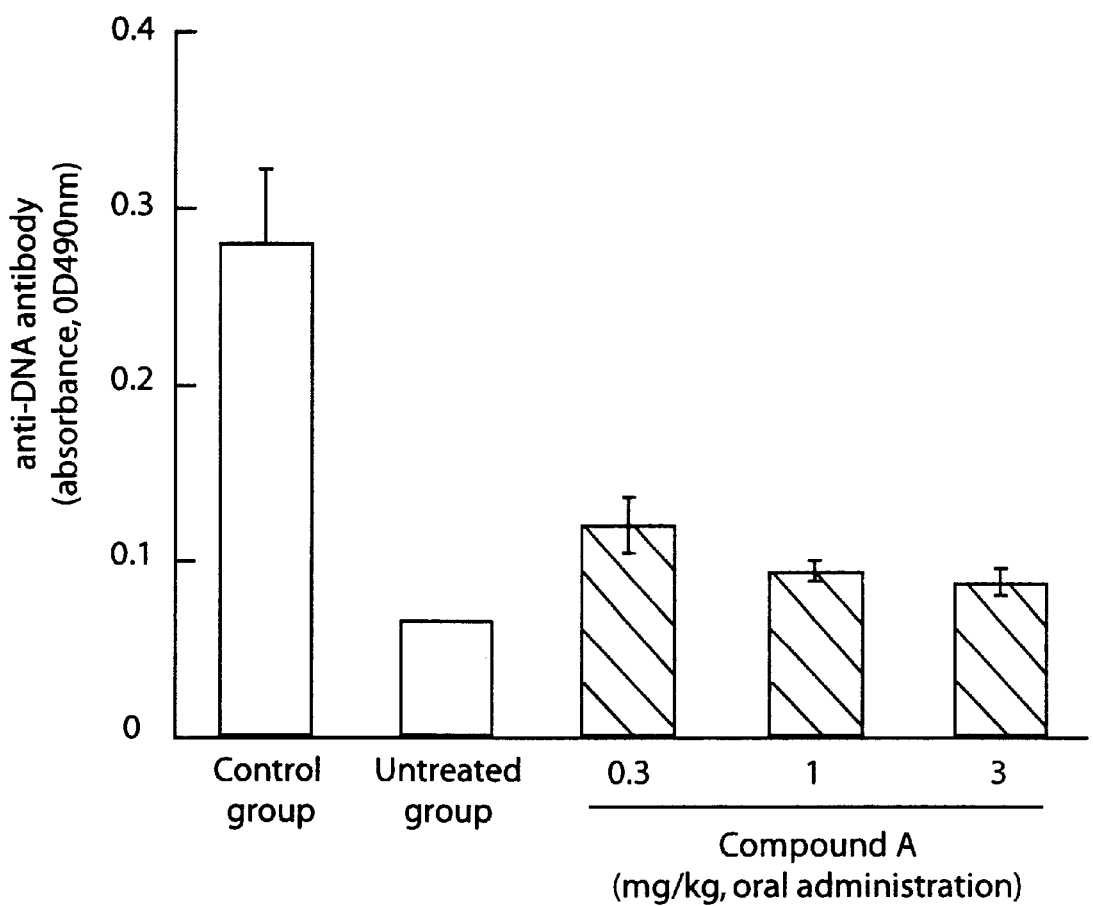
FIG. 2 shows the effect of the compound A on chronic GVHD.

FIG. 2 shows the results.

Thus, 4-{2-[5-(4,7-dimethylbenzofuran-2-yl)pyrrolyl]}benzoic acid strongly inhibited the serum antiDNA antibody titer dose-dependently from 0.3 mg/kg.

Referential Example 1

Retinoic acid receptor (RAR) binding assay and RAR-mediated transcriptional promotion activity of compound represented by formula (I):

TABLE 1

| | Receptor binding assay | | |
|---|---|---|---|
| | Receptor binding assay IC$_{50}$ (nM) | | |
| Compound | RAR-α | RAR-β | RAR-γ |
| [structure: 4,7-dimethylbenzofuran-pyrrolyl-benzoic acid] | 1.4 | 340 | >>500 |
| [structure: 4,7-dichlorobenzofuran-pyrrolyl-benzoic acid] | 1.0 | 500 | >>500 |

TABLE 1-continued

Receptor binding assay

| Compound | Receptor binding assay IC$_{50}$ (nM) | | |
|---|---|---|---|
| | RAR-α | RAR-β | RAR-γ |
| 7-Cl, 4-F-benzofuran-pyrrole-C$_6$H$_4$-CO$_2$H | 3.8 | >500 | >>500 |
| 7-F, 4-CF$_3$-benzofuran-pyrrole-C$_6$H$_4$-CO$_2$H | 0.6 | 107 | 195 |
| 4,7-dimethyl-3-F-benzofuran-pyrrole-C$_6$H$_4$-CO$_2$H | <0.5 | 49 | 225 |
| 7-ethyl-4-methyl-benzofuran-pyrrole-C$_6$H$_4$-CO$_2$H | <0.5 | 160 | 270 |
| 5,5,8,8-tetramethyl-tetrahydroquinoxaline-pyrrole-C$_6$H$_4$-CO$_2$H | 0.6 | 56 | 140 |

TABLE 2
Transcriptional promotion activity
| Compound | Transcriptional promotion activity Relative ED30* | | |
|---|---|---|---|
| | RAR-α | RAR-β | RAR-γ |
| 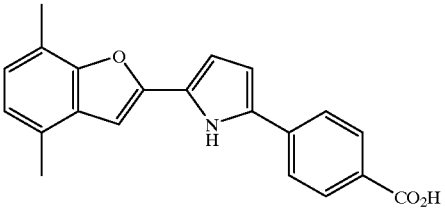 | 0.4 | 13 | 191 |
| 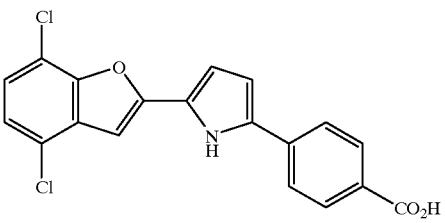 | 1.0 | 160 | 1400 |
| 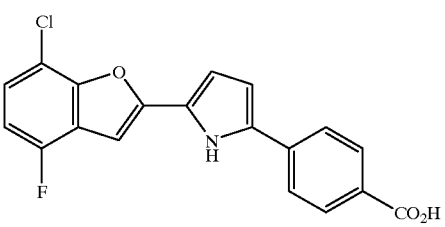 | 0.33 | 91 | 790 |
| 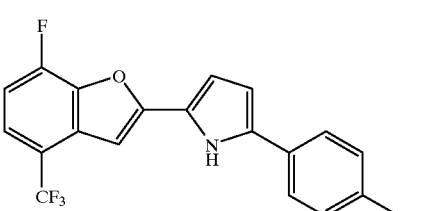 | 0.33 | 8.1 | 95 |
| 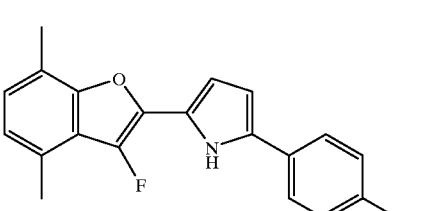 | 0.39 | 2.8 | 31 |
| 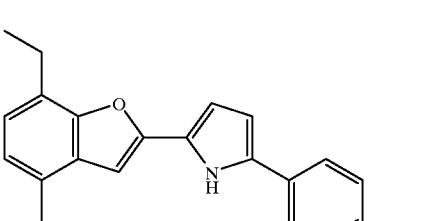 | 0.26 | 24 | 120 |

TABLE 2-continued

Transcriptional promotion activity

| Compound | Transcriptional promotion activity Relative ED30* | | |
|---|---|---|---|
| | RAR-α | RAR-β | RAR-γ |
| [structure: 5,5,8,8-tetramethyl-5,6,7,8-tetrahydroquinoxaline linked to pyrrole linked to phenyl-CO₂H] | 0.21 | 1.4 | 19 |

*Relative $ED_{30}$:

First, the transcriptional activity induced by 3 μM of all-trans-retinoic acid was taken as 100% and the concentration showing 30% activity ($ED_{30}$) of each compound was calculated. Specific $ED_{30}$ of each receptor was determined by taking the $ED_{30}$ of all-trans-retinoic acid as 1.

The results clearly indicate that these compounds are retinoic acid receptor (RAR) agonists showing a particularly high selectivity for the subtype α.

Next, Synthesis Examples of the compounds represented by the general formula (I) will be given, though the compounds of the present invention are not restricted thereto.

Synthesis Example 1
4-{2-[5-(5,8-Dimethylnaphthalen-2-yl)prrolyl]}benzoic Acid (A) 2-Acryloyl-5,8-dimethylnaphthalene In a nitrogen atmosphere, of 5,8-dimethyltetralone (25 g) was dissolved in methanol (200 ml) and sodium borohydride (3.0 g) was added to the mixture at 0° C. After stirring at 0° C. for 30 min, a saturated aqueous solution of ammonium chloride and water were successively added to the mixture. The resulting precipitate was collected by filtration, washed with water and dried to give an alcohol (23.7 g). In a nitrogen atmosphere, the alcohol (23.7 g) was dissolved in N,N-dimethylformamide (60 ml) and phosphorus oxychloride (25 ml) was added dropwise to the mixture at 0° C. After the completion of the addition, the reaction mixture was heated under stirring at 100° C. for 2 hr. Then it was cooled to room temperature by allowing to stand. Next, ice-water and sodium acetate (9 g) were added thereto followed by extraction with hexane (200 ml×4). The organic layers were combined, washed with brine and dried over anhydrous magnesium sulfate. After filtering, the filtrate was concentrated to give an aldehyde (21.3 g) as a crude product.

In a nitrogen atmosphere, the obtained aldehyde (20.9 g) was dissolved in dioxane (300 ml). After adding dichlorodicyanobenzoquinone (50.9 g), the resultant mixture was heated under ref lux for 1.5 hr. Then, it was cooled to room temperature by allowing to stand followed by the addition of toluene (500 ml). The resulting precipitate was collected by filtration and washed with toluene several times. The filtrate was concentrated and the resulting crude product was purified by silica gel column chromatography to give 5,8-dimethyl-2-naphtaldehyde (10.3 g) as colorless crystals.

$^{1}$H-NMR (CDCl$_3$, 400 MHz) δ; 2.69 (s, 3H), 2.76(s, 3H), 7.31 (d, 1H, J=7.2 Hz), 7.37 (d, 1H, J=7.2 Hz), 7.99 (dd, 1H, J=1.6, 8.8 Hz), 8.11 (d, 1H, J=8.4 Hz), 8.51 (d, 1H, J=1.6 Hz), 10.2 (s, 1H)

5,8-Dimethyl-2-naphthaldehyde (3.7 g) was dissolved in ether (80 ml). Then a 1.0 M solution (30 ml) of vinylmagnesium bromide in tetrahydrofuran was added to the mixture at −78° C. and the resultant mixture was slowly heated to −30° C. After quenching with a saturated aqueous solution of ammonium chloride, the mixture was extracted with ethyl acetate (100 ml×2). The organic layers were combined, washed with brine and dried over anhydrous magnesium sulfate. After filtering, the filtrate was concentrated to give allyl alcohol (5.0 g) as a crude product.

Then the allyl alcohol was dissolved in dichloromethane (30 ml). After adding activated manganese dioxide (30 g), the resultant mixture was stirred at room temperature for 40 hr. Then it was filtered through celite and the filtrate was concentrated. The resulting product was purified by silica gel column chromatography to give the title compound (1.8 g). At the same time, 1.2 g of the starting material was recovered.

$^{1}$H-NMR (CDCl$_3$, 400 MHz) δ; 2.68(s, 3H), 2.74(s, 3H), 6.00 (dd, 1H, J=1.6, 10.4 Hz), 6.50(dd, 1H, J=1.6, 17.2 Hz), 7.27–7.39 (m, 3H), 8.06–8.10 (m, 2H), 8.64 (s, 1H)

(B) Methyl 4-[4-(5,8-dimethylnaphthalen-2-yl)-4-oxobutanoyl]benzoate (Process 1)

A mixture comprising 2-acryloyl-5,8-dimethylnaphthalene (1.8 g), methyl terephthalaldehydate (1.4 g), sodium acetate (0.23 g), 3-benzyl-5-(2-hydroxymethyl)-4-methylthiazolium chloride (0.23 g) and ethanol (100 ml) was heated under reflux for 10 hr. The resulting crystals were filtered, washed with ethanol and then dried to give the title compound (1.26 g) as colorless crystals.

(Process 2)

A mixture comprising 5,8-dimethyl-2-naphthaldehyde (1.0 g), methyl 4-acryloylbenzoate (1.2 g), 3-benzyl-5-(2-hydroxymethyl)-4-methylthiazolium chloride (0.28 g), triethylamine (0.88 ml) and N,N-dimethylformamide (20 ml) was heated under stirring at 70° C. for 3 hr. After cooling to room temperature by allowing to stand, water was added to the reaction mixture followed by extraction with ethyl acetate (20 ml×3). The organic layers were combined, washed with brine and dried over anhydrous magnesium sulfate. After filtering, the filtrate was concentrated and the resulting crude crystals were washed with a solvent mixture of n-hexane and ethyl acetate to give the title compound (0.82 g) as colorless crystals.

$^{1}$H-NMR (CDCl$_3$, 400 MHz) δ; 2.68 (s, H), 2.75 (s, 3H), 3.54 (t, 2H, J=6.4 Hz), 3.66 (t, 2H, J=6.4 Hz), 3.96 (s, 3H), 7.28 (d, 1H, J=7.2 Hz), 7.33 (d, 1H, J=7.2 Hz), 8.06–8.18 (m, 6H), 8.75 (d, 1H, J=1.6 Hz)

(C) Methyl 4-{2-[5-(5,8-dimethylnaphthalen-2-yl)pyrrolyl]} benzoate

A mixture of methyl 4-[4-(5,8-dimethylnaphthalen-2-yl)-4-oxobutanoyl]benzoate (0.5 g), ammonium acetate (2.0 g) and methanol (20 ml) was heated under reflux for 5 hr. After cooling to room temperature by allowing to stand, yellow crystals were collected by filtration, washed with methanol and dried to give a methyl ester (0.47 g) as yellow crystals.

$^1$H-NMR (CDCl$_3$, 400 MHz) δ; 2.67 (s, 3H), 2.73 (s, 3H), 3.93 (s, 3H), 6.76 (m, 2H), 7.18 (d, 1H, J=7.1 Hz), 7.23 (d, 1H, J=7.1 Hz), 7.63 (d, 2H, J=8.6 Hz), 7.74 (dd, 1H, J=1.6, 9.2 Hz), 8.03–8.09 (m, 4H), 8.84 (s, 1H)

(D) 4-{2-[5-(5,8-Dimethylnaphthalen-2-yl)pyrrolyl]} benzoic Acid

A mixture of the methyl ester (0.68 g), ethanol (40 ml) and a 5N aqueous solution of sodium hydroxide (4 ml) was heated under reflux for 1 hr. To the resulting pale yellow suspension was added water followed by dissolution. Next, a 6N hydrochloric acid (about 3.5 ml) and water (40 ml) were added thereto. The resulting crystals were collected by filtration, washed with water and dried to give the title compound (0.52 g) as yellow crystals.

$^1$H-NMR (DMSO-d$_6$, 400 MHz) δ; 2.59 (s, 3H), 2.69 (s, 3H), 6.81 (m, 2H), 7.16 (d, 1H, J=7.1 Hz), 7.22 (d, 1H, J=7.1 Hz), 7.87–8.00 (m, 6H), 8.36 (s, 1H), 11.6 (s, 1H)

Synthesis Example 2
4-{2-[5-(5,7-Dimethylnaphthalen-2-yl)pyrrolyl]}benzoic Acid (A) 2-Acryloyl-5,7-dimethylnaphthalene The title compound was obtained by the same procedure as the one of Synthesis Example 1 (A).

$^1$H-NMR (CDCl$_3$, 400 MHz) δ; 2.50 (s, 3H), 2.68 (s, 3H), 5.97 (dd, 1H, J=1.6, 10.8 Hz), 6.49 (dd, 1H, J=1.6, 17.2 Hz), 7.29 (s, 1H), 7.32 (dd, 1H, J=10.8, 17.2 Hz), 7.59 (s, 1H), 8.00 (m, 2H), 8.37 (s, 1H)

(B) Methyl 4-[4-(5,7-dimethylnaphthalen-2-yl)-4-oxobutanoyl]benzoate

The title compound was obtained by the same procedure as the one of Synthesis Example 1 (B) (Process 1).

$^1$H-NMR (CDCl$_3$, 400 MHz) δ; 2.51 (s, 3H), 2.6 (s, 3H), 3.53 (t, 2H, J=6.1 Hz), 3.63 (t, 2H, J=6.1 Hz), 3.96 (s, 3H), 7.30 (s, 1H), 7.61 (s, 1H), 8.01 (d, 1H, J=8.8 Hz), 8.03 (dd, 1H, J=1.6, 8.8 Hz), 8.12 (d, 2H, J=8.8 Hz), 8.15 (d, 2H, J=8.8 Hz), 8.48 (s, 1H)

(C) Methyl 4-{2-[5-(5,7-dimethylnaphthalen-2-yl)pyrrolyl]} benzoate

The title compound was obtained by the same procedure as the one of Synthesis Example 1 (C).

$^1$H-NMR (CDCl$_3$, 400 MHz) δ; 2.48 (s, 3H), 2.67 (s, 3H), 3.93 (s, 3H), 6.72–6.78 (m, 2H), 7.14 (s, 1H), 7.49 (s, 1H), 7.62 (d, 2H, J=8.4 Hz), 7.67 (dd, 1H, J=1.6, 8.8 Hz), 7.85 (d, 1H, J=1.6 Hz), 7.97 (d, 1H, J=8.8 Hz), 8.07 (d, 2H, J=8.4 Hz), 8.82 (s, 1H)

(D) 4-{2-[5-(5,7-Dimethylnaphthalen-2-yl)pyrrolyl]} benzoic Acid

The title compound was obtained by the same procedure as the one of Synthesis Example 1 (D).

$^1$H-NMR (DMSO-d$_6$, 400 MHz) δ; 2.42 (s, 3H), 2.60 (s, 3H), 6.79 (m, 2H) 7.13 (s, 1H), 7.48 (s, 1H), 7.84–7.94 (m, 6H), 8.21 (s, 1H), 11.5 (s, 1H)

Synthesis Example 3
4-{2-[5-(5,6,7,8-Tetramethylnaphthalen-2-yl)pyrrolyl]} benzoic Acid (A) 2-Acryloyl-5,6,7,8-tetramethylnaphthalene The title compound was obtained by the same procedure as the one of Synthesis Example 1 (A).

$^1$H-NMR (CDCl$_3$, 400 MHz) δ; 2.45 (s, 3H), 2.46 (s, 3H), 2.65 (s, 3H), 2.70 (s, 3H), 5.97 (dd, 1H, J=2.0, 10.8 Hz), 6.50 (dd, 1H, J=1.6, 17.2 Hz), 7.36 (dd, 1H, J=10.8, 17.2 Hz), 7.98 (dd, 1H, J=1.6, 8.8 Hz), 8.11 (d, 1H, J=8.8 Hz), 8.71 (d, 1H, J=1.6 Hz)

(B) Methyl 4-[4-(5,6,7,8-tetramethylnaphthalen-2-yl)-4-oxobutanoyl]benzoate

The title compound was obtained by the same procedure as the one of Synthesis Example 1 (B) (Process 1).

$^1$H-NMR (CDCl$_3$, 400 MHz) δ; 2.45 (s, 6H), 2.64 (s, 3H), 2.71 (s, 3H), 3.52 (t, 2H, J=6.2 Hz), 3.65 (t, 2H, J=6.2 Hz), 3.96 (s, 3H), 7.92–8.20 (m, 6H), 8.80 (s, 1H)

(C) Methyl 4-{2-[5-(5,6,7,8-tetramethylnaphthalen-2-yl)pyrrolyl]}benzoate

The title compound was obtained by the same procedure as the one of Synthesis Example 1 (C).

$^1$H-NMR (CDCl$_3$, 400 MHz) δ; 2.44 (s, 3H), 2.45 (s, 3H), 2.64 (s, 3H), 2.70 (s, 3H), 3.93 (s, 3H), 6.73 (dd, 1H, J=2.4, 3.2 Hz), 6.77 (dd, 1H, J=2.4, 3.2 Hz), 7.61–7.67 (m, 3H), 8.04–8.14 (m, 4H), 8.82 (brs, 1H)

(D) 4-{2-[5-(5,6,7,8-Tetramethylnaphthalen-2-yl)pyrrolyl]} benzoic Acid

The title compound was obtained by the same procedure as the one of Synthesis Example 1 (D).

$^1$H-NMR (DMSO-d$_6$, 400 MHz) δ; 2.37 (s, 3H), 2.38 (s, 3H), 2.56 (s, 3H), 2.67 (s, 3H), 6.79 (m, 2H), 7.83 (dd, 1H, J=1.2, 8.8 Hz), 7.89 (d, 2H, J=8.0 Hz), 7.93 (d, 2H, J=8.0 Hz), 8.39 (d, 1H, J=1.2 Hz), 11.6 (s, 1H)

Synthesis Example 4
4-{2-[5-(7-methoxy-8-methylnaphthalen-2-yl)pyrrolyl]} benzoic Acid (A) Methyl 4-[4-(7-methoxy-8-methylnaphthalen-2-yl)-4-oxobutanoyl]benzoate The title compound was obtained by the same procedure as the one of Synthesis Example 1 (B) (Process 2).

$^1$H-NMR (CDCl$_3$, 400 MHz) δ; 2.64 (s, 3H), 3.53 (t, 2H, J=6.0 Hz), 3.65 (t, 2H, J=6.0 Hz), 3.96 (s, 3H), 3.98 (s, 3H), 7.38 (d, 1H, J=9.2 Hz), 7.76 (d, 1H, J=9.2 Hz), 7.85 (d, 1H, J=8.8 Hz), 7.93 (dd, 1H, J=1.6, 8.8 Hz), 8.12 (d, 2H, J=8.8 Hz), 8.15 (d, 2H, J=8.8 Hz), 8.71 (m, 1H)

(B) Methyl 4-{2-[5-(7-methoxy-8-methylnaphthalen-2-yl)pyrrolyl]}benzoate

The title compound was obtained by the same procedure as the one of Synthesis Example 1 (C).

$^1$H-NMR (CDCl$_3$, 400 MHz) δ; 2.62 (s, 3H), 3.94 (s, 3H), 3.97 (s, 3H), 6.73–6.78 (m, 2H), 7.24 (d, 1H, J=8.8 Hz), 7.56 (dd, 1H, J=2.0, 8.4 Hz), 7.63 (d, 2H, J=8.4 Hz), 7.70 (d, 1H, J=8.8 Hz), 7.81 (d, 1H, J=8.4 Hz), 8.02 (s, 1H), 8.07 (d, 2H, J=8.4 Hz), 8.83 (brs, 1H)

(C) 4-{2-[5-(7-Methoxy-8-methylnaphthalen-2-yl)pyrrolyl]} benzoic acid

The title compound was obtained by the same procedure as the one of Synthesis Example 1 (D).

$^1$H-NMR (DMSO-d$_6$, 400 MHz) δ; 2.56 (s, 3H), 3.90 (s, 3H) 6.81 (d, 2H, J=2.2 Hz), 7.33 (d, 1H, J=8.9 Hz), 7.72–7.77 (m, 2H), 7.82 (d, 1H, J=8.4 Hz), 7.90 (d, 2H, J=8.8 Hz), 7.93 (d, 2H, J=8.8 Hz), 8.30 (s, 1H), 11.6 (s, 1H)

Synthesis Example 5
4-{2-[5-(7-Methoxy-8-ethylnaphthalen-2-yl)pyrrolyl]} benzoic Acid (A) Methyl 4-[4-(7-methoxy-8-ethylnaphthalen-2-yl)-4-oxobutanoyl]benzoate The title compound was obtained by the same procedure as the one of Synthesis Example 1 (B) (Process 2).

¹H-NMR (CDCl₃, 400 MHz) δ; 1.27 (t, 3H, J=7.4 Hz), 3.18 (q, 2H, J=7.4 Hz), 3.54 (t, 2H, J=6.1 Hz), 3.64 (t, 2H, J=6.1 Hz), 3.96 (s, 3H), 3.98 (s, 3H), 7.39 (d, 1H, J=9.2 Hz), 7.76 (d, 1H, J=9.2 Hz), 7.85 (d, 1H, J=8.4 Hz), 7.92 (dd, 1H, J=1.6, 8.4 Hz), 8.13 (d, 2H, J=8.4 Hz), 8.16 (d, 2H, J=8.4 Hz), 8.72 (s, 1H)

(B) Methyl 4-{2-[5-(7-methoxy-8-ethylnaphthalen-2-yl)pyrrolyl]}benzoate

The title compound was obtained by the same procedure as the one of Synthesis Example 1 (C).

¹H-NMR (CDCl₃, 400 MHz) δ; 1.29 (t, 3H, J=7.5 Hz), 3.16 (q, 2H, J=7.5 Hz), 3.94 (s, 3H), 3.97 (s, 3H), 6.73–6.78 (m, 2H), 7.24 (d, 1H, J=8.8 Hz), 7.54 (dd, 1H, J=2.0, 8.4 Hz), 7.63 (d, 2H, J=8.0 Hz), 7.70 (d, 1H, J=8.8 Hz), 7.82 (d, 1H, J=8.4 Hz), 8.04 (s, 1H), 8.07 (d, 2H, J=8.0 Hz), 8.82 (brs, 1H)

(C) 4-{2-[5-(7-Methoxy-8-ethylnaphthalen-2-yl(pyrrolyl]}benzoic Acid

The title compound was obtained by the same procedure as the one of Synthesis Example 1 (D).

¹H-NMR (DMSO-d₆, 400 MHz) δ; 1.18 (t, 3H, J=7.6 Hz), 3.14 (q, 2H, J=7.6 Hz), 3.91 (s, 3H), 6.81 (m, 2H), 7.33 (d, 1H, J=8.8 Hz), 7.74 (d, 2H, J=8.8 Hz), 7.83 (d, 1H, J=8.8 Hz), 7.91 (d, 2H, J=8.4 Hz), 7.94 (d, 2H, J=8.4 Hz), 8.28 (s, 1H), 11.6 (s, 1H)

Synthesis Example 6

4-{2-[5-(8-Methylnaphthalen-2-pyrrolyl]}benzoic Acid (A) Methyl 4-[4-(8-methylnaphthalen-2-yl)-4-oxo-butanoyl]benzoate The title compound was obtained by the same procedure as the one of Synthesis Example 1 (B) (Process 2).

¹H-NMR (CDCl₃, 400 MHz) δ; 2.79 (s, 3H), 3.54 (t, 2H, J=6.4 Hz), 3.66 (t, 2H, J=6.4 Hz), 3.96 (s, 3H), 7.40 (d, 1H, J=8.0 Hz), 7.50 (t, 1H, J=8.0 Hz), 7.74 (d, 1H, J=8.0 Hz), 7.92 (d, 1H, J=8.4 Hz), 8.08 (dd, 1H, J=2.0, 8.4 Hz), 8.12 (d, 2H, J=8.8 Hz), 8.16 (d, 2H, J=8.8 Hz), 8.75 (s, 1H)

(B) Methyl 4-{2-[5-(8-methylnaphthalen-2-yl)pyrrolyl]}benzoate

The title compound was obtained by the same procedure as the one of Synthesis Example 1 (C).

¹H-NMR (CDCl₃, 400 MHz) δ; 2.76 (s, 3H), 3.94 (s, 3H), 6.74–6.78 (m, 2H), 7.34–7.36 (m, 2H), 7.64 (d, 2H, J=8.4 Hz), 7.68–7.72 (m, 2H), 7.88 (d, 1H, J=8.4 Hz), 8.06–8.10 (m, 3H), 8.84 (brs, 1H)

(C) 4-{2-[5-(8-Methylnaphthalen-2-yl)pyrrolyl]}benzoic Acid

The title compound was obtained by the same procedure as the one of Synthesis Example 1 (D).

¹H-NMR (DMSO-d₆, 400 MHz) δ; 2.73 (s, 3H), 6.83 (d, 2H, J=2.0 Hz), 7.30–7.36 (m, 2H), 7.70 (m, 1H), 7.86–7.96 (m, 6H), 8.37 (s, 1H), 11.6 (s, 1H)

Synthesis Example 7

4-{2-[5-(8-Ethylnaphthalen-2-yl)pyrrolyl]}benzoic Acid (A) Methyl 4-[4-(8-ethylnaphthalen-2-yl)-4-oxo-butanoyl]benzoate The title compound was obtained by the same procedure as the one of Synthesis Example 1 (B) (Process 2).

¹H-NMR (CDCl₃, 400 MHz) δ; 1.42 (t, 3H, J=7.5 Hz), 3.20 (q, 2H, J=7.5 Hz), 3.55 (t, 2H, J=6.4 Hz), 3.65 (t, 2H, J=6.4 Hz), 3.96 (s, 3H), 7.42 (d, 1H, J=7.6 Hz), 7.53 (t, 1H, J=7.6 Hz), 7.74 (d, 1H, J=8.0 Hz), 7.92 (d, 1H, J=8.8 Hz), 8.07 (dd, 1H, J=2.0, 8.8 Hz), 8.13 (d, 2H, J=8.4 Hz), 8.16 (d, 2H, J=8.4 Hz), 8.81 (s, 1H)

(B) Methyl 4-{2-[5-(8-ethylnaphthalen-2-yl)pyrrolyl]}benzoate

The title compound was obtained by the same procedure as the one of Synthesis Example 1 (C).

¹H-NMR (CDCl₃, 400 MHz) δ; 1.44 (t, 3H, J=7.5 Hz), 3.18 (q, 2H, J=7.5 Hz), 3.94 (s, 3H), 6.74 (dd, 1H, J=2.8, 3.6 Hz), 6.78 (dd, 1H, J=2.8, 3.6 Hz), 7.36–7.42 (m, 2H), 7.63 (d, 2H, J=8.4 Hz), 7.67–7.70 (m, 2H), 7.89 (d, 1H, J=8.8 Hz), 8.08 (d, 2H, J=8.4 Hz), 8.13 (s, 1H), 8.82 (brs, 1H)

(C) 4-{2-[5-(8-Ethylnaphthalen-2-yl)pyrrolyl]}benzoic Acid

The title compound was obtained by the same procedure as the one of Synthesis Example 1 (D).

¹H-NMR (DMSO-d₆, 400 MHz) δ; 1.35 (t, 3H, J=7.5 Hz), 3.18 (q, 2H, J=7.5 Hz), 6.82 (s, 2H), 7.34–7.37 (m, 2H), 7.70 (m, 1H), 7.88–7.96 (m, 6H), 8.41 (s, 1H), 11.6 (s, 1H)

Synthesis Example 8

4-{2-[8-(Isopropylnaphthalen-2-yl)pyrrolyl]}benzoic Acid (A) Methyl 4-[4-(8-isopropylnaphthalen-2-yl)-4-oxo-butanoyl]benzoate The title compound was obtained by the same procedure as the one of Synthesis Example 1 (B) (Process 2).

¹H-NMR (CDCl₃, 400 MHz) δ; 1.44 (d, 6H, J=7.0 Hz), 3.54 (t, 2H, J=6.4 Hz), 3.66 (t, 2H, J=6.4 Hz), 3.87 (q, 1H, J=7.0 Hz), 3.96 (s, 3H), 7.50 (d, 1H, J=8.0 Hz), 7.58 (t, 1H, J=8.0 Hz), 7.73 (d, 1H, J=8.0 Hz), 7.92 (d, 1H, J=8.4 Hz), 8.06 (dd, 1H, J=1.6, 8.8 Hz), 8.12 (d, 2H, J=8.0 Hz), 8.16 (d, 2H, J=8.0 Hz), 8.90 (s, 1H)

(B) Methyl 4-{2-[5-(8-isopropylnaphthalen-2-yl)pyrrolyl]}benzoate

The title compound was obtained by the same procedure as the one of Synthesis Example 1 (C).

¹H-NMR (CDCl₃, 400 MHz) δ; 1.45 (d, 6H, J=7.2 Hz), 3.83 (quint., 1H, J=7.2 Hz), 3.94 (s, 3H), 6.74 (dd, 1H, J=2.4, 4.0 Hz), 6.78 (dd, 1H, J=2.4, 4.0 Hz), 7.41–7.46 (m, 2H), 7.63 (d, 2H, J=8.8 Hz), 7.67–7.70 (m, 2H), 7.89 (d, 1H, J=8.4 Hz), 8.07 (d, 2H, J=8.8 Hz), 8.21 (s, 1H), 8.82 (brs, 1H)

(C) 4-{2-[5-(8-Isopropylnaphthalen-2-yl)pyrrolyl]}benzoic Acid

The title compound was obtained by the same procedure as the one of Synthesis Example 1 (D).

¹H-NMR (DMSO-d₆, 400 MHz) δ; 1.37 (d, 6H, J=6.8 Hz), 3.96 (quint., 1H, J=6.8 Hz), 6.81 (m, 2H), 7.37–7.44 (m, 2H), 7.69 (d, 1H, J=8.0 Hz), 7.88–7.96 (m, 6H), 8.48 (s, 1H), 11.6 (s, 1H)

Synthesis Example 9

4-{2-[8-Isopropenylnaphthalen-2-yl)pyrrolyl]}benzoic Acid (A) Methyl 4-[4-(8-isopropenylnaphthalen-2-yl)-4-oxobutanoyl]benzoate The title compound was obtained by the same procedure as the one of Synthesis Example 1 (B) (Process 2).

¹H-NMR (CDCl₃, 40 MHz) δ; 2.25 (s, 3H) 3.52 (t, 2H, J=6.4 Hz), 3.63 (t, 2H, J=6.4 Hz), 3.96 (s, 3H), 5.10 (m, 1H), 5.51 (m, 1H), 7.40 (dd, 1H, J=1.2, 6.8 Hz), 7.56 (t, 1H, J=8.0 Hz), 7.79 (d, 1H, J=8.4 Hz), 7.91 (d 1H, J=8.4 Hz), 8.06 (dd, 1H, J=2.0, 8.8 Hz), 8.11 (d, 2H, J=8.4 Hz), 8.16 (d, 2H, J=8.4 Hz), 8.82 (s, 1H)

(B) Methyl 4-{2-[5-(8-isopropenylnaphthalen-2-yl)pyrrolyl]}benzoate

The title compound was obtained by the same procedure as the one of Synthesis Example 1 (C).

¹H-NMR (CDCl₃, 400 MHz) δ; 2.28 (s, 3H), 3.94 (s, 3H), 5.13 (m, 1H), 5.49 (m, 1H), 6.72 (dd, 1H, J=2.8, 3.6 Hz), 6.76 (dd, 1H, J=2.4, 3.6 Hz), 7.34 (dd, 1H, J=1.6, 7.2 Hz), 7.41 (dd, 1H, J=7.2, 8.0 Hz), 7.62 (d, 2H, J=8.8 Hz), 7.70 (dd, 1H, J=2.0, 8.8 Hz), 7.74 (d, 1H, J=8.0 Hz), 7.88 (d, 1H, J=8.4 Hz), 8.07 (d, 2H, J=8.8 Hz), 8.14 (s, 1H), 8.79 (brs, 1H)

(C) 4-{2-[5-(8-Isopropenylaphthalen-2-yl)pyrrolyl]}benzoic Acid

The title compound was obtained by the same procedure as the one of Synthesis Example 1 (D).

$^1$H-NMR (DMSO-d$_6$, 400 MHz) δ; 2.23 (s, 3H), 5.07 (m, 1H), 5.46 (m, 1H), 6.70 (m, 1H), 6.81 (m, 1H), 7.31 (d, 1H, J=7.2 Hz), 7.40 (t, 1H, J=8.0 Hz), 7.88–7.95 (m, 6H), 8.23 (s, 1H), 11.6 (s, 1H)

Synthesis Example 10
4-{2-[5-(8-Phenylnaphthalen-2-yl)pyrrolyl]}benzoic Acid
(A) Methyl 4-[4-(8-phenylnaphthalen-2-yl)-4-oxobutanoyl]benzoate The title compound was obtained by the same procedure as the one of Synthesis Example 1 (B) (Process 2).

$^1$H-NMR (CDCl$_3$, 400 MHz) μ; 3.45 (m, 4H), 3.95 (s, 3H), 7.46–7.54 (m, 6H), 7.66 (t, 1H, J=8.0 Hz), 7.90 (d, 1H, J=8.4 Hz), 7.98 (d, 1H, J=8.8 Hz), 8.06–8.10 (m, 3H), 8.13 (d, 2H, J=8.4 Hz), 8.66 (s, 1H)

(B) Methyl 4-{2-[5-(8-phenylnaphthalen-2-yl)pyrrolyl]}benzoate

The title compound was obtained by the same procedure as the one of Synthesis Example 1 (C).

$^1$H-NMR (CDCl$_3$, 400 MHz) δ; 3.92 (s, 3H), 6.64 (dd, 1H, J=2.4, 3.6 Hz), 6.71 (dd, 1H, J=2.4, 3.6 Hz), 7.44 (dd, 1H, J=1.6, 7.2 Hz), 7.48–7.56 (m, 8H), 7.72 (dd, 1H, J=1.6, 8.4 Hz), 7.84 (d, 1H, J=8.4 Hz), 7.94 (d, 1H, J=8.4 Hz), 8.00 (s, 1H), 8.03 (d, 2H, J=8.4 Hz), 8.71 (brs, 1H)

(C) 4-{2-[5-(8-Phenylnaphthalen-2-yl)pyrrolyl]}benzoic Acid

The title compound was obtained by the same procedure as the one of Synthesis Example 1 (D).

$^1$H-NMR (DMSO-d$_6$, 400 MHz) δ; 6.48 (m, 1H), 6.72 (m, 1H), 7.41 (dd, 1H, J=1.2, 6.8 Hz), 7.46–7.58 (m, 6H), 7.78 (d, 2H, J=8.4 Hz), 7.88 (d, 2H, J=8.4 Hz), 7.91 (d, 1H, J=8.4 Hz), 8.00 (dd, 1H, J=1.2, 7.8 Hz), 8.02 (d, 1H, J=7.8 Hz), 8.09 (s, 1H), 11.6 (s, 1H)

Synthesis Example 11
4-{2-[5-(5,8-Dimethylnaphthalen-2-yl)-1-methylpyrrolyl]}benzoic Acid
(A) Methyl 4-{2-[5-(5,8-dimethylnaphthalen-2-yl)-1-methylpyrrolyl]}benzoate In a nitrogen atmosphere, methyl 4-{2-[5-(5,8-dimethylnaphthalen-2-yl)pyrrolyl]}benzoate (240 mg) was dissolved in N,N-dimethylformamide (5 ml). Then, sodium hydride (60%, 33 mg) was added and the resultant mixture was stirred for 1 hr. Next, methyl iodide (0.06 ml) was added dropwise to the mixture at 0° C. followed by stirring at room temperature for 1 hr. After adding a saturated aqueous solution of ammonium chloride, the mixture was extracted with ethyl acetate (30 ml×2). The organic layers were combined, washed with brine and dried over anhydrous magnesium sulfate. After filtering, the filtrate was concentrated to give the title compound (300 mg) as a crude product.

$^1$H-NMR (CDCl$_3$, 400 MHz) δ; 2.70 (s, 6H), 3.72 (s, 3H), 3.94 (s, 3H), 6.47 (d, 1H, J=3.6 Hz), 6.49 (d, 1H, J=3.6 Hz), 7.21–7.26 (m, 2H), 7.59 (d, 2H, J=8.0 Hz), 7.66 (dd, 1H, J=1.6, 8.4 Hz), 8.06–8.12 (m, 4H)

(B) 4-{2-[5-(5,8-Dimethylnaphthalen-2-yl)-1-methylpyrrolyl]}benzoic acid

The title compound was obtained by the same procedure as the one of Synthesis Example 1 (D).

$^1$H-NMR (DMSO-d$_6$, 400 MHz) δ; 2.62 (s, 3H), 2.66 (s, 3H), 3.71 (s, 3H), 6.48 (m, 2H), 7.24 (d, 1H, J=6.8 Hz), 7.26 (d, 1H, J=6.8 Hz), 7.68 (d, 2H, J=8.0 Hz), 7.73 (d, 1H, J=7.6 Hz), 7.99 (d, 2H, J=8.0 Hz), 8.07 (m, 2H)

Synthesis Example 12
4-{2-[5-(5,8-Dimethylnaphthalen-2-yl)-1-isopropylpyrrolyl]}benzoic Acid
(A) Methyl 4-{2-[5-(5,8-dimethylnaphthalen-2-yl)-1-isopropylpyrrolyl]}benzoate Methyl 4-[4-(5,8-dimethylnaphthalen-2-yl)-4-oxobutanoyl]benzoate (0.23 g) was dissolved in acetic acid (4 ml). After adding isopropylamine (4 ml) at room temperature, the resultant mixture was heated under reflux for 2 hr. After cooling to room temperature by allowing to stand, water was added to the mixture followed by extraction with ethyl acetate (30 ml×2). The organic layers were combined, washed successively with a saturated aqueous solution of sodium bicarbonate and brine and dried over anhydrous magnesium sulfate. After filtering, the filtrate was concentrated. The resulting crude product was purified by silica gel column chromatography to give the title compound (95 mg).

$^1$H-NMR (CDCl$_3$, 400 MHz) δ; 1.30 (d, 6H, J=7.0 Hz), 2.69 (s, 3H), 2.71 (s, 3H), 3.96 (s, 3H), 4.58 (quint., 1H, J=7.0 Hz), 6.29 (s, 2H), 7.23–7.28 (m, 2H), 7.58 (d, 2H, J=8.2 Hz), 7.65 (dd, 1H, J=1.6, 8.4 Hz), 8.05 (d, 1H, J=8.4 Hz), 8.08–8.11 (m, 3H)

(B) 4-{2-[5-(5,8-Dimethylnaphthalen-2-yl)-1-isopropylpyrrolyl]}benzoic Acid

The title compound was obtained by the same procedure as the one of Synthesis Example 1 (D).

$^1$H-NMR (DMSO-d$_6$, 400 MHz) δ; 1.22 (d, 6H, J=7.0 Hz), 2.63 (s, 6H), 4.50 (quint., 1H, J=7.0 Hz), 6.23 (s, 2H), 7.27 (q, AB type, 2H, J=6.8 Hz) 7.58 (d, 2H, J=8.0 Hz), 7.64 (dd, 1H, J=1.6, 8.8 Hz), 7.99 (m, 3H), 8.06 (d, 1H, J=8.8 Hz), 12.9 (brs. 1H)

Synthesis Example 13
4-{2-[5-(4,7-Dimethylbenzofuran-2-yl)pyrrolyl]}benzoic Acid
(A) Methyl 4-[4-(4,7-dimethylbenzofuran-2-yl)-4-oxobutanoyl]benzoate To a solution (100 ml) of 2,5-dimethylphenol (10 g) in N,N-dimethylformamide were added anhydrous potassium carbonate (22.6 g) and bromoacetaldehyde diethyl acetal (14.8 ml) and the resultant mixture was heated to 150° C. under stirring for 2.5 hr. After cooling to room temperature by allowing to stand, it was extracted with ethyl acetate. The organic layer was washed with brine and dried over anhydrous magnesium sulfate. After evaporating the solvent, the residue was purified by silica gel column chromatography to give an ether (18 g) as a colorless oil.

The resulting product was then dissolved in toluene (100 ml). After adding polyphosphoric acid (50 g), the resultant mixture was heated to 90° C. under stirring for 1 hr in a nitrogen atmosphere. After cooling to room temperature by allowing to stand, the liquid reaction mixture was poured into ice-water and extracted with ethyl acetate. The organic layer was washed with brine and dried over anhydrous magnesium sulfate. After evaporating the solvent, the resulting residue was purified by silica gel column chromatography to give 4,7-dimethylbenzofuran (3.5 g) as a yellow oil.

In a nitrogen atmosphere, n-butyllithium (1.56 M hexane solution, 18.4 ml) was added at −35° C. to a solution (50 ml) of the 4,7-dimethylbenzofuran (3.5 g) in dry tetrahydrofuran. Then the resulting mixture was stirred for 15 min and N,N-dimethylformamide (5.6 ml) was added dropwise to the mixture. Next, the reaction mixture was heated to room temperature and ethyl acetate was added to the mixture. The organic layer was washed with brine and dried over anhydrous magnesium sulfate. After evaporating the solvent, the resulting crude crystals were washed with n-hexane to give 4,7-dimethylbenzofuran-2-carbaldehyde (2.3 g) as a pale yellow solid.

$^1$H-NMR (CDCl$_3$, 400 MHz) δ; 2.53 (s, 6H), 7.02 (d, 1H, J=6.8 Hz), 7.20 (d, 1H, J=6.8 Hz), 7.59 (s, 1H), 9.85 (s, 1H)

The 4,7-dimethylbenzofuran-2-carbaldehyde was treated as in Synthesis Example 1 (B) (Process 2) to give the title compound.

$^1$H-NMR (CDCl$_3$, 400 MHz);2.50 (s, 3H), 2.51 (s, 3H), 3.45–3.55 (m, 4H), 3.94 (s, 3H), 7.00 (d, 1H, J=6.8 Hz), 7.16 (d, 1H, J=6.8 Hz), 7.62 (s, 1H), 8.09 (d, 2H, J=8.4 Hz), 8.14 (d, 2H, J=8.4 Hz)

(B) Methyl 4-{2-[5-(4,7-dimethylbenzofuran-2-yl)pyrrolyl]} benzoate

The title compound was obtained by the same procedure as the one of Synthesis Example 1 (C).

$^1$H-NMR (CDCl$_3$, 400 MHz) δ; 2.48 (s, 3H), 2.55 (s, 3H), 3.93 (s, 3H), 6.72–6.77 (m, 2H), 6.83 (s, 1H), 6.93 (d, 1H, J=6.8 Hz), 6.97 (d, 1H, J=6.8 Hz), 7.63 (d, 2H, J=8.4 Hz), 8.07 (d, 2H, J=8.4 Hz), 9.00 (brs, 1H)

(C) 4-{2-[5-(4,7-Dimethylbenzofuran-2-yl)pyrrolyl]} benzoic Acid

The title compound was obtained by the same procedure as the one of Synthesis Example 1 (D).

$^1$H -NMR (DMSO-d$_6$, 400 MHz) δ; 2.43 (s, 3 H), 2.46 (s, 3H), 6.71 (t, 1H, J=2.4 Hz), 6.84 (t, 1H, J.=2.4 Hz), 6.92 (d, 1H, J=7.2 Hz), 6.96 (d, 1H, J=7.2 Hz), 7.23 (s, 1H), 7.89 (d, 2H, J=8.4 Hz), 7.95 (d, 2H, J=8.4 Hz), 11.81 (brs, 1H), 12.85 (brs, 1H)

Synthesis Example 14

4-{2-[5-(4,7-Dichlorobenzofuran-2-yl)pyrrolyl]}benzoic Acid

The title compound was obtained by the same procedure as the one of Synthesis Example 1.

$^1$H-NMR (DMSO-d$_6$, 400 MHz) δ; 6.83 (t, 1H, J=2.4 Hz), 6.89 (t, 1H, J=2.4 Hz), 7.35 (d, 1H, J=7.2 Hz), 7.38 (d, 1H, J=7.2 Hz), 7.39 (s, 1H), 7.91 (d, 2H, J=8.4 Hz), 7.97 (d, 2H, J=8.4 Hz), 12.02 (brs, 1H), 12.86 (brs, 1H)

Synthesis Example 15

4-{2-[5-(4,7-Dichlorobenzofuran-2yl)pyrrolyl]}benzoic Acid

The title compound was obtained by the same procedure as the one of Synthesis Example 1.

$^1$H-NMR (DMSO-d$_6$, 400 MHz) δ; 6.76 (t, 1H, J=3.2 Hz) 6.86 (t, 1H, J=3.2 Hz), 7.23 (t, 1H, J=7.6 Hz), 7.29 (s, 1H), 7.33 (dd, 1H, J=0.8, 7.6 Hz), 7.61 (dd, 1H, J=0.8, 7.6 Hz), 7.90 (d, 2H, J=8.4 Hz), 7.95 (d, 2H, J=8.4 Hz), 11.96 (s, 1H), 12.83 (brs, 1H)

Synthesis Example 16

4-{2-[5-(7-n-Propylbenzofuran-2-yl )pyrrolyl]}benzoic Acid

The title compound was obtained by the same procedure as the one of Synthesis Example 1.

$^1$H-NMR (DMSO-d$_6$, 400 MHz) δ; 0.95 (t, 3H, J=7.2 Hz) 1.75 (sext, 2H, J=7.2 Hz), 2.87 (t, 2H, J=7.2 Hz), 6.71 (t, 1H, J=3.2 Hz), 6.84 (t, 1H, J=3.2 Hz), 7.06 (dd, 1H, J=1.2, 7.6 Hz), 7.13 (t, 1H, J=7.6 Hz), 7.17 (s, 1H), 7.44 (dd, 1H, J=1.2, 7.6 Hz), 7.88 (d, 2H, J=8.4 Hz), 7.95 (d, 2H, J=8.4 Hz), 11.82 (s, 1H), 12.80 (brs, 1H)

Synthesis Example 17

4-{2-[5-(4-Methyl-7-ethylbenzofuran-9-yl )pyrrolyl]} benzoic Acid

The title compound was obtained by the same procedure as the one of Synthesis Example 1.

$^1$H-NMR (DMSO-d$_6$, 400 MHz) δ; 1.29 (t, 3H, J=7.6 Hz), 2.45 (s, 3H), 2.88 (q, 2H, J=7.6 Hz), 6.70 (m, 1H), 6.83 (m, 1H), 6.95 (d, 1H, J=7.2 Hz), 6.98 (d, 1H, J=7.2 Hz), 7.23 (s, 1H), 7.89 (d, 2H, J=8.8 Hz), 7.94 (d, 2H, J=8.8 Hz), 11.80 (s, 1H), 12.82 (brs, 1H)

Synthesis Example 18

4-{2-[5-(4-Methyl-7-n-propylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 0.93 (t, 3H, J=7.6 Hz), 1.73 (sext, 2H, J=7.6 Hz), 2.45 (s, 3H), 2.83 (t, 2H, J=7.6 Hz), 6.70 (m, 1H), 6.83 (m, 1H), 6.94 (d, 1H, J=7.2 Hz), 6.95 (d, 1H, J=7.2 Hz), 7.22 (s, 1H), 7.89 (d, 2H, J=8.4 Hz), 7.94 (d, 2H, J=8.4 Hz), 11.81 (s, 1H), 12.83 (brs, 1H)

Synthesis Example 19

4-{2-[5-(4-Chloro-7-methylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 2.48 (s, 3H), 6.78–6.82 (m, 1H), 6.85–6.88 (m, 1H), 7.09 (d, 1H, J=7.6 Hz), 7.21 (d, 1H, J=7.6 Hz), 7.29 (s, 1H), 7.90 (d, 2H, J=8.4 Hz), 7.96 (d, 2H, J=8.4 Hz), 11.91 (brs, 1H)

Synthesis Example 20

4-{2-[5-(4-Chloro-7-ethylbenzofuran-2-yl )pyrrolyl]} benzoic Acid.

The title compound was obtained by the same procedure as the one of Synthesis Example 1.

$^1$H-NMR (DMSO-d$_6$, 400 MHz) δ; 1.30 (t, 3H, J=7.5 Hz), 2.90 (q, 2H, J=7.5 Hz), 6.79 (dd, 1H, J=2.4, 3.6 Hz), 6.86 (dd, 1H, J=2.4, 3.6 Hz), 7.11 (d, 1H, J=8.0 Hz), 7.23 (d, 1H, J=8.0 Hz), 7.29 (s, 1H), 7.89 (d, 2H, J=8.8 Hz), 7.95 (d, 2H, J=8.4 Hz), 11.90 (brs, 1H)

Synthesis Example 21

4-{2-[5-(4-Chloro-7-n-ethylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 0.94 (t, 3H, J=7.2 Hz), 1.68–1.77 (m, 2H), 2.86 (t, 2H, J=7.2 Hz), 6.77–6.80 (m, 1H), 6.84–6.88 (m, 1H), 7.09 (d, 1H, J=8.4 Hz), 7.22 (d, 1H, J=8.4 Hz), 7.28 (s, 1H), 7.89 (d, 2H, J=8.8 Hz), 7.95 (d, 2H, J=8.8 Hz), 11.90 (brs, 1H)

Synthesis Example 22

4-{2-[5-Chloro-7-methylbenzofuran-2-yl)pyrrolyl]}benzoic Acid

The title compound was obtained by the same procedure as the one of Synthesis Example 1.

$^1$H-NMR (DMSO-d$_6$, 400 MHz) δ; 2.48 (s,3H) 6.74–6.77 (m, 1H), 6.83–6.86 (m, 1H), 7.10–7.13 (m, 1H), 7.17 (s, 1H), 7.52–7.54 (m, 1H), 7.88 (d, 2H, J=8.4 Hz), 7.95 (d, 2H, J=8.8 Hz), 11.89 (brs, 1H)

Synthesis Example 23

4-{2-[5-Chloro-7-ethylbenzofuran-2-yl )pyrrolyl]}benzoic Acid

The title compound was obtained by the same procedure as the one of Synthesis Example 1.

$^1$H-NMR (DMSO-d$_6$, 400 MHz) δ; 1.30 (t, 3H, J=7.6 Hz), 2.90 (q, 2H, J=7.6 Hz), 6.74 (dd, 1H, J=1.6, 3.6 Hz), 6.84 (dd, 1H, J=1.2, 3.6 Hz), 7.12 (s, 1H), 7.17 (s, 1H), 7.54 (s, 1H), 7.89 (d, 2H, J=8.4 Hz), 7.94 (d, 2H, J=8.4 Hz), 11.89 (s, 1H)

Synthesis Example 24

4-{2-Chloro-7-n-propylbenzofuran-2-yl)pyrrolyl]}benzoic Acid

The title compound was obtained by the same procedure as the one of Synthesis Example 1.

¹H-NMR (DMSO-d₆, 400 MHz) δ; 0.94 (t, 3H, J=7.6 Hz), 1.74 (sext, 2H, J=7.6 Hz), 2.86 (t, 2H, J=7.6 Hz), 6.74 (m, 1H), 6.84 (m, 1H), 7.10 (d, 1H, J=2.4 Hz), 7.18 (s, 1H), 7.54 (d, 1H, J=2.4 Hz), 7.89 (d, 2H, J=8.4 Hz), 7.94 (d, 2H, J=8.4 Hz), 11.91 (s, 1H)

Synthesis Example 25
4-{2-[5-(5-Fluoro-7-ethylbenzofuran-2-yl)pyrrolyl]}benzoic Acid The title compound was obtained by the same procedure as the one of Synthesis Example 1.

¹H-NMR (DMSO-d₆, 400 MHz) δ; 1.31 (t, 3H, J=7.6 Hz), 2.91 (q, 2H, J=7.6 Hz), 6.74 (t, 1H, J=3.6 Hz), 6.84 (t, 1H, J=3.2 Hz), 6.94 (dd, 1H, J=2.0, 10.0 Hz), 7.25 (dd, 1H, J=2.4, 8.8 Hz), 7.29 (s, 1H), 7.94 (brs, 4H), 12.04 (brs, 1H)

Synthesis Example 26
4-{2-[5-(5-Fluoro-7-n-propylbenzofuran-2-yl)pyrrolyl]}benzoic Acid The title compound was obtained by the same procedure as the one of Synthesis Example 1.

¹H-NMR (DMSO-d₆, 400 MHz) δ; 0.95 (t, 3H, J=7.2 Hz), 1.74 (q, 2H, J=7.2 Hz), 2.86 (t, 2H, J=7.2 Hz), 6.73 (dd, 1H, J=2.0, 3.6 Hz), 6.84 (dd, 1H, J=2.4, 3.6 Hz), 6.93 (dd, 1H, J=2.0, 10.4 Hz), 7.22–7.28 (m, 2H), 7.90–7.96 (brs, 4H), 12.00 (s, 1H)

Synthesis Example 27
4-{2-[5-(4,7-Difluorobenzofuran-2-yl)pyrrolyl]}benzoic Acid 2,5-Difluorophenol (10 g) was dissolved in dimethylformaldehyde (120 ml). At room temperature, potassium carbonate (21 g) and allyl bromide (8.57 ml) were successively added to the mixture and it was stirred at 80° C. for 1 hr. After adding water to the liquid reaction mixture, it was extracted with ethyl acetate. The organic layer was washed with brine, dried over anhydrous magnesium sulfate and then concentrated under reduced pressure. The resulting residue was purified by silica gel column chromatography (developing solvent: 5% ethyl acetate/n-hexane) to give 2,5-difluorophenol allyl ether (13 g) as a colorless oil.

¹H-NMR (CDCl₃, 400 MHz) δ; 4.58 (d, 2H, J=5.2 Hz), 5.33 (dd, 1H, J=2.4, 8.4 Hz), 5.44 (dd, 1H, d, J=2.4, 17.2 Hz), 5.98–6.10 (m, 1H), 6.55–6.60 (m, 1H), 6.70 (ddd, 1H, J=3.2, 6.8, 10.0 Hz), 7.01 (ddd, 1H, J=5.2, 8.8, 10.0 Hz)

The 2,5-difluorophenol allyl ether (13 g) was dissolved in N,N-dimethylaniline (90 ml) and the resulting solution was stirred under a nitrogen gas stream at 170° C. for 5 hr. Then the liquid reaction mixture was poured into a 10% aqueous solution of hydrogen chloride and extracted with ethyl acetate. The organic layer was washed with brine, dried over anhydrous magnesium sulfate and concentrated under reduced pressure. The resulting residue was purified by silica gel column chromatography (developing solvent: 7% ethyl acetate/n-hexane) to give 2-allyl-3,6-difluorophenol (7.8 g) as a colorless oil.

¹H-NMR (CDCl₃, 400 MHz) δ; 3.44 (dd, 2H, J=1.2, 6.0 Hz)) 5.05–5.09 (m, 1H), 5.26–5.28 (m, 1H), 5.90–5.99 (m, 1H), 6.56 (dt, 1H, J=4.4, 9.2 Hz), 6.91 (dt, 1H, J=5.2, 9.2 Hz)

The 2-allyl-3,6-difluorophenol (7.0 g) was dissolved in dichloromethane (100 ml). After adding 3-chloroperbenzoic acid under a nitrogen gas stream at 0° C., the resultant mixture was stirred at room temperature for 2 hr. After adding water to the liquid reaction mixture, it was extracted with dichloromethane. The organic layer was washed successively with a saturated aqueous solution of sodium bicarbonate and brine, dried over anhydrous magnesium sulfate and concentrated under reduced pressure to give an epoxide (7.2 g) as a crude product. The thus obtained epoxide (7.2 g) was dissolved in dimethyl sulfoxide (30 ml) and water (10 ml). After adding potassium hydroxide at room temperature, the resultant mixture was stirred for 4 hr. Next, ethyl acetate was added to the reaction mixture and the organic layer was washed with brine, dried over anhydrous magnesium sulfate and concentrated under reduced pressure. The resulting residue was purified by silica gel column chromatography (developing solvent: 20% ethyl acetate/n-hexane) to give fluoro-2,3-dihydro-2-hydroxymethylbenzofuran (1.2 g) as a colorless oil.

¹H-NMR (CDCl₃, 400 MHz) δ; 3.25 (dd, 1H, J=6.7, 16 Hz), 3.33 (dd, 1H, J=8.0, 16.0 Hz), 3.75–3.83 (m, 1H), 3.90–3.97 (m, 1H), 5.04–5.13 (m, 1H), 6.49 (ddd, 1H, J=2.8, 10.0, 11.2 Hz), 6.87 (dt, 1H, J=4.4, 10.0 Hz)

The 4,7-difluoro-2,3-dihydro-2-hdyroxymethylbenzofuran (1.2 g) was dissolved in pyridine (6 ml). After adding acetic anhydride (0.73 ml) under a nitrogen gas stream at 0° C., the resultant mixture was stirred at room temperature for 17 hr. Then the liquid reaction mixture was poured into a 10% aqueous solution of hydrogen chloride and extracted with ethyl acetate. The organic layer was washed with brine, dried over anhydrous magnesium sulfate and concentrated under reduced pressure. The resulting residue was purified by silica gel column chromatography (developing solvent: 5% ethyl acetate/n-hexane) to give 2-acetoxymethyl-4,7-difluoro-2,3-dihydrobenzofuran (750 mg) as a colorless oil.

¹H-NMR (CDCl₃, 400 MHz) δ; 2.17 (s, 3H), 3.08 (dd, 1H, J=7.2, 15.6 Hz), 3.39 (dd, 1H, J=10.0, 15.6 Hz), 4.28 (dd, 1H, J=6.4, 12 Hz), 4.36 (dd, 1H, J=3.6, 12 Hz), 5.13–5.20 (m, 1H), 6.51 (ddd, 1H, J=2.8, 10.0, 10.8 Hz), 6.89 (dt, 1H, J=4.4, 10.0 Hz)

The 2-acetoxymethyl-4,7-difluoro-2,3-dihydrobenzofuran (750 mg) was dissolved in carbon tetrachloride (15 ml). After successively adding N-bromosuccinimide (582 mg) and azodiisopropylnitrile (10 mg) at room temperature, the resultant mixture was heated under reflux for 1 hr. Then the liquid reaction mixture was filtered through a glass filter and the filtrate was concentrated. To the resulting oil was added ethyl acetate. Next, the organic layer was washed with brine, dried over anhydrous magnesium sulfate and concentrated under reduced pressure to give a bromide (800 mg) as a crude product. This bromide was dissolved in tert-butyl alcohol (6 ml). Under a nitrogen gas stream, potassium tert-butoxide (a 1.0 M solution in tert-butyl alcohol, 3.3 ml) was added to the mixture at room temperature and the resultant mixture was stirred at room temperature for 2 hr. After adding ethyl acetate to the liquid reaction mixture, the organic layer was washed with brine, dried over anhydrous magnesium sulfate and concentrated under reduced pressure. The resulting residue was purified by silica gel column chromatography (developing solvent: 10% ethyl acetate/n-hexane) to give 2-acetoxymethyl-4,7-difluorobenzofuran (252 mg) as a colorless oil.

¹H-NMR (CDCl₃, 400 MHz) δ; 2.14 (s, 3H), 5.20 (s, 2H), 6.84 (dt, 1H, J=3.2, 8.8 Hz), 6.89 (d, 1H, J=2.4 Hz), 6.98 (ddd, ₁H, J=4.0, 8.8 Hz)

The 2-acetoxymethyl-4,7-difluorobenzofuran (252 mg) was dissolved in methanol (5 ml). After adding potassium carbonate (455 mg) at room temperature, the resulting mixture was stirred at the same temperature for 2 hr. Then ethyl acetate was added to the liquid reaction mixture and the organic layer was washed with brine, dried over anhydrous magnesium sulfate and concentrated under reduced pressure. The resulting residue was purified by silica gel column chromatography (developing solvent: 5% ethyl acetate/n-hexane) to give 4,7-difluoro-2-hydroxybenzofuran (161 mg) as a colorless oil.

$^1$H-NMR (CDCl$_3$, 400 MHz) δ; 4.80 (d, 2H, J=4.0 Hz), 6.80 (d, 1H, J=2.8 Hz), 6.83 (dt, 1H, J=2.8, 8.4 Hz), 6.95 (ddd, 1H, J=4.0, 8.4, 10.0 Hz)

Oxalyl chloride (0.26 ml) was added at −78° C. to dimethyl sulfoxide (0.42 ml) and dichloromethane (7 ml) and the resultant mixture was stirred at the same temperature for 3 min. Next, the 4,7-difluoro-2-hydroxybenzofuran (272 mg) was added to the mixture at the same temperature followed by stirring for 40 min. After adding triethylamine (1.2 ml) to the liquid reaction mixture, it was heated to room temperature and then stirred at room temperature for additional 30 min. Then water was added to the liquid reaction mixture followed by extraction with ethyl acetate. The organic layer was washed with brine, dried over anhydrous magnesium sulfate and concentrated under reduced pressure. The resulting residue was purified by silica gel column chromatography (developing solvent: 5% ethyl acetate/n-hexane) to give 4,7-difluorobenzofuran-2-carbaldehyde (169 mg) as a colorless solid.

$^1$H-NMR (CDCl$_3$, 400 MHz) δ; 6.96 (dt, 1H, J=2.8, 8.8 Hz), 7.21 (ddd, 1H, J=4.0, 8.8, 9.6 Hz), 7.66 (d, 1H, J=2.4 Hz), 9.92 (s, 1H)

The aldehyde was treated as in Synthesis Example 1 to give the title compound.

$^1$H-NMR (DMSO-d$_6$, 400 MHz) δ; 6.82 (dd, 1H, J=2.4, 3.6 Hz), 6.86 (dd, 1H, J=2.4, 3.6 Hz), 7.08 (dd, 1H, J=3.2, 8.8 Hz), 7.19 (dd, 1H, J=3.2, 8.8 Hz), 7.42 (d, 1H, J=2.4 Hz), 7.92 (d, 2H, J=8.4 Hz), 7.96 (d, 2H, J=8.4 Hz), 12.08 (s, 1H)

Synthesis Example 28

4-{2-[5-(5-Chloro-7-ispopropenylbenzofuran-2-yl[)pyrrolyl])}benzoic Acid

The title compound was obtained by the same procedure as the one of Synthesis Example 1.

$^1$H-NMR (DMSO-d$_6$, 400 MHz) δ; 2.25 (s, 3H), 5.48 (s, 1H), 5.93 (s, 1H), 6.74 (m, 1H), 6.84 (m, 1H), 7.23 (m, 2H), 7.67 (m, 1H), 7.88 (d, 2H, J=8.4 Hz), 7.94 (d, 2H, J=8.4 Hz), 11.96 (s, 1H), 12.87 (brs, 1H)

Synthesis Example 29

4-{2-[5-(5-Chloro-7isopropylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.34 (d, 6H, J=7.2 Hz), 3.44 (quint, 1H, J=7.2 Hz), 6.75 (m, 1H), 6.84 (m, 1H), 7.12 (m, 1H), 7.18 (d, 1H, J=0.8 Hz), 7.54 (dd, 1H, J=1.2, 2.0 Hz), 7.89 (d, 2H, J=8.0 Hz), 7.94 (d, 2H, J=8.0 Hz), 11.91 (s, 1H), 12.88 (brs, 1H)

Synthesis Example 30

4-{2-[5-(5-Methyl-7-n-propylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 0.94 (t, 3H, J=7.2 Hz), 1.74 (sext, 2H, J=7.2 Hz), 2.34 (s, 3H), 2.82 (t, 2H, J=7.2 Hz), 6.68 (m, 1H), 6.83 (m, 1H), 6.88 (s, 1H), 7.11 (s, 1H), 7.22 (s, 1H), 7.88 (d, 2H, J=8.4 Hz), 7.94 (d, 2H, J=8.4 Hz), 11.81 (s, 1H), 12.86 (brs, 1H)

Synthesis Example 31

4-{2-[5-(5-Methyl-7-isopropenylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 2.26 (s, 3H), 2.38 (s, 3H), 5.40 (s, 1H), 5.88 (s, 1H), 6.68 (m, 1H), 6.83 (m, 1H), 7.08 (s, 1H), 7.15 (s, 1H), 7.36 (s, 1H), 7.88 (d, 2H, J=8.4 Hz), 7.94 (d, 2H, J=8.4 Hz), 11.84 (s, 1H), 12.83 (brs, 1H)

Synthesis Example 32

4-{2-[5-(5-Methyl-7-isopropylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.34 (d, 6H, J=6.8 Hz), 2.35 (s, 3H), 3.40 (quint, 1H, J=6.8 Hz), 6.68 (dd, 1H, J=2.4, 3.6 Hz), 6.82 (dd, 1H, J=2.4, 3.6 Hz), 6.92 (s, 1H), 7.10 (s, 1H), 7.22 (s, 1H), 7.88 (d, 2H, J=8.8 Hz), 7.94 (d, 2H, J=8.8 Hz), 11.79 (s, 1H), 12.82 (brs, 1H)

Synthesis Example 33

4-{2-[5-(5-Methyl-7-ethylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.30 (t, 3H, J=7.6 Hz), 2.35 (s, 3H), 2.87 (q, 2H, J=7.6 Hz), 6.69 (m, 1H), 6.83 (m, 1H), 6.90 (s, 1H), 7.11 (s, 1H), 7.22 (s, 1H), 7.88 (d, 2H, J=7.6 Hz), 7.94 (d, 2H, J=7.6 Hz), 11.81 (s, 1H), 12.84 (brs, 1H)

Synthesis Example 34

4-{2-[5-(4-Methyl-7-isopropylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.33 (d, 6H, J=6.8 Hz), 2.44 (s, 3H), 3.41 (quint, 1H, J=6.8 Hz), 6.70 (m, 1H), 6.84 (m, 1H), 6.95 (d, 1H, J=7.6 Hz), 7.00 (d, 1H, J=7.6 Hz), 7.22 (s, 1H), 7.88 (d, 2H, J=7.6 Hz), 7.94 (d, 2H, J=7.6 Hz), 11.80 (s, 1H), 12.84 (brs, 1H)

Synthesis Example 35

4-{2-[5-(5-Methyl-7-ethylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.30 (t, 3H, J=7.6 Hz), 2.87 (q, 1H, J=7.6 Hz), 3.77 (s, 3H), 6.69 (m, 2H), 6.83 (dd, 1H, J=2.4, 3.6 Hz), 6.97 (d, 1H, J=2.4 Hz), 7.12 (s, 1H), 7.88 (d, 2H, J=8.4 Hz), 7.94 (d, 2H, J=8.4 Hz), 11.80 (s, 1H), 12.83 (brs, 1H)

Synthesis Example 36

4-{2-[5-(5-Methoxy-7-n-propylbenzofuran-2-yl) pyrrolyl]} benzoic acid

The title compound was obtained by the same procedure as the one of Synthesis Example 1.

$^1$H-NMR (DMSO-d$_6$, 400 MHz) δ; 0.94 (t, 3H, J=7.2 Hz), 1.74 (sext, 2H, J=7.6 Hz), 2.82 (t, 2H, J=7.6 Hz), 3.76 (s, 3H), 6.66 (s, 1H), 6.68 (m, 1H), 6.83 (m, 2H), 6.98 (s, 1H), 7.12 (d, 1H, J=1.6 Hz), 7.88 (d, 2H, J=8.4 Hz), 7.94 (d, 2H, J=8.4 Hz), 11.80 (s, 1H), 12.83 (brs, 1H)

Synthesis Example 37

4-{2-[5-(4-Methoxy-7-ethylbenzofuran-2-yl)pyrrolyl]} benzoic Acid

The title compound was obtained by the same procedure as the one of Synthesis Example 1.

$^1$H-NMR (DMSO-d$_6$, 400 MHz) δ; 1.28 (t, 3H, J=7.6 Hz), 2.84 (q, 2H, J=7.6 Hz), 3.87 (s, 3H), 6.68 (s, 1H), 6.69 (d, 1H, J=8.0 Hz), 6.82 (s, 1H), 7.01 (d, 1H, J=8.0 Hz), 7.23 (s,

1H), 7.87 (d, 2H, J=8.0 Hz), 7.94 (d, 2H, J=8.0 Hz), 11.73 (s, 1H), 12.80 (brs, 1H)

Synthesis Example 38
4-{2-[5-(4-Methoxy-7-n-propylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 0.93 (t, 3H, J=7.6 Hz), 1.70 (m, 2H), 2.79 (t, 2H, J=7.6 Hz), 3.88 (s, 3H), 6.68 (m, 2H), 6.82 (m, 1H), 6.99 (d, 1H, J=8.0 Hz), 7.23 (s, 1H), 7.87 (d, 2H, J=8.0 Hz), 7.93 (d, 2H, J=8.0 Hz), 11.73 (s, 1H), 12.68 (brs, 1H)

Synthesis Example 39
4-{2-[5-(Indano[4,5-b]furan-2-yl)pyrrolyl]}benzoic Acid The title compound was obtained by the same procedure as the one of Synthesis Example 1.

$^1$H-NMR (DMSO-$d_6$, 400 MHz) δ; 2.14 (quint, 2H, J=7.2 Hz), 2.97 (t, 2H, J=7.2 Hz), 3.10 (t, 2H, J=7.2 Hz), 6.68 (m, 1H), 6.82 (m, 1H), 7.12 (d, 1H, J=7.6 Hz), 7.17 (s, 1H), 7.39 (d, 1H, J=7.6 Hz), 7.88 (d, 2H, J=7.6 Hz), 7.94 (d, 2H, J=7.6 Hz), 11.81 (s, 1H), 12.82 (brs, 1H)

Synthesis Example 40
4-{2-[5-(6,7-Dimethylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 2.30 (s, 3H), 2.42 (s, 3H), 6.69–6.72 (m, 1H), 6.81–6.84 (m, 1H), 7.02 (d, 1H, J=8.4 Hz), 7.11 (s, 1H), 7.30 (d, 1H, J=8.4 Hz), 7.88 (d, 2H, J=8.4 Hz), 7.94 (d, 2H, J=8.4 Hz), 11.78 (s, 1H), 12.80 (brs, 1H)

Synthesis Example 41
4-{2-[5-(7-Phenoxybenzofuran-2-yl)pyrroylyl]}benzoic Acid The title compound was obtained by the same procedure as the one of Synthesis Example 1.

$^1$H-NMR (DMSO-$d_6$, 400 MHz) δ;6.56–6.59 (m, 1H), 6.79–6.84 (m, 2H), 7.07–7.21 (m, 4H), 7.25 (s, 1H), 7.37–7.44 (m, 3H), 7.87 (d, 2H, J=8.4 Hz), 7.93 (d, 2H, J=8.4 Hz), 11.91 (s, 1H), 12.82 (brs, 1H)

Synthesis Example 42
4-{2-[5-(4-Fluoro-7-chlorobenzofuran-2-yl)pyrrolyl]} benzoic Acid The title compound was obtained by the same procedure as the one of Synthesis Example 1.

$^1$H-NMR (DMSO-$d_6$, 400 MHz) δ; 6.79–6.82 (m, 1H), 6.86–6.89 (m, 1H), 7.14 (t, 1H, J=8.8 Hz), 7.37 (dd, 1H, J=4.4, 8.4 Hz), 7.38 (s, 1H), 7.90 (d, 2H, J=8.4 Hz), 7.96 (d, 2H, J=8.4 Hz), 11.97 (d, 1H), 12.86 (brs, 1H)

Synthesis Example 43
4-{2-[5-(5-Fluoro-7-chlorobenzofuran-2-yl)pyrrolyl]} benzoic Acid The title compound was obtained by the same procedure as the one of Synthesis Example 1.

$^1$H-NMR (DMSO-$d_6$, 400 MHz) δ; 6.76–6.80 (m, 1H), 6.84–6.88 (m, 1H), 7.29 (s, .1H), 7.34 (dd, 1H, J=2.4, 8.4 Hz), 7.51 (dd, 1H, J=2.4, 8.4 Hz), 7.90 (d, 2H, J=8.4 Hz), 7.96 (d, 2H, J=8.4 Hz), 12.00 (s, 1H), 12.86 (brs, 1H)

Synthesis Example 44
4-{2-[5-(7-Trifluoromethylbenzofuran-2-yl )pyrrolyl]} benzoic Acid The title compound was obtained by the same procedure as the one of Synthesis Example 1.

$^1$H-NMR (DMSO-$d_6$, 400 MHz) δ; 6.72–6.75 (m, 1H), 6.85–6.88 (m, 1H), 7.35 (s, 1H), 7.40 (t, 1H, J=7.6 Hz), 7.56 (d, 1H, J=7.6 Hz), 7.89 (d, 2H, J=8.4 Hz), 7.96 (d, 2H, J=8.4 Hz), 11.98 (s, 1H), 12.83 (brs, 1H)

Synthesis Example 45
4-{2-[5-(5,7-Dichlorobenzofuran-2-yl)pyrrolyl]}benzoic Acid The title compound was obtained by the same procedure as the one of Synthesis Example 1.

$^1$H-NMR (DMSO-$d_6$, 400 MHz) δ; 6.76–6.81 (m, 1H), 6.84–6.89 (m, 1H), 7.28 (s, 1H), 7.46 (d, 1H, J=2.0 Hz), 7.76 (d, 1H, J=2.0 Hz), 7.89 (d, 2H, J=8.4 Hz), 7.95 (d, 2H, J=8.4 Hz), 12.00 (brs, 1H)

Synthesis Example 46
4-{2-[5(4,7-Dichloro-3-methylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 2.56 (s, 3H), 6.69–6.73 (m, 1H), 6.89–6.93 (m, 1H), 7.30 (d, 1H, J=8.8 Hz), 7.39 (d, 1H, J=8.8 Hz), 7.94 (s, 4H), 11.97 (brs, 1H), 12.82 (brs, 1H)

Synthesis Example 47
4-{2-[5-(3,4 7-Trimethylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 2.50 (s, 3H), 2.53 (s, 3H), 2.59 (s, 3H), 6.57 (brs, 1H), 6.82–6.88 (m, 2H), 6.94 (d, 1H, J=7.2 Hz), 7.90 (s, 4H), 11.70 (brs, 1H), 12.80 (brs, 1H)

Synthesis Example 48
4-{2-[5-(7-Isopropylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 1.36 (d, 6H J=7.6 Hz), 3.45 (quint, 1H, J=7.6 Hz), 6.70–6.73 (m, 1H), 6.83–6.86 (m, 1H), 7.09–7.16 (m, 2H), 7.17 (s, 1H), 7.43 (d, 1H, J=7.6 Hz), 7.88 (d, 2H, J=8.4 Hz), 7.95 (d, 2H, J=8.4 Hz), 11.83 (s, 1H), 12.82 (brs, 1H)

Synthesis Example 49
4-{2-[5-(4,6-Dimethylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 2.35 (s, 3H), 2.43 (s, 3H), 6.65–6.68 (m, 1H), 6.81–6.84 (m, 1H), 6.87 (brs, 1H), 7.16–7.21 (m, 2H), 7.88 (d, 2H, J=8.4 Hz), 7.93 (d, 2H, J=8.4 Hz), 11.82 (s, 1H), 12.79 (brs, 1H)

Synthesis Example 50
4-{2-[5-(5,7-Dimethylbenzofuran-2-yl)pyrrolyl]}benzoic Acid The title compound was obtained by the same procedure as the one of Synthesis Example 1.

$^1$H-NMR (DMSO-$d_6$, 400 MHz) δ; 2.32 (s, 3H), 2.45 (s, 3H), 6.68–6.71 (m, 1H), 6.80–6.83 (m, 1H), 6.88 (d, 1H, J=1.2 Hz), 7.10 (s, 1H), 7.20 (d, 1H, J=1.2 Hz), 7.86 (d, 2H, J=8.4 Hz), 7.93 (d, 2H, J=8.4 Hz), 11.78 (s, 1H), 12.80 (brs, 1H)

Synthesis Example 51
4-{2-[5-(4-Methoxy-7-methylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 2.41 (s, 3H), 3.86 (s, 3H), 6.66–6.70 (m, 2H), 6.81–6.85 (m, 1H), 6.99 (d, 1H, J=7.6 Hz), 7.24 (s, 1H), 7.88 (d, 2H, J=8.4 Hz), 7.94 (d, 2H, J=8.4 Hz), 11.75 (s, 1H), 12.80 (brs, 1H)

Synthesis Example 52
4-{2-[5-(7-Ethoxybenzofuran-2-yl)pyrrolyl]}benzoic Acid The title compound was obtained by the same procedure as the one of Synthesis Example 1.

$^1$H-NMR (DMSO-d$_6$, 400 MHz) δ; 1.40 (t, 3H, J=7.6 Hz), 4.25 (q, 2H, J=7.6 Hz), 6.68–6.71 (m, 1H), 6.81–6.84 (m, 1H), 6.87 (d, 1H, J=7.6 Hz), 7.12 (t, 1H, J=7.6 Hz), 7.16–7.19 (m, 2H), 7.89 (d, 2H, J=8.4 Hz), 7.94 (d, 2H, J=8.4 Hz), 11.87 (s, 1H), 12.78 (brs, 1H)

Synthesis Example 53
4-{2-[5-(7-Chloro-4-methylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 6.73–6.76 (m, 1H), 6.84–6.87 (m, 1H), 7.05 (d, 1H, J=8.0 Hz), 7.22 (d, 1H, J=8.0 Hz), 7.33 (s, 1H), 7.90 (d, 2H, J=8.4 Hz), 7.95 (d, 2H, J=8.4 Hz), 11.93 (s, 1H), 12.88 (brs, 1H)

Synthesis Example 54
4-{2-[5-(7-Methoxybenzofuran-2-yl)pyrrolyl]}benzoic Acid The title compound was obtained by the same procedure as the one of Synthesis Example 1.

$^1$H-NMR (DMSO-d$_6$, 400 MHz) δ; 3.93 (s, 3H), 6.68–6.71 (m, 1H), 6.81–6.84 (m, 1H), 6.88 (dd, 1H, J=1.2, 8.0 Hz), 7.14 (t, 1H, J=8.0 Hz), 7.18 (s, 1H), 7.19 (dd, 1H, J=1.2, 8.0 Hz), 7.89 (d, 2H, J=8.4 Hz), 7.94 (d, 2H, J=8.4 Hz), 11.87 (s, 1H), 12.84 (brs, 1H)

Synthesis Example 55
4-{2-[5-(7-Ethylbenzofuran-2-yl)pyrrolyl]}benzoic Acid

The title compound was obtained by the same procedure as the one of Synthesis Example 1.

$^1$H-NMR (DMSO-d$_6$, 400 MHz) δ; 1.30 (t, 3H, J=7.6 Hz), 2.90 (q, 2H, J=7.6 Hz), 6.70–6.73 (m, 1H), 6.82–6.85 (mn, 1H), 7.08 (dd, 1H, J=0.8, 8.0 Hz), 7.14 (t, 1H, JJ=8.0 Hz), 7.44 (dd, 1H, J=0.8, 8.0 Hz) 27.88 (d, 2H, J=8.4 Hz), 7.94 (d, 2H, J=8.4 Hz), 11.82 (s, 1H), 12.83 (brs, 1H)

Synthesis Example 56
4-{2-[5-(7-Phenylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 6.68–6.71 (m, 1H), 6.83–6.86 (m, 1H), 7.28 (s, 1H), 7.32 (t, 1H, J=7.6 Hz), 7.40–7.48 (m, 2H), 7.56 (t, 2H, J=7.6 Hz) 7.63 (d, 1H, J=7.6 Hz), 7.88 (d, 2H, J=8.4 Hz), 7.92–7.98 (m, 4H), 11.90 (s, 1H), 12.84 (brs, 1H)

Synthesis Example 57
4-{2-[5-(7-Methylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 2.52 (s, 3H), 6.71–6.74 (m, 1H), 6.83–6.86 (m, 1H), 7.06, (d, 1H, J=7.2 Hz), 7.12 (t, 1H, J=7.2 Hz) 7.18 (s, 1H)7.43 (d,, 1H, J=7.2 Hz), 7.898 (d, 2 H, J=8.4 Hz), 7.95 (d, 2H, J=48.4 Hz), 11.83 (s, 1H), 12.82 (brs, 1H)

Synthesis Example 58
4-{2-[5-(4,5-Dimethylbenzofuran-2-yl)pyrrolyl]}benzoic Acid The title compound was obtained by the same procedure as the one of Synthesis Example 1.

$^1$H-NMR (DMSO-d$_6$, 400 MHz);2.34 (s, 3H), 2.46 (s, 3H), 6.70 (dd, 1H, J=2.4, 3.6 Hz), 6.83 (dd, 1H, J=2.4, 3.6 Hz), 7.11 (s, 1H), 7.22 (s, 1H), 7.87–7.95 (m, 4H), 11.80 (s, 1H), 12.79 (s, 1H)

Synthesis Example 59
4-{2-[5-(4-Methylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 2.51 (s, 3H), 6.72–6.73 (m, 1H), 6.84–6.85 (m, 1H), 7.06 (d, 1H, J=7.2 Hz), 7.12 (dd, 1H, J=5.2, 5.2 Hz), 7.10 (s, 1H), 7.44 (d, 1H, J=7.6 Hz), 7.89 (d, 2H, J=8.4 Hz), 7.95 (d, 2H, J=8.4 Hz)

Synthesis Example 60
4-{2-[5-(4-Chlorobenzofuran-2-yl )pyrrolyl]}benzoic Acid The title compound was obtained by the same procedure as the one of Synthesis Example 1.

$^1$H-NMR (DMSO-d$_6$, 400 MHz) δ; 6.78–6.80 (m, 1H), 6.86–6.87 (m, 1H), 7.24–7.33 (m, 3H), 7.57 (d, 1H, J=8.0 Hz), 7.92 (d, 2H, J=8.4 Hz), 7.95 (d, 2H, J=8.4 Hz), 11.97 (s, 1H), 12.87 (brs, 1H)

Synthesis Example 61
4-{2-[5-(5-Chlorobenzofuran-2-yl)pyrrolyl]}benzoic Acid The title compound was obtained by the same procedure as the one of Synthesis Example 1.

$^1$H-NMR (DMSO-d$_6$, 400 MHz) δ; 6.74–6.75 (m, 1H), 6.82–6.84 (m, 1H), 7.20 (s, 1H), 7.25 (dd, 1H, J=2.0, 8.4 Hz), 7.58 (d, 1H, J=8.8 Hz), 7.73 (d, 1H, J=2.0 Hz), 7.87 (brd, 2H, J=8.4 Hz), 7.94 (brd, 2H, J=8.4 Hz)

Synthesis Example 62
4-{2-[5-(4,7-methylbenzofuran-2-yl)furyl]}benzoic Acid

The title compound was obtained by the same procedure as the one of Synthesis Example 1.

$^1$H-NMR (DMSO-d$_6$, 400 MHz) δ;2.46 (s, 6H), 6.97 (d, 1H, J=7.6 Hz), 7.04 (d, 1H, J=7.6 Hz), 7.11 (d, 1H, J=4.0 Hz), 7.35 (d, 1H, J=4.0 Hz), 7.40 (s, 1H), 7.95 (d, 2H, J=8.4 Hz), 8.01 (d, 2H, J=8.4 Hz)

Synthesis Example 63
4-{2-[5-(4,7-Dimethylbenzofuran-2-yl)thienyl]}benzoic Acid The title compound was obtained by the same procedure as the one of Synthesis Example 1.

$^1$H-NMR (DMSO-d$_6$, 400 MHz) δ; 2.42 (s, 6H), 6.96 (d, 1H, J=7.2 Hz), 7.02 (d, 1H, J=7.2 Hz), 7.38 (s, 1H), 7.68 (d, 1H, J=4.0 Hz), 7.76 (d, 1H, J=4.0 Hz), 7.85 (d, 2H, J=7.6 Hz), 7.98 (d, 2H, J=7.6 Hz)

Synthesis Example 64
4-{2-[5-(4,7-Dichlorobenzofuran-2-yl)furyl]}benzoic Acid The title compound was obtained by the same procedure as the one of Synthesis Example 1.

$^1$H-NMR (DMSO-d$_6$, 400 MHz) δ; 7.30 (d, 1H, J=3.6 Hz), 7.38–7.42 (m, 2H), 7.47 (d, 1H, J=8.0 Hz), 7.52 (s, 1H), 7.97–8.03 (m, 4H)

Synthesis Example 65
4-{2-[5-(4,7-Dichlorobenzofuran-2-thienyl]}benzoic Acid The title compound was obtained by the same procedure as the one of Synthesis Example 1.

$^1$H-NMR (DMSO-d$_6$, 400 MHz) δ; 7.39 (d, 1H, J=8.0 Hz), 7.45 (d, 1H, J=8.0 Hz), 7.55 (s, 1H), 7.80 (d, 1H, J=4.4 Hz), 7.84–7.90 (m, 3H), 7.98 (d, 2H, J=8.4 Hz)

Synthesis Example 66
5-{2-[5-(4,7-Dimethylbenzofuran-2-yl)pyrrolyl]}thiophene-2-carboxylic Acid The title compound was obtained by the same procedure as the one of Synthesis Example 1.

$^1$H-NMR (DMSO-d$_6$, 400 MHz) δ; 2.43 (s, 3H), 2.45 (s, 3H) 6.62–6.65 (m, 1H), 6.66–6.69 (m, 1H), 6.92 (d, 1H, J=7.6 Hz), 6.96 (d, 1H, J=7.6 Hz), 7.19 (s, 1H), 7.45 (d, 1H, J=3.6 Hz), 7.67 (d, 1H, J=3.6 Hz), 11.96 (brs, 1H), 12.97 (brs, 1H)

Synthesis-Example 67
4-{2-[5-(2,3,4,7-Tetramethylbenzofuran-5-yl)pyrrolyl]}benzoic Acid The title compound was obtained by the same procedure as the one of Synthesis Example 1.

$^1$H-NMR (DMSO-d$_6$, 400 MHz) δ; 2.28 (s, 3H), 2.35 (s, 3H), 2.37 (s, 3H), 2.57 (s, 3H), 6.16 (brs, 1H), 6.75 (brs, 1H), 7.06 (s, 1H), 7.80 (d, 2H, J=8.4 Hz), 7.86 (d, 2H, J=8.4 Hz), 11.36 (brs, 1H), 12.69 (brs, 1H)

Synthesis Example 68
4-{2-[5-(2,3-Dimethylbenzofuran-5-yl)pyrrolyl]}benzoic Acid The title compound was obtained by the same procedure as the one of Synthesis Example 1.

$^1$H-NMR (DMSO-d$_6$, 400 MHz) δ; 2.18 (s, 3H) 2.35 (s, 3H) 6.59 (brs, 1H), 6.73 (brs, 1H), 7.42 (d, 1H, J=8.2 Hz), 7.61 (dd, 1H, J=2.0, 8.2 Hz), 7.82–7.94 (m, 5H), 11.36 (brs, 1H), 12.76 (brs, 1H)

Synthesis Example 69
4-{2-[5-(7-Chlorobenzothiophen-2-yl)pyrrolyl]}benzoic Acid The title compound was obtained by the same procedure as the one of Synthesis Example 1.

$^1$H-NMR (DMSO-d$_6$, 400 MHz) δ; 6.65–6.68 (m, 1H) 6.80–6.83 (m, 1H), 7.38–7.42 (m, 2H), 7.76–7.82 (m, 1H), 7.80 (s, 1H), 7.89 (d, 2H, J=8.4 Hz), 7.94 (d, 2H, J=8.4 Hz), 11.87 (s, 1H), 12.82 (brs, 5H)

Synthesis Example 70
4-{2-[5-(5,7-Dimethylbenzothiophen-2-yl)pyrrolyl]} benzoic Acid The title compound was obtained by the same procedure as the one of Synthesis Example 1.

$^1$H-NMR (DMSO-d$_6$, 400 MHz) δ; 6.6 (s, 3H), 2.42 (s, 3H), 6.54–6.56 (m, 1H), 6.77–6.79 (m, 1H), 6.96 (s, 1H), 7.43 (s, 1H), 7.71 (s, 1H), 7.88 (d, 2H, J=8.4 Hz), 7.93 (d, 2H, J=8.4 Hz), 11.76 (s, 8H), 12.76 (brs, 1H)

Synthesis Example 71
4-{2-[5-(7-n-Propylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 9.36 (t, 3H, J=7.2 Hz), 1.75 (sext, 2H, J=7.2 Hz), 2.78 (t, 2H, J=7.2 Hz), 6.56–6.59 (m, 1H), 6.78–6.81 (m, 1H), 7.13 (d, 1H, J=7.2 Hz), 7.30 (t, 1H, J=7.2 Hz), 7.63 (d, 1H, J=7.2HZ), 7.78 (s, 1H), 7.89 (d, 2H, J=8.4 Hz), 7.93 (d, 2H, J=8.4 Hz), 11.77 (s, 1H), 12.78 (brs, 1H)

Synthesis Example 72
4-{2-[5-(5-Fluoro-7-methylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 3.32 (s, 3H), 6.59–6.62 (m, 1H), 6.79–6.82 (m, 1H), 7.05 (dd, 1H, J=2.4, 9.0 Hz), 7.48 (dd, 1H, J=2.4, 9.0 Hz), 7.77 (s, 1H), 7.89 (d, 2H, J=8.4 Hz), 7.94 (d, 2H, J=8.4 Hz), 11.85 (s, 1H), 12.78 (brs, 1H)

Synthesis Example 73
4-{2-[5-(5-Chloro-7-methylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 3.30 (s, 3H), 6.60–6.62 (m, 1H), 6.79–6.82 (m, 1H), 7.19 (d, 1H, J=1.6 Hz), 7.73 (d, 1H, J=1.6 Hz), 7.75 (s, 1H), 7.88 (d, 2H, J=8.4 Hz), 7.94 (d, 2H, J=8.4 Hz), 11.86 (s, 1H), 12.80 (brs, 1H)

Synthesis Example 74
4-{2-[5-(7-Eethylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 1.32 (t, 3H, J=7.6 Hz), 2.82 (q, 2H, J=7.6 Hz), 6.57–6.59 (m, 1H), 6.78–6.81 (m, 1H), 7.15 (d, 1H, J=7.6 Hz), 7.31 (t, 1H, J=7.6 Hz), 7.64 (d, 1H, J=7.6 Hz), 7.79 (s, 1H), 7.89 (d, 2H, J=8.4 Hz), 7.94 (d, 2H, J=8.4 Hz), 11.78 (s, 1H), 12.83 (brs, 1H)

Synthesis Example 75
4-{2-[5-(7-Chloro-4-methylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 2.56 (s, 3H), 6.65–6.67 (m, 1H), 6.80–6.83 (m, 1H), 7.20 (d, 1H, J=7.6 Hz), 7.29 (d, 1H, J=7.6 Hz), 7.89 (d, 2H, J=8.4 Hz), 7.93 (s, 1H), 7.95 (d, 2H, J=8.4 Hz), 11.83 (s, 1H), 12.82 (brs, 1H)

Synthesis Example 76
4-{2-[5-(7-Isopropylbenzothiophen-2-yl)pyrrolyl]}benzoic Acid The title compound was obtained by the same procedure as the one of Synthesis Example 1.

$^1$H-NMR (DMSO-d$_6$, 400 MHz) δ; 1.33 (d, 6H, J=7.6 Hz), 3.10 (quint, 1H, J=7.6 Hz), 6.56–6.59 (m, 1H), 6.78–6.81 (m, 1H), 7.20 (d, 1H, J=7.6 Hz), 7.33 (t, 1H, J=7.6 Hz), 7.63 (d, 1H, J=7.6 Hz), 7.78 (s, 1H), 7.89 (d, 2H, J=8.4 Hz), 7.94 (d, 2H, J=8.4 Hz), 11.78 (s, 1H), 12.82 (brs, 1H)

Synthesis Example 77
4-{2-[5-(4,7-Dimethylbenzothiophen-2-yl)pyrrolyl]} benzoic Acid The title compound was obtained by the same procedure as the one of Synthesis Example 1.

$^1$H-NMR (DMSO-d$_6$, 400 MHz) δ; 2.42 (s, 3H), 2. 54 (s, 3H), 6.56–6.59 (m, 1H), 6.78–6.81 (m, 1H), 7.02 (d, 1H, J=6.8 Hz), 7.08 (d, 1H, J=6.8 Hz), 7.89 (s, 1H), 7.90 (d, 2H, J=8.4 Hz), 7.94 (d, 2H, J=8.4 Hz), 11.76 (s, 1H), 12.83 (brs, 1H)

Synthesis Example 78
4-{2-[5-(4,7-Dichlorobenzothiophen-2-yl)pyrrolyl]} benzoic Acid The title compound was obtained by the same procedure as the one of Synthesis Example 1.

$^1$H-NMR (DMSO-d$_6$, 400 MHz) δ; 6.76 (m, 1H) 6. 82–6.85 (m, 1H), 7.41 (d, 1H, J=8.0 Hz), 7.49 (d, 1H, J=8.0 Hz), 7.91 (d, 2H, J=8.4 Hz), 7.96 (d, 2H, J=8.4 Hz), 7.98 (s, 1H), 11.98 (s, 1H), 12.86 (brs, 1H)

Synthesis Example 79
4-{2-[5-(3,4,7-Trimethylbenzothiophen-2-yl)pyrrolyl]}benzoic Acid The title compound was obtained by the same procedure as the one of Synthesis Example 1.
$^1$H-NMR (DMSO-$d_6$, 400 MHz) δ; 2.40 (s, 3H), 2.66 (s, 3H), 2.72 (s, 3H), 6.38–6.41 (m, 1H), 6.79–6.82 (m, 1H), 6.94–7.10 (m, 2H), 7.78–7.96 (m, 4H), 11.65 (s, 1H)

Synthesis Example 80
4-{2-[5-(8-Methoxymethylnaphthalen-2-yl)pyrrolyl]} benzoic Acid The title compound was obtained by the same procedure as the one of Synthesis Example 1.
$^1$H-NMR (DMSO-$d_6$, 400 MHz) δ; 3.41 (s, 3H), 4.97 (s, 2H), 6.81 (m, 1H), 6.83 (m, 1H), 7.40 (t, 1H, J=7.6 Hz), 7.50 (d, 1H, J=6.8 Hz), 7.81 (d, 1H, J=8.0 Hz), 7.90–7.97 (m, 6H), 8.34 (s, 1H), 11.63 (s, 1H), 12.83 (brs, 1H)

Synthesis Example 81
4-{2-[5-(5,7-Dimethylbenzothiophen-2-yl)pyrrolyl]} benzoic Acid The title compound was obtained by the same procedure as the one of Synthesis Example 1.
$^1$H-NMR (DMSO-$d_6$, 400 MHz) δ; 1.51 (t, 3H, J=6.8 Hz), 4.26 (q, 2H, J=6.8 Hz), 6.73 (m, 1H), 6.83 (m, 1H), 6.95 (d, 1H, J=7.6 Hz), 7.34 (t, 1H, J=8.0 Hz), 7.41 (d, 1H, J=8.0 Hz), 7.86 (d, 1H, J=8.8 Hz), 7.92–7.95 (m, 5H), 8.48 (s, 1H), 11.70 (s, 1H)

Synthesis Example 82
4-{2-[5-(8-Isopropoxynaphthalen-2-yl)pyrrolyl]}benzoic Acid The title compound was obtained by the same procedure as the one of Synthesis Example 1.
$^1$H-NMR (DMSO-$d_6$, 400 MHz) δ; 1.43 (d, 6H, J=6.0 Hz), 4.82 (quint, 1H, J=6.0 Hz), 6.71 (m, 1H), 6.82 (m, 1H), 7.33 (t, 1H, J=8.0 Hz), 7.39 (d, 1H, J=7.6 Hz), 7.85 (d, 1H, J=8.8 Hz), 7.93 (m, 5H), 8.44 (s, 1H), 11.70 (s, 1H)

Synthesis Example 83
4-{2-[5-(8-Methoxynaphthalen-2-yl)pyrrolyl]}benzoic Acid The title compound was obtained by the same procedure as the one of Synthesis Example 1.
$^1$H-NMR (DMSO-$d_6$, 400 MHz) δ; 4.01 (s, 3H), 6.76 (m, 1H), 6.82 (m, 1H), 6.97 (d, 1H, J=7.6 Hz), 7.36 (t, 1H, J=8.0 Hz), 7.42 (d, 1H, J=8.0 Hz), 7.85 (d, 1H, J=8.8 Hz), 7.90–7.96 (m, 5H), 8.55 (s, 1H), 11.69 (s, 1H)

Synthesis Example 84
4-{2-[5-(8-(2-Furyl)naphthalen-2-yl)pyrrolyl]}benzoic Acid

The title compound was obtained by the same procedure as the one of Synthesis Example 1.
$^1$H-NMR (DMSO-$d_6$, 400 MHz) δ; 6.72 (dd, 1H, J=2.0, 3.6 Hz), 6.75 (dd, 1H, J=1.6, 3.2 Hz), 6.83 (dd, 1H, J=2.0, 3.6 Hz), 7.05 (d, 1H, J=3.2 Hz), 7.50 (t, 1H, J=8.0 Hz), 7.74 (dd, 1H, J=1.2, 7.2 Hz), 7.88–7.94 (m, 5H), 8.01 (s, 2H), 8.62 (s, 1H), 11.70 (s, 1H)

Synthesis Example 85
4-{2-[5-(7-Hydroxy-8-isopropenylnaphthalen-2-yl) pyrrolyl]}benzoic Acid The title compound was obtained by the same procedure as the one of Synthesis Example 1.
$^1$H-NMR (DMSO-$d_6$, 400 MHz) δ; 2.10 (s, 3H), 4.89 (m, 1H), 5.49 (m, 1H), 6.61 (dd, 1H, J=2.4, 4.0 Hz), 6.79 (dd, 1H, J=2.4, 3.6 Hz), 7.09 (dd, 1H, J=2.0, 8.4 Hz), 7.64 (d, 1H, J=9.2 Hz), 7.71 (d, 1H, J=8.8 Hz), 7.89 (d, 2H, J=8.4 Hz), 7.92 (d, 2H, J=8.4 Hz), 8.01 (s, 1H), 9.40 (s, 1H), 11.66 (s, 1H)

Synthesis Example 86
4-{2-[5-(8-(1Methoxyethyl)naphthalen-2-yl)pyrrolyl]} benzoic Acid The title compound was obtained by the same procedure as the one of Synthesis Example 1.
$^1$H-NMR (DMSO-$d_6$, 400 MHz) δ; 1.50 (d, 3H, J=6.0 Hz), 3.24 (s, 3H), 5.32 (q, 1H, J=6.4 Hz), 6.82 (s, 2H), 7.45 (t, 1H, J=7.6 Hz), 7.53 (d, 1H, J=6.8 Hz), 7.78 (d, 1H, J=7.6 Hz), 7.89–7.97 (m, 6H), 8.41 (s, 1H), 11.58 (s, 1H)

Synthesis Example 87
4-{2-[5-(8-(2-Thienyl)naphthalen-2-yl)pyrrolyl]}benzoic Acid The title compound was obtained by the same procedure as the one of Synthesis Example 1.
$^1$H-NMR (DMSO-$d_6$, 400 MHz) δ; 6.62 (m, 1H), 6.81 (m, 1H), 7.29 (m, 1H), 7.45 (m, 1H), 7.49 (t, 1H, J=7.6 Hz), 7.57 (d, 1H, J=7.2 Hz), 7.73 (m, 1H), 7.85–7.94 (m, 5H), 8.03 (s, 2H), 8.47 (s, 1H), 11.66 (s, 1H)

Synthesis Example 88
4-{2-[5-(5-Methoxy-8-isopropylnaphthalen-2-yl)pyrrolyl]} benzoic Acid The title compound was obtained by the same procedure as the one of Synthesis Example 1.
$^1$H-NMR (DMSO-$d_6$, 400 MHz) δ; 2.20 (s, 3H), 3.96 (s, 3H), 5.04 (s, 1H), 5.42 (s, 1H), 6.70 (m, 1H), 6.81 (m, 1H), 6.87 (d, 1H, J=8.0 Hz), 7.24 (d, 1H, J=8.0 Hz), 7.88–7.96 (m, 5H), 8.19 (m, 2H), 11.66 (s, 1H)

Synthesis Example 89
4-{2-[5-(5-Methoxy-8-isopropylnaphthalen-2-yl)pyrrolyl]} benzoic Acid The title compound was obtained by the same procedure as the one of Synthesis Example 1.
$^1$H-NMR (DMSO-$d_6$, 400 MHz); 1.33 (d, 6H, J=6.8 Hz), 3.85 (quint, 1H, J=6.8 Hz), 3.93 (s, 3H), 6.82 (s, 2H), 6.86 (d, 1H, J=8.0 Hz), 7.32 (d, 1H, J=8.0 Hz), 7.86–7.96 (m, 5H), 8.16 (d, 1H, J=8.4 Hz), 8.41 (s, 1H), 11.62 (s, 1H)

Synthesis Example 90
4-{2-[5-(5-Methoxy-8-ethylnaphthalen-2-yl)pyrrolyl]} benzoic Acid The title compound was obtained by the same procedure as the one of Synthesis Example 1.
$^1$H-NMR (DMSO-$d_6$, 400 MHz) δ; 1.31 (t, 3H, J=7.2 Hz) 3.09 (q, 2H, J=7.2 Hz), 3.93 (s, 3H), 6.80–6.84 (m, 3H), 7.25 (d, 1H, J=8.0 Hz), 7.88–7.96 (m, 5H), 8.15 (d, 1H, J=8.8 Hz), 8.33 (s, 1H)

Synthesis Example 91
4-{2-[5-(5-Methoxy-8-methylnaphthalen-2-yl)pyrrolyl]} benzoic Acid The title compound was obtained by the same procedure as the one of Synthesis Example 1.
$^1$H-NMR (DMSO-$d_6$, 400 MHz) δ; 2.63 (s, 3H), 3.92 (s, 3H) 6.77–6.82 (m, 3H), 7.24 (d, 1H, J=8.0 Hz), 7.86–7.95 (m, 5H), 8.13 (d, 1H, J=8.8 Hz), 8.28 (s, 1H), 11.62 (s, 1H)

Synthesis Example 92
4-{2-[5-(7-Chloro-5-methoxybenzofuran-2-yl)pyrrolyl]} benzoic Acid The title compound was obtained by the same procedure as the one of Synthesis Example 1.
$^1$H-NMR (DMSO-$d_6$, 400 MHz) δ; 3.80 (s, 3H), 6.72–6.75 (m, 1H), 6.84–6.86 (m, 1H), 6.95 (d, 1H, J=2.0 Hz), 7.18 (d, 1H, J=2.4 Hz), 7.22 (s, 1H), 7.89 (d, 2H, J=8.4 Hz), 7.95 (d, 2H, J=8.4 Hz), 11.94 (brs, 1H)

Synthesis Example 93
4-{2-[5-(5-Chloro-5-methylbenzofuran-2-yl)pyrrolyl]} benzoic Acid The title compound was obtained by the same procedure as the one of Synthesis Example 1.

¹H-NMR (DMSO-d₆, 400 MHz) δ;2.37 (s, 3H), 6.71–6.75 (m, 1H) 6.83–6.87 (m, 1H), 7.17 (d, 1H, J=0.4 Hz), 7.21 (s, 1H), 7.40 (d, 1H, J=0.4 Hz), 7.89 (d, 2H, J=8.4 Hz), 7.95 (d, 2H, J=8.8 Hz), 11.93 (brs, 1H)

Synthesis Example 94
4-{2-[5-(7-Chloro-5-ethylbenzofuran-2-yl)pyrrolyl]} benzoic Acid The title compound was obtained by the same procedure as the one of Synthesis Example 1.

¹H-NMR (DMSO-d₆, 400 MHz) δ; 1.22 (d, 3H, J=7.5 Hz) 2.67 (q, 2H, J=7.5 Hz), 6.73 (dd, 1H, J=2.4, 3.6 Hz), 6.85 (dd, 1H, J=2.8, 3.2 Hz), 7.18–7.19 (m, 1H), 7.23 (s, 1H), 7.43–7.44 (m, 1H), 7.89 (d, 2H, J=8.4 Hz), 7.95 (d, 2H, J=8.8 Hz), 11.93 (brs, 1H)

Synthesis Example 95
4-{2-[5-(7-Chloro-4,5-methylbenzofuran-2-yl)pyrrolyl]} benzoic Acid The title compound was obtained by the same procedure as the one of Synthesis Example 1.

¹H-NMR (DMSO-d₆, 400 MHz) δ; 2.29 (s, 3H), 2.36 (s, 3H), 6.70–6.74 (m, 1H), 6.82–6.86 (m, 1H), 7.15 (s, 1H), 7.31 (s, 1H), 7.89 (d, 2H, J=7.6 Hz), 7.95 (d, 2H, J=7.6 Hz), 11.91 (brs, 1H)

Synthesis Example 96
4-{2-[5-(5-Chloro-5-methylbenzofuran-2-yl)pyrrolyl]} benzoic Acid The title compound was obtained by the same procedure as the one of Synthesis Example 1.

¹H-NMR (DMSO-d₆, 400 MHz) δ;1.21 (t, 3H, J=7.6 Hz), 6.63 (q, 2H, J=7.6 Hz), 6.67–6.72 (m, 1H), 6.80–6.85 (m, 1H), 6.88–6.93 (m, 1H), 7.12 (s, 1H), 7.22–7.26 (m, 1H), 7.88 (d, 2H, J=8.4 Hz), 7.94 (d, 2H, J=8.4 Hz), 11.80 (brs, 1H)

Synthesis Example 97
4-{2-[5-(7-Chloro-5-isopropylbenzofuran-2-yl)pyrrolyl]} benzoic Acid The title compound was obtained by the same procedure as the one of Synthesis Example 1.

¹H-NMR (DMSO-d₆, 400 MHz) δ; 2.16 (s, 3H), 5.13–5.14 (m, 1H), 5.47–5.48 (m, 1H), 6.74–6.78 (m, 1H), 6.84–6.88 (m, 1H), 7.28 (s, 1H), 7.47 (d, 1H, J=1.6 Hz), 7.73 (d, 1H, J=1.6 Hz), 7.90 (d, 2H, J=8.4 Hz), 7.95 (d, 2H, J=8.8 Hz), 11.97 (brs, 1H)

Synthesis Example 98
4-{2-[5-(5,7-Dichloro-3-methylbenzofuran-2-yl)pyrrolyl]} benzoic acid The title compound was obtained by the same procedure as the one of Synthesis Example 1.

¹H-NMR (DMSO-d₆, 400 MHz) δ; 2.35 (s, 3H), 6.66–6.70 (m, 1H), 6.80–6.84 (m, 1H), 7.45–7.49 (m, 1H), 7.68–7.72 (m, 1H), 7.80–7.90 (m, 4H), 11.84 (brs, 1H)

Synthesis Example 99
4-{2-[5-(7-Chloro-4-ethylbenzofuran-2-yl)pyrrolyl]} benzoic Acid The title compound was obtained by the same procedure as the one of Synthesis Example 1.

¹H-NMR (DMSO-d₆, 400 MHz) δ; 1.28 (t, 3H, J=7.6 Hz), 2.83 (q, 2H, J=7.6 Hz), 6.74–6.76 (m, 1H), 6.84–6.87 (m, 2H), 7.07 (d, 1H, J=8.0 Hz), 7.25 (d, 1H, J=8.0 Hz), 7.37 (s, 1H), 7.90 (d, 2H, J=8.4 Hz), 7.95 (d, 2H, J=8.4 Hz), 11.91 (brs, 1H)

Synthesis Example 100
4-{2-[5-(4,5,7-Trimethylbenzofuran-2-yl)pyrrolyl]}benzoic Acid The title compound was obtained by the same procedure as the one of Synthesis Example 1.

¹H-NMR (DMSO-d₆, 400 MHz) δ; 2.26 (s, 3H), 2.35 (s, 3H), 2.43 (s, 3H), 6.67–6.71 (m, 1H), 6.81–6.85 (m, 1H), 6.87 (s, 1H), 7.21 (s, 1H), 7.88 (d, 2H, J=8.4 Hz), 7.94 (d, 2H, J=8.0 Hz), 11.78 (brs, 1H)

Synthesis Example 101
4-{2-[5-(6-Chloro-7-n-propylbenzofuran-2-yl)pyrrolyl]} benzoic Acid The title compound was obtained by the same procedure as the one of Synthesis Example 1.

¹H-NMR (DMSO-d₆, 400 MHz) δ; 0.96 (t, 3H, J=7.6 Hz), 1.64–1.76 (m, 2H), 2.95–3.03 (m, 2H), 6.73–6.76 (m, 1H), 6.83–6.87 (m, 1H), 7.19 (s, 1H), 7.26 (d, 1H, J=8.8 Hz), 7.47 (d, 1H, J=8.8 Hz), 7.89 (d, 2H, J=8.0 Hz), 7.96 (d, 2H, J=8.4 Hz), 11.87 (brs, 1H)

Synthesis Example 102
4-{2-[5-(4-Chloro-7-n-butylbenzofuran-2-yl)pyrrolyl]} benzoic Acid The title compound was obtained by the same procedure as the one of Synthesis Example 1.

¹H-NMR (DMSO-d₆, 400 MHz) δ; 0.92 (t, 3H, J=7.6 Hz), 1.29–1.38 (m, 2H), 1.64–1.74 (m, 2H), 2.84–2.92 (m, 2H), 6.75–6.79 (m, 1H), 6.83–6.87 ((m, 2H), 7.08 (d, 1H, J=7.7 Hz), 7.22 (d, 1H, J=7.7 Hz), 7.28 (s, 1H), 7.88 (d, 2H, J=8.8 Hz), 7.96 (d, 2H, J=8.8 Hz), 11.90 (brs, 1H)

Synthesis Example 103
4-{2-[5-(3,5-Chloro-4,7-dimethylbenzofuran-2-yl) pyrrolyl]} benzoic Acid The title compound was obtained by the same procedure as the one of Synthesis Example 1.

¹H-NMR (DMSO-d₆, 400 MHz) δ; 2.53 (s, 3H), 2.69 (s, 3H), 6.93 (dd, 1H, J=2.4, 4.0 Hz), 7.01 (dd, 1H, J=2.4, 4.0 Hz), 7.27 (s, 1H), 7.95 (s, 4H), 11.94 (brs, 1H)

Synthesis Example 104
4-{2-[5-(3-Chloro-4,7-methylbenzofuran-2-yl)pyrrolyl]} benzoic Acid (A) Methyl 4-{2-[5-(3-chloro-4,7-dimethylbenzofuran-2-yl) pyrrolyl]}benzoate Methyl 4-{2-[5-(4,7-dimethylbenzofuran-2-yl)pyrrolyl]} benzoate (0.30 g) was dissolved in N,N-dimethylformamide (10 ml). After adding N-chlorosuccinimide (0.13 g), the resultant mixture was stirred at room temperature for 14 hr. After adding ethyl acetate (30 ml) to the liquid reaction mixture, the organic layer was washed with brine and dried over anhydrous magnesium sulfate. After filtering off the desiccant, the filtrate was concentrated. The resulting crude product was purified by silica gel column chromatography and the resulting solid was washed with methanol to give the title compound (0.12 g) as pale yellow crystals.

¹H-NMR (CDCl₃, 400 MHz) δ; 2.50 (s, 3H), 2.71 (s, 3H), 3.92 (s, 3H), 6.77–6.80 (m, 1H), 6.91 (d, 1H, J=7.6 Hz), 6.98 (d, 1H, J=7.6 Hz), 7.01–7.04 (m, 1H), 7.63 (d, 2H, J=8.4 Hz), 8.08 (d, 2H, J=8.4 Hz), 9.23 (brs, 1H)

(B) 4-{2-[5-(3-Chloro-4,7-dimethylbenzofuran-2-yl) pyrrolyl]}benzoic Acid

The title compound was obtained by the same procedure as the one of Synthesis Example 1 (D).

¹H-NMR (DMSO-d₆, 400 MHz) δ; 2.52 (s, 3H), 2.65 (s, 3H) 6.90–6.93 (m, 1H), 6.95–6.99 (m, 2H), 7.04–7.08 (m, 1H), 7.95 (s, 4H), 11.89 (brs, 1H)

Synthesis Example 105
4-{2-[5-(4,7-Diethylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 1.27 (t, 3H, J=7.6 Hz), 1.30 (t, 3H, J=7.6 Hz), 2.81 (q, 2H, J=7.6 Hz), 2.88 (q, 2H, J=7.6 Hz), 6.70 (dd, 1H, J=2.4, 4.0 Hz), 6.83 (dd, 1H, J=2.8, 3.6 Hz), 6.96 (d, 1H, J=7.6 Hz), 7.01 (d, 1H, J=7.6 Hz), 7.27 (s, 1H), 7.88 (d, 2H, J=8.4 Hz), 7.94 (d, 2H, J=8.8 Hz), 11.78 (brs, 1H)

Synthesis Example 106
4-{2-[5-(5-Chloro-7-fluorobenzofuran-2-yl)pyrrolyl]} benzoic Acid The title compound was obtained by the same procedure as the one of Synthesis Example 1.

$^1$H-NMR (DMSO-d$_6$, 400 MHz) δ; 6.75–6.84 (m, 2H), 7.25 (s, 1H), 7.33 (dd, 1H, J=2.4, 8.8 Hz), 7.60 (d, 1H, J=2.4 Hz), 7.85 (d, 2H, J=8.4 Hz), 7.94 (d, 2H, J=8.4 Hz), 12.00 (s, 1H)

Synthesis Example 107
4-{2-[5-(7-Ethynylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 4.55 (s, 1H), 6.73 (dd, 1H, J=2.4, 4.0 Hz), 6.85 (dd, 1H, J=2.4, 4.0 Hz), 7.23 (t, 1H, J=8.0 Hz), 7.26 (s, 1H), 7.36 (dd, 1H, J=4.2, 8.0 Hz), 7.69 (dd, 1H, J=1.2, 8.0 Hz), 7.89 (d, 2H, J=8.4 Hz), 7.95 (d, 2H, J=8.4 Hz), 11.94 (brs, 1H)

Synthesis Example 108
4-{2-[5-(7-(2-Methoxyethyl)benzofuran-2-yl)pyrrolyl]} benzoic Acid The title compound was obtained by the same procedure as the one of Synthesis Example 1.

$^1$H-NMR (DMSO-d$_6$, 400 MHz) δ; 3.14 (t, 2H, J=7.2 Hz), 3.27 (s, 3H), 3.70 (t, 2H, J=7.2 Hz), 6.73 (dd, 1H, J=2.4, 3.6 Hz), 6.84 (dd, 1H, J=2.4, 3.6 Hz), 7.11–7.16 (m, 2H), 7.18 (s, 1H), 7.46 (dd, 1H, J=2.0, 6.8 Hz), 7.89 (d, 2H, J=8.4 Hz), 7.94 (d, 2H, J=8.4 Hz), 11.85 (s, 1H), 12.83 (brs, 1H)

Synthesis Example 109
4-{2-[5-(5-Fluoro-7-methylbenzofuran-2-yl)pyrrolyl]} benzoic Acid The title compound was obtained by the same procedure as the one of Synthesis Example 1.

$^1$H-NMR (DMSO-d$_6$, 400 MHz) δ; 2.43 (s, 3H), 6.75 (brs, 1H) 6.85 (brs, 1H), 6.93 (d, 1H, J=10.0 Hz), 7.19 (s, 1H), 7.26 (d, 1H, J=6.8 Hz), 7.89 (d, 2H, J=8.0 Hz), 7.95 (d, 2H, J=8.0 Hz), 11.90 (s, 1H)

Synthesis Example 110
4-{2-[5-(4-Fluoro-7-methylbenzofuran-2-yl)pyrrolyl]} benzoic Acid The title compound was obtained by the same procedure as the one of Synthesis Example 1.

$^1$H-NMR (DMSO-d$_6$, 400 MHz) 2.42 (s, 3H) 6.72 (brs, 1H), 6.84 (brs, 1H), 7.06 (t, 1H, J=8.0 Hz), 7.19 (s, 1H), 7.44 (dd, 1H, J=6.0, 8.0 Hz), 7.88 (d, 2H, J=8.0 Hz), 7.94 (d, 2H, J=8.0 Hz), 11.85 (brs, 1H)

Synthesis Example 111
4-{2-[5-(7-Bromo-4-fluorobenzofuran-2-yl)pyrrolyl]} benzoic Acid The title compound was obtained by the same procedure as the one of Synthesis Example 1.

$^1$H-NMR (DMSO-d$_6$, 400 MHz) δ; 6.78 (dd, 1H, J=2.4, 3.6 Hz), 6.87 (dd, 1H, J=2.4, 3.6 Hz), 7.09 (t, 1H, J=9.2 Hz), 7.48 (dd, 1H, J=4.8, 8.4 Hz), 7.49 (s, 1H), 7.93 (d, 2H, J=8.8 Hz), 7.96 (d, 2H, J=8.8 Hz), 12.20 (brs, 1H)

Synthesis Example 112
4-{2-[5-(4,7-Dimethylbenzofuran-2-yl)pyrrolyl]}pyridine-5-benzoic Acid The title compound was obtained by the same procedure as the one of Synthesis Example 1.

$^1$H-NMR (DMSO-d$_6$, 400 MHz) δ; 2.44 (s, 3H), 2.46 (s, 3H), 6.72–6.76 (m, 1H), 6.92 (d, 1H, J=8.0 Hz), 6.96 (d, 1H, J=8.0 Hz), 7.04–7.09 (m, 1H), 7.51 (s, 1H), 7.93 (d, 1H, J=7.6 Hz), 8.20 (dd, 1H, J=2.4, 7.6 Hz), 9.02 (d, 1H, J=2.4 Hz), 12.26 (brs, 1H)

Synthesis Example 113
4-{2-[5-(4,6,7-Trimethylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 2.29 (s, 3H), 2.38 (s, 3H), 2.40 (s, 3H), 6.69 (brs, 1H), 6.81–6.84 (m, 2H), 7.17 (s, 1H), 7.86–7.95 (m, 4H), 11.76 ((brs, 1H), 12.82 (brs, 1H)

Synthesis Example 114
4-{2-[5-(4,7-Dimethylbenzofuran-2-yl)pyrrolyl]}naphthoic Acid The title compound was obtained by the same procedure as the one of Synthesis Example 1.

$^1$H-NMR (DMSO-d$_6$, 400 MHz) δ; 2.46 (s, 3H), 2.47 (s, 3H), 6.73 (brd, 1H, J=3.6 Hz), 6.90 (brd, 1H, J=3.7 Hz), 6.92 (d, 1H, J=6.8 Hz), 6.96 (d, 1H, J=6.8 Hz), 7.25 (s, 1H), 7.93 (d, 1H, J=8.4 Hz), 7.97 (d, 1H, J=8.4 Hz), 8.01 (d, 1H, J=8.4 Hz), 8.10 (d, 1H, J=8.8 Hz), 8.35 (s, 1H), 8.53 (s, 1H), 11.88 (brs, 1H)

Synthesis Example 115
4-{2-[5-(4,7-Dimethylbenzofuran-1-yl)pyrrolyl]}naphthoic Acid The title compound was obtained by the same procedure as the one of Synthesis Example 1.

$^1$H-NMR (DMSO-d$_6$, 400 MHz) δ; 2.41 (s, 3H), 2.47 (s, 3H) 6.58 (t, 1H, J=3.0 Hz), 6.81 (t, 1H, J=3.0 Hz), 6.93 (ABq, 2H, J=9.0 Hz), 7.18 (s, 1H), 7.58–7.70 (m, 2H), 7.72 (d, 1H, J=9.0 Hz), 8.17 (d, 1H, J=9.0 Hz), 8.40 (d, 1H, J=9.0 Hz), 8.77 (d, 1H, J=9.0 Hz)

Synthesis Example 116
2,5-Dimethyl-4-{2-[5-(4,7-dimethylbenzofuran-2-yl) pyrrolyl]}benzoic Acid The title compound was obtained by the same procedure as the one of Synthesis Example 1.

$^1$H-NMR (DMSO-d$_6$, 400 MHz) δ; 2.41 (s, 3H), 2.42 (s, 3H), 2.47 (s, 3H), 2.55 (s, 3H), 6.48 (dd, 1H, J=2.5, 3.0 Hz), 6.71 (dd, 1H, J=2.5, 3.0 Hz), 6.92 (ABq, 2H, J=7.0 Hz), 7.18 (s, 1H), 7.46 (brs, 1H), 7.75 (brs, 1H)

Synthesis Example 117
5-{2-[5-(4,7-Dimethylbenzofuran-2-yl)pyrrolyl]}-2-furancarboxylic Acid The title compound was obtained by the same procedure as the one of Synthesis Example 1.

$^1$H-NMR (DMSO-d$_6$, 400 MHz) δ; 2.43 (s, 3H), 2.45 (s, 3H), 6.58 (d, 1H, J=3.6 Hz), 6.79 (d, 1H, J=3.6 Hz), 6.87–6.96 (m, 3H), 7.01–7.08 (brs, 1H), 7.18 (s, 1H)

Synthesis Example 118
3-{2-[5-(4,7-Dimethylbenzofuran-2-yl)pyrrolyl]}benzoic Acid The title compound was obtained by the same procedure as the one of Synthesis Example 1.

$^1$H-NMR (DMSO-d$_6$, 400 MHz) δ; 2.49 (s, 3H), 2.57 (s, 3H), 6.70 (dd, 1H, J=2.5, 3.8 Hz), 6.74 (dd, 1H, J=2.5, 3.8 Hz), 6.83 (s, 1H), 6.93 (d, 1H, J=7.5 Hz), 6.97 (d, 1H, J=7.5 Hz), 7.52 (t, 1H, J=8.0 Hz), 7.83 (d, 1H, J=7.5 Hz), 7.96 (d, 1H, J=7.5 Hz), 8.28 (s, 1H), 9.03 (brs, 1H)

Synthesis Example 119
3-Bromo-4-{2-[5-(naphtho[1,2-b]furan-2-yl)pyrrolyl]}benzoic Acid The title compound was obtained by the same procedure as the one of Synthesis Example 1.

$^1$H-NMR (DMSO-d$_6$, 400 MHz) δ; 6.86 (m, 2H), 7.31 (s, 1H), 7.51 (t, 1H, J=7.6 Hz), 7.65 (t, 1H, J=7.8 Hz), 7.75 (s, 1H), 7.79 (d, 1H, J=8.0 Hz), 7.99 (dd, 1H, J=1.2, 8.4 Hz), 8.02 (d, 1H, J=8.4HZ), 8.19 (s, 1H), 8.32 (d, 1H, J=8.0 Hz), 11.98 (brs, 1H)

Synthesis Example 120
3-Bromo-4-{2-[5-(4,7-dichlorobenzofuran-2-yl)pyrrolyl]}benzoic Acid The title compound was obtained by the same procedure as the one of Synthesis Example 1.

$_1$H-NMR (DMSO-d$_6$, 400 MHz) δ; 6.80 (d, 1H, J=3.6 Hz), 6.83 (d, 1H, J=3.6 Hz), 7.34 (dd, 1H, J=1.08.2 Hz), 7.35 (s, 1H), 7.37 (dd, 1H, J=0.6, 8.6 Hz), 7.70 (brd, 1H, J=8.4 Hz), 7.94 (brd, 1H, J=8.0 Hz), 8.16 (brs, 1H)

Synthesis Example 121
4-{2-[5-(3,4-Dimethylnaphthalen-1-yl)pyrrolyl]}benzoic Acid The title compound was obtained by the same procedure as the one of Synthesis Example 1.

$^1$H-NMR (DMSO-d$_6$, 400 MHz) δ; 2.54 (s, 3H), 2.65 (s, 3H), 6.57 (dd, 1H, J=2.8, 2.8 Hz), 6.85 (dd, 1H, J=3.2, 3.2 Hz), 7.43 (s, 1H), 7.47 (dd, 1H, J=7.6, 7.6 Hz), 7.55 (dd, 1H, J=7.2, 7.2 Hz), 7.62 (d, 1H, J=8.4 Hz), 8.11 (d, 4H, J=8.0 Hz), 8.68 (brs, 1H)

Synthesis Example 122
4-{2-[5-(5,8-Dimethylnaphthalen-2-yl)pyrrolyl]}benzoic Acid The title compound was obtained by the same procedure as the one of Synthesis Example 1.

$^1$H-NMR (DMSO-d$_6$, 400 MHz) δ; 2.61 (s, 3H), 2.67 (s, 3H) 7.23 (d, 1H, J=37.2 Hz), 7.26 (d, 1H, J=7.6 Hz), 7.64 (d, 1H, J=4.0 Hz), 7.70 (d, 2H, J 8.0 Hz), 7.73 (d, 1H, J=3.6 Hz), 7.91 (d, 3H, J=84.4 Hz) 8.06 (d, 1H, J=8.8 Hz), 8.21 (s, 1H)

Synthesis Example 123
4-{2-[5-(5,8-Dimethylnaphthalen-2-yl)furyl]}benzoic Acid

The title compound was obtained by the same procedure as the one of Synthesis Example 1.

$^1$H-NMR (DMSO-d$_6$, 400 MHz) δ; 2.61 (s, 3H), 2.70 (s, 3H), 7.24 (d, 1H, J=6.8 Hz), 7.27 (d, 1H, J=7.2 Hz), 7.33 (s, 2H), 7.97 (d, 2H, J=8.4 Hz), 8.01 (d, 3H, J=8.4 Hz), 8.07 (d, 1H, J=8.8 Hz), 8.39 (s, 1H)

Synthesis Example 124
4-{2-[5-(8-Ethyl-1-methoxynaphthalen-2-yl)pyrrolyl]}benzoic Acid The title compound was obtained by the same procedure as the one of Synthesis Example 1.

$^1$H-NMR (CDCl$_3$, 400 MHz) δ;1.36 (t, 3H, J=7.2 Hz) 3.35 (q, 2H, J=7.6 Hz), 3.74 (s, 3H), 6.77–6.81 (m, 2H), 7.30–7.40 (m, 2H), 7.60–7.73 (m, 5H), 8.10–8.20 (m, 2H), 10.34 (brs, 1H)

Synthesis Example 125
4-{2-[5-(8-Chloro-1-methoxynaphthalen-2-yl)pyrrolyl]}benzoic Acid The title compound was obtained by the same procedure as the one of Synthesis Example 1.

$^1$H-NMR (CDCl$_3$, 400 MHz) δ; 2.97 (s, 3H), 3.73 (s, 3H), 6.76–6.80 (m, 2H), 7.28–7.35 (m, 2H), 7.61–7.72 (m, 5H), 8.14 (d, 2H, J=8.4 Hz), 10.33 (brs, 1H)

Synthesis Example 126
4-{2-[5-(5-Acenaphthenyl)pyrrolyl]}benzoic Acid

The title compound was obtained by the same procedure as the one of Synthesis Example 1.

$^1$H-NMR (CDCl$_3$, 400 MHz) δ; 3.40–3.48 (m, 4H), 6.64–6.66 (m, 1H), 6.84–6.86 (m, 1H), 7.33–7.36 (m, 2H), 7.50–7.64 (m, 4H), 8.03 (d, 1H, J=8.4 Hz), 8.09–8.12 (m, 2H), 8.76 (brs, 1H)

Synthesis Example 127
4-{2-[5-(5,8-Dimethyl-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.09 (s, 3H), 2.34 (s, 3H), 4.95 (brs, 2H), 6.45–6.47 (m, 1H), 6.67 (d, 1H, J=7.6 Hz), 6.75–6.77 (m, 1H), 6.84 (d, 1H, J=7.6 Hz), 7.24 (brs, 1H), 7.85–7.94 (m, 4H)

Synthesis Example 128
4-{2-[5-(5-Isopropyl-8-methyl-2H-chromen-3-yl)pyrrolyl]}benzoic Acid The title compound was obtained by the same procedure as the one of Synthesis Example 1.

$^1$H-NMR (CDCl$_3$, 400 MHz) δ; 1.30 (d, 6H, J=6.8 Hz), 3.28 (hept., 1H, J=6.8 Hz), 4.99 (d, 2H, J=1.2 Hz), 6.39–6.40 (m, 1H), 6.71–6.73 (m, 1H), 6.81–6.86 (m, 2H), 6.99 (d, 1H, J=8.0 Hz), 7.64 (d, 2H, J=8.4 Hz), 8.13 (d, 2H, J=8.4 Hz), 8.70 (brs, 1H)

Synthesis Example 129
4-{2-[5-(5-Methyl-5H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.14 (s, 3H) 5.04 (brs, 2H) 6.43–6.45 (m, 1H), 6.75–6.77 (m, 1H), 6.81 (t, 1H, J=7.6 Hz), 6.95 (t, 1H, J=8.0 Hz), 7.09 (brs, 1H), 7.86–7.93 (m, 4H), 11.39 (s, 1H), 12.82 (brs, 1H)

Synthesis Example 130
4-{2-[5-(5-Ethyl-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 1.13 (t, 3H, J=7.2 Hz), 2.48–2.55 (m, 2H), 5.02 (brs, 2H), 6.45 (brs, 1H), 6.75–7.09 (m, 5H), 7.85–7.93 (m, 4H), 11.39 (s, 1H), 12.81 (s, 1H)

Synthesis Example 131
4-{2-[5-(5-Methoxy-5H-chromen-3-yl)pyrrolyl]}benzoic Acid The title compound was obtained by the same procedure as the one of Synthesis Example 1.

$^1$H-NMR (CDCl$_3$, 400 MHz) δ; 3.91 (s, 3H), 5.00 (brs, 2H), 6.34 (brs, 1H), 6.50–6.55 (m, 2H), 6.70 (s, 1H), 6.95 (s, 1H), 7.08 (dd, 1H, J=7.2, 7.2 Hz), 7.62 (d, 2H, J=7.6 Hz), 8.11 (d, 2H, J=8.4 Hz), 8.77 (brs, 1H)

Synthesis Example 132
4-{2-[5-(8-Methoxy-7-methyl-2H-chromen-3-yl)pyrrolyl]}benzoic Acid The title compound was obtained by the same procedure as the one of Synthesis Example 1.

$^1$H-NMR (CDCl$_3$, 400 MHz) δ; 2.16 (s, 3H), 3.73 (s, 3H), 5.01 (brs, 2H), 6.44 (m, 1H), 6.70–7.77 (m, 3H), 7.07 (s, 1H), 7.85–7.93 (m, 4H), 11.38 (brs, 1H), 12.80 (brs, 1H),

Synthesis Example 133
4-{2-[5-(4-Methyl-2H-chromen-6-yl)pyrrolyl]}benzoic Acid The title compound was obtained by the same procedure as the one of Synthesis Example 1.

$^1$H-NMR (CDCl$_3$, 400 MHz) δ; 2.10 (d, 3H, J=1.6 Hz), 4.79 (q, 2H, J=1.6 Hz), 5.65 (m, 1H), 6.51 (dd, 1H, J=2.8, 3.6 Hz), 6.74 (dd, 1H, J=2.8, 3.6 Hz), 6.85 (d, 1H, J=8.0 Hz), 7.29–7.32 (m, 2H), 7.59 (d, 2H, J=8.8 Hz), 8.10 (d, 2H, J=8.4 Hz), 8.60 (brs, 1H)

Synthesis Example 134
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 3.75 (s, 3H), 4.97 (brs, 2H) 6.53 (brs, 1H), 6.79–6.82 (m, 2H), 7.14 (d, 1H, J=8.8 Hz), 7.22 (brs, 1H), 7.91 (brs, 4H), 11.65 (brs, 1H), 12.83 (brs, 1H)

Synthesis Example 135
4-{2-[5-(8-Methoxy-5-methyl-2H-chromen-3-yl)pyrrolyl]}benzoic Acid The title compound was obtained by the same procedure as the one of Synthesis Example 1.

$^1$H-NMR (CDCl$_3$, 400 MHz) δ; 2.37 (s, 3H), 3.88 (s, 3H), 5.05 (brs, 2H), 6.40 (brs, 1H), 6.71–6.72 (m, 4H), 7.64 (d, 2H, J=7.6 Hz), 8.12 (d, 2H, J=8.0 Hz), 8.68 (brs, 1H)

Synthesis Example 136
4-{2-[5-(5-Propyl-2H-chromen-3-yl)pyrrolyl]}benzoic Acid The title compound was obtained by the same procedure as the one of Synthesis Example 1.

$^1$H-NMR (CDCl$_3$, 400 MHz) δ; 0.97 (t, 3H, J=7.2 Hz), 1.63 (tq, 2H, J=7.2, 7.2 Hz), 2.59 (t, 2H, J=7.6 Hz), 5.04 (s, 2H), 6.36 (dd, 1H, J=2.4, 2.4 Hz), 6.62 (brs, 1H), 6.86 (dd, 1H, J=7.6, 7.6 Hz), 6.94–7.01 (m, 2H), 7.61 (d, 2H, J=8.4 Hz), 8.11 (d, 2H, J=8.4 Hz), 8.63 (brs, 1H)

Synthesis Example 137
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (CDCl$_3$, 400 MHz) δ; 2.19 (s, 3H), 5.05 (d, 2H, J=1.2 Hz), 6.41 (dd, 1H, J=3.6, 3.6 Hz), 6.71 (dd, 1H, J=3.6, 3.6 Hz), 6.90 (brs, 3H), 7.64 (d, 2H, J=8.8 Hz), 8.11 (d, 1H, J=8.8 Hz), 8.74 (brs, 1H)

Synthesis Example 138
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.02 (s, 3H), 2.15 (s, 3H), 2.31 (s, 3H), 4.91 (s, 2H), 6.43 (brs, 1H), 6.60 (s, 1H), 6.75 (brs, 1H), 7.23 (s, 1H), 7.85–7.93 (m, 4H), 11.35 (s, 1H), 12.78 (brs, 1H)

Synthesis Example 139
4-{2-[5-(5,7-Bromo-8-methoxy-2H-chromen-3-yl)pyrrolyl]} benzoic Acid The title compound was obtained by the same procedure as the one of Synthesis Example 1.

$^1$H-NMR (DMSO-d$_6$, 400 MHz) δ; 2.19 (s, 3H), 2.34 (s, 3H), 4.90 (s, 2H), 6.43 (dd, 1H, J=3.2, 3.2 Hz), 6.49 (brs, 1H), 6.60 (brs, 1H), 6.75 (dd, 1H, J=3.2, 3.2 Hz), 7.23 (brs, 1H), 7.86 (d, 2H, J=8.4 Hz), 7.93 (d, 2H, J=8.8 Hz)

Synthesis Example 140
4-{2-[5-(7,8-Dimethyl-2H-chromen-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.07 (s, 3H), 2.19 (s, 3H), 5.00 (s, 2H), 6.41–6.43 (m, 1H), 6.72–6.76 (m, 2H), 6.84 (d, 1H, J=7.6 Hz), 7.06 (brs, 1H), 7.86 (d, 2H, J=8.4 Hz), 7.91 (d, 2H, J=8.8 Hz)

Synthesis Example 141
4-{2-[5-(6-Methyl-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.22 (s, 3H), 4.97 (s, 2H), 6.44 (dd, 1H, J=2.0, 2.0 Hz), 6.70 (d, 1H, J=7.6 Hz), 6.76 (dd, 1H, J=2.0, 2.0 Hz), 6.87–6.89 (m, 2H), 7.06 (s, 1H), 7.85–7.93 (m, 4H), 11.39 (s, 1H), 12.79 (brs, 1H)

Synthesis Example 142
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.10 (s, 3H), 2.19 (s, 3H), 4.99 (s, 2H), 6.44 (s, 1H), 6.73 (s, 1H), 6.77 (brs, 2H), 7.04 (s, 1H), 7.86–7.93 (m, 4H), 11.38 (s, 1H), 12.78 (brs, 1H)

Synthesis Example 143
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 5.05 (s, 2H), 6.46–6.52 (m, 1H), 6.74–6.79 (m, 1H), 6.83 (d, 1H, J=8.8 Hz), 7.05–7.10 (m, 3H), 7.86 (d, 2H, J=8.4 Hz), 7.92 (d, 2H, J=8.0 Hz), 11.47 (s, 1H), 12.80 (brs, 1H)

Synthesis Example 144
4-{2-[5-(7-Chloro-2H-chromen-3-yl)pyrrolyl]}benzoic Acid The title compound was obtained by the same procedure as the one of Synthesis Example 1.

$^1$H-NMR (DMSO-d$_6$, 400 MHz)δ; 5.06 (s, 2H), 6.47 (dd, 1H, J=2.4, 3.2 Hz), 6.77 (dd, 1H, J=2.4, 3.2 Hz), 6.91 (d, 1H, J=2.0 Hz), 6.96 (dd, 1H, J=2.0, 8.0 Hz), 7.10 (d, 1H, J=8.0 Hz), 7.10 (s, 1H), 7.87 (d, 2H, J=8.4 Hz), 7.92 (d, 2H, J=8.8 Hz), 11.44 (s, 1H), 12.81 (brs, 1H)

Synthesis Example 145
4-{2-[5-(5,6,7-Trimethyl-2H-chromen-3-yl)pyrrolyl]} benzoic Acid The title compound was obtained by the same procedure as the one of Synthesis Example 1.

$^1$H-NMR (DMSO-d$_6$, 400 MHz) δ;2.08 (s, 2H), 2.18 (s, 3H), 2.31 (s, 3H), 4.83 (s, 2H), 6.43 (dd, 1H, J=2.8, 2.8 Hz), 6.53 (s, 1H), 6.75 (dd, 1H, J=3.2, 3.2 Hz), 7.86 (d, 2H, J=8.4 Hz), 7.93 (d, 2H, J=8.0 Hz), 11.36 (s, 1H), 12.78 (brs, 1H)

Synthesis Example 146
4-{2-[5-(5-Bromo-8-methoxy-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 2.07 (s, 3H), 2.14 (s, 3H), 2.26 (s, 3H), 4.88 (s, 2H), 6.46 (dd, 1H, J=2.4, 2.4 Hz), 6.75–6.77 (m, 2H), 7.33 (s, 1H), 7.87 (d, 2H, J=8.8 Hz), 7.93 (d, 2H, J=8.4 Hz), 11.39 (s, 1H), 12.78 (brs, 1H)

Synthesis Example 147

The title compound was obtained by the same procedure as the one of Synthesis Example 1.

$^1$H-NMR (DMSO-d$_6$, 400 MHz) δ; 5.04 (brs, 2H), 6.54 (dd, 1H, J=2.8, 2.8 Hz), 6.29 (dd, 1H, J=2.8, 2.8 Hz), 6.82 (d, 1H, J=8.4 Hz), 7.02–7.10 (m, 2H), 7.37 (brs, 1H), 7.90–7.95 (m, 4H), 11.63 (s, 1H), 12.81 (brs, 1H)

Synthesis Example 148
4-{2-[5-(8-Methyl-2H-chromen-3-yl)pyrrolyl]}benzoic Acid The title compound was obtained by the same procedure as the one of Synthesis Example 1.

$^1$H-NMR (CDCl$_3$, 400 MHz) δ; 2.13 (brs, 2H), 5.03 (brs, 2H), 6.43–6.45 (m, 1H), 6.75–6.77 (m, 1H), 6.81 (dd, 1H, J=7.2, 7.2 Hz), 6.92–6.96 (m, 2H), 7.08 (brs, 1H), 7.85–7.93 (m, 4H)

Synthesis Example 149
4-{2-[5-(8-Trifluoromethyl-2H-chromen-3-yl)pyrrolyl]}benzoic Acid The title compound was obtained by the same procedure as the one of Synthesis Example 1.

$^1$H-NMR (DMSO-d$_6$, 400 MHz) δ; 5.17 (s, 2H), 6.53 (brs, 1H), 6.79 (brs, 1H), 7.07 (dd, 1H, J=7.6, 7.6 Hz), 7.16 (s, 1H), 7.36–7.38 (m, 2H), 7.86–7.94 (m, 4H), 11.49 (s, 1H), 12.80 (brs, 1H)

Synthesis Example 150
4-{2-[5-(3-Fluoro-4,7-dimethylbenzofuran-2-yl)pyrrolyl]}benzoic Acid (A) Methyl 4-{2-[5-(3-fluoro-4,7-dimethylbenzofuran-2-yl)pyrrolyl]}benzoate Methyl 4-{2-[5-(4,7-dimethylbenzofuran-2-yl)pyrrolyl]}benzoate (0.20 g) was dissolved in dry tetrahydrofuran (5 ml). After adding N-fluoro-3,5-dichloropyridinium triflate (0.20 g), the resultant mixture was stirred at room temperature for 30 min. Then the liquid reaction mixture was poured into a cold saturated aqueous solution of sodium bicarbonate. After adding ethyl acetate (50 ml), the organic layer was washed with brine and dried over anhydrous magnesium sulfate. After filtering off the desiccant, the filtrate was concentrated. The resulting crude product was purified by silica gel column chromatography to give the title compound (0.05 g) as pale yellow crystals.

$^1$H-NMR (CDCl$_3$, 400 MHz) δ; 2.48 (s, 3H), 2.60 (s, 3H), 3.94 (s, 3H), 6.75–6.79 (m, 2H), 6.92 (d, 1H, J=7.6 Hz), 6.99 (d, 1H, J=7.6 Hz), 7.62 (d, 2H, J=8.4 Hz), 8.07 (d, 2H, J=8.4 Hz), 8.92 (brs, 1H)

(B) 4-{2-[5-(3-Fluoro-4,7-dimethylbenzofuran-2-yl)pyrrolyl]}benzoic Acid

The title compound was obtained by the same procedure as the one of Synthesis Example 1 (D).

$^1$H-NMR (DMSO-d$_6$, 400 MHz) δ; 2.45 (s, 3H), 2.53 (s, 3H), 6.63–6.66 (m, 1H), 6.89–6.92 (m, 1H), 6.98 (d, 1H, J=7.2 Hz), 7.06 (d, 1H, J=7.2 Hz), 7.93 (s, 4H), 11.87 (s, 1H), 12.83 (brs, 1H)

Synthesis Example 151
4-{2-[5-(3-Bromo-4,7-dimethylbenzofuran-2-yl)pyrrolyl]}benzoic Acid (A) Methyl 4-{2-[5-(3-bromo-4,7-dimethylbenzofuran-2-yl)pyrrolyl]}benzoate The title compound was obtained by the same procedure as the one employed for synthesizing the 3-chloro compound by using N-bromosuccinimide as a substitute for the N-chlorosuccinimide.

$^1$H-NMR (CDCl$_3$, 400 MHz) δ; 2.50 (s, 3H), 2.73 (s, 3H), 3.93 (s, 3H), 6.77–6.80 (m, 1H), 6.91 (d, 1H, J=7 .6 Hz), 6.98 (d, 1H, J=7 .6 Hz), 7.11–7.14 (M, 1H), 7.63 (d, 2H, J=8.4 Hz), 8.08 (d, 2H, J=8.4 Hz), 9.38 (brs, 1H)

(B) 4-{2-[5-(3-Bromo-4,7-dimethylbenzofuran-2-yl)pyrrolyl]}benzoic Acid

The title compound was obtained by the same procedure as the one of Synthesis Example 1 (D).

$^1$H-NMR (DMSO-d$_6$, 400 MHz) δ; 2.50 (s, 3H), 2.67 (s, 3H), 6.88–6.91 (m, 1H), 6.96 (d, 1H, J=7.2 Hz), 7.03–7.07 (m, 2H), 7.92 (s, 4H), 11.86 (s, 1H), 12.83 (brs, 1H)

Synthesis Example 152
4-[2-{5-(6,7-Dichlorobenzofuran-2-yl)pyrrolyl}]benzoic Acid The title compound was obtained by the same procedure.

$^1$H-NMR (DMSO-d$_6$, 400 MHz) δ; 6.76–6.79 (m, 1H), 6.85–6.88 (m, 1H), 7.30 (s, 1H), 7.47 (d, 1H, J=8.4 Hz), 7.64 (d, 1H, J=8.4 Hz), 7.89 (d, 2H, J=8.4 Hz), 7.96 (d, 2H, J=8.4 Hz), 11.98 (s, 1H), 12.85 (brs, 1H)

Synthesis Example 153
4-[2-{5-(3-Chloro-5,7-dimethylbenzofuran-2-yl)pyrrolyl}]benzoic Acid The title compound was obtained by the same procedure as the one of Synthesis Example 1.

$^1$H-NMR (DMSO-d$_6$, 400 MHz) δ; 2.37 (s, 3H), 2.51 (s, 3H), 6.90–6.97 (m, 2H), 7.02 (brs, 1H), 7.16 (brs, 1H), 7.94 (s, 4H), 11.91 (s, 1H), 12.85 (brs, 1H)

Synthesis Example 154
4-]2-{5-(3-Chloro-7-propylbenzofuran-2-yl)pyrrolyl}]benzoic Acid The title compound was obtained by the same procedure as the one of Synthesis Example 1.

$^1$H-NMR (DMSO-d$_6$, 400 MHz) δ; 0.95 (t, 3H, J=7.6 Hz), 1.70–1.82 (m, 2H), 2.94 (t, 2H, J=7.6 Hz), 6.91–6.94 (m, 1H), 6.96–6.99 (m, 1H), 7.22 (dd, 1H, J=1.2, 7.6 Hz), 7.29 (t, 1H, J=7.6 Hz), 7.38 (dd, 1H, J=1.2, 7.6 Hz), 7.93 (s, 4H), 11.90 (s, 1H), 12.89 (brs, 1H)

Synthesis Example 155
4-[2-{5-(5-Fluoro-5,7-dimethylbenzofuran-2-yl)pyrrolyl}]benzoic Acid The title compound was obtained by the same procedure as the one of Synthesis Example 1.

$^1$H-NMR (DMSO-d$_6$, 400 MHz) δ; 2.35 (s, 3H) 2.4 6 (s, 3H), 6.61–6.64 (m, 1H), 6.85–6.88 (m, 1H), 7.00 (brs, 1H), 7.22 (brs, 1H), 7.89 (s, 4H), 11.86 (s, 1H), 12.83 (brs, 1H)

Synthesis Example 156
4-[2-{5-(5-Fluoro-3,7-dimethylbenzofuran-2-yl)pyrrolyl}]benzoic Acid The title compound was obtained by the same procedure as the one of Synthesis Example 1.

$^1$H-NMR (DMSO-d$_6$, 400 MHz) δ; 2.33 (s, 3H), 2.53 (s, 3H), 6.64–6.67 (m, 1H), 6.87–6.90 (m, 1H), 6.95 (dd, 1H, J=2.0, 10.4 Hz), 7.22 (dd, 1H, J=2.0, 10.4 Hz), 7.93 (s, 4H), 11.73 (s, 1H) 12.84 (brs, 1H)

Synthesis Example 157
4-=2-{5-(5-Fluoro-4,7-dimethylbenzofuran-2-yl)pyrrolyl}]benzoic Acid The title compound was obtained by the same procedure as the one of Synthesis Example 1.

¹H-NMR (DMSO-d₆, 400 MHz) δ; 2.34 (s, 3H), 2.46 (s, 3H), 6.71–6.74 (m, 1H), 6.83–6.86 (m, 1H), 6.90 (d, 1H, J=10.8 Hz), 7.26 (s, 1H), 7.89 (d, 2H, J=8.4 Hz), 7.95 (d, 2H, J=8.4 Hz), 11.84 (s, 1H), 12.83 (brs, 1H)

Synthesis Example 158

4-[2-{5-(5-Fluoro-3,4,7-trimethylbenzofuran-2-yl)pyrrolyl}]benzoic Acid

The title compound was obtained by the same procedure as the one of Synthesis Example 1.

¹H-NMR (DMSO-d₆, 400 MHz) δ; 2.48 (s, 6H), 2.50 (s, 3H), 6.59–6.62 (m, 1H), 6.85–6.88 (m, 1H), 6.92 (d, 1H, J=10.8 Hz), 7.92 (s, 4H), 11.72 (s, 1H), 12.80 (brs, 1H)

Synthesis Example 159

4-[2-{5-(3,5-Bromo-4,7-dimethylbenzofuran-2-yl)pyrrolyl}]benzoic Acid

The title compound was obtained by the same procedure as the one of Synthesis Example 1.

¹H-NMR (DMSO-d₆, 400 MHz) δ; 2.42 (s, 3H), 2.48 (s, 3H), 6.65–6.68 (m, 1H), 6.89–6.92 (m, 1H), 7.03 (d, 1H, J=10.8 Hz), 7.93 (s, 4H), 11.91 (s, 1H), 12.85 (brs, 1H)

Synthesis Example 160

4-[2-{5-(3-Chloro-5-fluoro-4,7-dimethylbenzofuran-2-yl)pyrrolyl}]benzoic Acid

The title compound was obtained by the same procedure as the one of Synthesis Example 1.

¹H-NMR (DMSO-d₆, 400 MHz) δ; 2.48 (s, 3H), 2.52 (s, 3H), 6.91–6.94 (m, 1H), 6.98–7.01 (m, 1H), 7.04 (d, 1H, J=10.8 Hz), 7.95 (s, 4H), 11.92 (s, 1H), 12.86 (brs, 1H)

Synthesis Example 161

4-[2-{5-(3-Bromo-4,7-dimethylbenzofuran-2-yl)pyrrolyl}]benzoic Acid

The title compound was obtained by the same procedure as the one of Synthesis Example 1.

¹H-NMR (DMSO-d₆, 400 MHz) δ; 1.38 (t, 3H, J=7.6 Hz), 2.29 (s, 3H), 34.20 (q, 2H, J=7.6 Hz), 6.69–6.72 (m, 1H), 6.77 (d, 1H, J=10.8 Hz), 6.81–6.84 (m, 1H), 7.26 (s, 1H), 7.89 (d, 2H, J=8.4 Hz), 7.94 (d, 2H, J=8.4 Hz), 11.88 (s, 1H), 12.80 (brs, 1H)

Synthesis Example 162

4-[2-{5-(7-Ethyl-5-fluoro-4-methylbenzofuran-2-yl)pyrrolyl}]benzoic Acid

The title compound was obtained by the same procedure as the one of Synthesis Example 1.

¹H-NMR (DMSO-d₆, 400 MHz) δ; 1.27 (t, 3H, J=7.6 Hz), 2.34 (s, 3H), 2.85 (q, 2H, J=7.6 Hz), 6.71–6.74 (m, 1H), 6.83–6.86 (m, 1H), 6.91 (d, 1H, J=10.8 Hz), 7.88 (d, 2H, J=8.4 Hz), 7.95 (d, 2H, J=8.4 Hz), 11.83 (s, 1H), 12.86 (brs, 1H)

Synthesis Example 163

4-[2-{5-(7-Ethyl-3,5-difluoro-4-methylbenzofuran-2-yl)pyrrolyl}]benzoic Acid

The title compound was obtained by the same procedure as the one of Synthesis Example 1.

¹H-NMR (DMSO-d₆, 400 MHz) δ; 1.28 (t, 3H, J=7.6 Hz), 2.43 (s, 3H), 2.90 (q, 2H, J=7.6 Hz), 6.65–6.68 (m, 1H), 6.86–6.89 (m, 1H), 7.04 (d, 1H, J=11.2 Hz), 7.85–7.96 (m, 4H), 11.87 (s, 1H), 12.85 (brs, 1H)

Synthesis Example 164

4-[2-{5-(7-Chloro-4-fluorobenzothiophen-2-yl)pyrrolyl}]benzoic Acid

The title compound was obtained by the same procedure as the one of Synthesis Example 1.

¹H-NMR (DMSO-d₆, 400 MHz) δ; 1.2–86.74 (m, 7H), 6.81–6.84 (m, 1H)), 7.27 (t, 1H, J=8.8 Hz), 7.42 (dd, 1H, J=4.4, 8.8 Hz), 7.90 (d, 2H, J=8.4 Hz), 7.95 (d, 2H, J=8.4 Hz), 11.40 (s, 1H), 12.81 (brs, 1H)

Synthesis Example 165

4-[2-{5-(7-Chloro-4-fluorobenzothiophen-2-yl)pyrrolyl}]benzoic Acid

The title compound was obtained by the same procedure as the one of Synthesis Example 1.

¹H-NMR (DMSO-d₆, 400 MHz) δ; 2.52 (s, 3H), 6.87–6.94 (m, 2H), 7.38 (brs, 2H), 7.61 (brs, 1H)77.9 0 (s, 4H), 11.81 (s, 1H), 12.85 (brs, 1H)

Synthesis Example 166

4-[2-{5-(7-Chloro-4-fluorobenzothiophen-2-yl)pyrrolyl}]benzoic Acid

The title compound was obtained by the same procedure as the one of Synthesis Example 1.

¹H-NMR (DMSO-d₆, 400 MHz) δ; 2.53 (s, 3H), 6.88–6.94 (m, 4H), 7.24 (dd, 1H, J=2.4, 9.6 Hz), 7.40 (dd, 1H, J=2.4, 9.6 Hz), 7.93 (s, 4H), 11.80 (s, 1H), 12.87 (brs, 1H)

Synthesis Example 167

4-[2-{5-(7-Fluoro-4-trifluoromethylbenzofuran-2-yl)pyrrolyl}]benzoic Acid

The title compound was obtained by the same procedure as the one of Synthesis Example 27.

¹H-NMR (DMSO-d₆, 400 MHz) δ;6.87–6.92 (m, 2H), 7.35 (dd, 1H, J=10.0, 10.4 Hz), 7.53 (brs, 1H), 7.62 (dd, 1H, J=3.6, 8.8 Hz), 7.93 (d, 2H, J=8.8 Hz), 7.96 (d, 2H, J=8.8 Hz)

Synthesis Example 168

4-[2-{5-(5-Fluoro-3,7-dimethylbenzofuran-2-yl)pyrrolyl}]benzoic Acid

The title compound was obtained by the same procedure as the one of Synthesis Example 1.

¹H-NMR (DMSO-d₆, 400 MHz) δ; 2.57 (s, 3H), 6.91–6.94 (m, 1H), 6.96–7.02 (m, 1H), 7.09 (dd, 1H, J=2.7, 11.0 Hz), 7.17 (dd, 1H, J=2.3, 8.0 Hz), 7.95 (brs, 4H), 12.0 (s, 1H)

Synthesis Example 169

4-[2-{5-(3-Chloro-7-ethyl-5-fluorobenzofuran-2-yl)pyrrolyl}]benzoic Acid

The title compound was obtained by the same procedure as the one of Synthesis Example 1.

¹H-NMR (DMSO-d₆, 400 MHz) δ; 1.30 (t, 3H, J=8.0 Hz), 3.00 (q, 2H, J=7.2 Hz), 6.90–6.93 (m, 1H), 6.98–7.00 (m, 1H), 7.12 (dd, 1H, J=2.9, 10.4 Hz), 7.18 (dd, 1H, J=2.4, 8.8 Hz), 7.93 (d, 2H, J=8.0 Hz), 7.96 (d, 2H, J=8.0 Hz), 11.96 (brs, 1H)

Synthesis Example 170

4-[2-{5-(3-Chloro-5-fluoro-7-propylbenzofuran-2-yl)pyrrolyl}]benzoic Acid

The title compound was obtained by the same procedure as the one of Synthesis Example 1.

¹H-NMR (DMSO-d₆, 400 MHz) δ; 0.96 (t, 3H, J=6.8 Hz), 1.72–1.80 (m, 2H), 2.96 (t, 2H, J=7.2 Hz), 6.90–6.93 (m, 1H), 6.98–7.01 (m, 1H), 7.10 (dd, 1H, J=2.0, 10.4 Hz), 7.18 (dd, 1H, J=2.0, 7.6 Hz), 7.92 (d, 2H, J=8.4 Hz), 7.96 (d, 2H, J=8.4 Hz), 11.88 (brs, 1H)

Synthesis Example 171

4-[2-{5-(3-Chloro-5-fluoro-7-propylbenzofuran-2-yl)-3-chloropyrrolyl}]benzoic Acid The title compound was obtained by the same procedure as the one of Synthesis Example 1.
$^1$H-NMR (DMSO-d$_6$, 400 MHz) δ; 0.94 (t, 3H, J=7.0 Hz), 1.73–1.80 (m, 2H), 2.90–2.98 (m, 2H), 7.01 (d, 1H, J=2.8 Hz), 7.13 (dd, 1H, J=2.6, 10.4 Hz), 7.22 (dd, 1H, J=2.4, 8.0 Hz), 7.88 (d, 2H, J=8.4 Hz), 8.05 (d, 2H, J=8.4 Hz)

Synthesis Example 172
4-[2-{5-(3-Bromo-5-fluoro-7-methylbenzofuran-2-yl)pyrrolyl}]benzoic Acid The title compound was obtained by the same procedure as the one of Synthesis Example 27.
$^1$H-NMR (DMSO-d$_6$, 400 MHz) δ; 2.58 (s, 3H), 6.92–6.94 (m, 1H), 7.06–7.16 (m, 3H), 7.95 (brs, 4H), 12.00 (s, 1H)

Synthesis Example 173
4-[2-{5-(7-Ethyl-5-fluoro-3-methylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 1.31 (t, 3H, J=7.6 Hz), 2.33 (s, 3H), 2.97 (q, 2H, J=7.6 Hz), 6.64–6.66 (m, 1H), 6.86–6.89 (m, 1H), 6.97 (dd, 1H, J=2.4, 10.0 Hz), 7.22 (dd, 1H, J=2.4, 8.8 Hz), 7.91 (d, 2H, J=8.4 Hz), 7.93 (d, 2H, J=8.4 Hz), 11.73 (s, 1H), 12.82 (brs, 1H)

Synthesis Example 174
4-[2-{5-(3,5-Difluoro-7-ethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 1.32 (t, 3H, J=7.6 Hz), 2.96 (q, 2H, J=7.6 Hz), 6.68–6.71 (m, 1H), 6.91 (dd, 1H, J=2.4, 3.6 Hz), 7.10 (dd, 1H, J=2.4, 10.4 Hz), 7.30 (dd, 1H, J=2.4, 8.0 Hz), 7.94 (brs, 4H), 11.95 (s, 1H), 12.86 (brs, 1H)

Synthesis Example 175
4-[2-{5-(4-Ethyl-5-fluoro-7-methylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 1.23 (t, 3H, J=7.6 Hz), 2.46 (s, 3H), 2.79 (q, 4H, J=7.6 Hz), 6.72–6.75 (m, 1H), 6.84–6.86 (m, 1H), 6.90 (d, 1H, J=10.8 Hz), 7.30 (s, 1H), 7.89 (d, 2H, J=8.4 Hz), 7.95 (d, 2H, J=8.4 Hz), 11.84 (brs, 1H)

Synthesis Example 176
4-[2-{5-(4,7-Diethyl-3,5-difluorobenzofuran-2-yl)pyrrolyl}]benzoic Acid The title compound was obtained by the same procedure as the one of Synthesis Example 1.
$^1$H-NMR (DMSO-d$_6$, 400 MHz) δ ; 1.23 (t, 3H, J=7.2 Hz), 1.30 (t, 3H, J=7.2 Hz), 2.82–2.88 (m, 2H), 2.92 (q, 2H, J=7.2 Hz), 6.67–6.70 (m, 1H), 6.90–6.92 (m, 1H), 7.05 (d, 1H, J=11.2 Hz), 7.94 (s, 4H), 11.90 (brs, 1H)

Synthesis Example 177
4-[2-{5-(3-Bromo-4,7-diethyl-5-fluorobenzofuran-2-yl)pyrrolyl}]benzoic Acid The title compound was obtained by the same procedure as the one of Synthesis Example 1.
$^1$H-NMR (DMSO-d$_6$, 400 MHz) δ; 1.22 (t, 3H, J=7.6 Hz), 1.30 (t, 3H, J=7.6 Hz), 2.97 (q, 2H, J=7.6 Hz), 3.03–3.10 (m, 2H), 6.90–6.92 (m, 1H), 7.07 (d, 1H, J=11.2 Hz), 7.09–7.12 (m, 1H), 7.93 (d, 2H, J=8.4 Hz), 7.96 (d, 2H, J=8.4 Hz), 11.90 (brs, 1H)

Synthesis Example 178
4-[2-{5-(3,5-Dichloro-7-methylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 2.58 (s, 3H), 6.92–6.95 (m, 1H), 7.00–7.02 (m, 1H), 7.27–7.29 (m, 1H), 7.40–7.42 (m, 1H), 7.96 (s, 4H), 12.00 (s, 1H)

Synthesis Example 179
4-[2-{5-(3,5-Dichloro-7-ethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 1.33 (t, 3H, J=7.7 Hz) 3.00 (q, 2H, J=7.7 Hz), 6.94 (dd, 1H, J=2.8, 4.0 Hz), 7.01 (dd, 1H, J=2.0, 3.6 Hz), 7.29 (d, 1H, J=2.0 Hz), 7.42 (d, 1H, J=1.6 Hz), 7.96 (s, 4H), 11.99 (brs, 1H)

Synthesis Example 180
4-[2-{5-(3-Fluoro-4,5,7-trimethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 2.26 (s, 3H), 2.43 (s, 3H), 2.45 (s, 3H), 6.61–6.65 (m, 1H), 6.88–6.90 (m, 1H), 6.97–7.00 (m, 1H), 7.93 (s, 4H), 11.84 (brs, 1H)

Synthesis Example 181
4-[2-{5-(3-Chloro-4,5,7-trimethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 2.27 (s, 3H), 2.50 (s, 3H), 2.57 (s, 3H), 6.89–6.92 (m, 1H), 6.94–6.97 (m, 1H), 6.98–7.00 (m, 1H), 7.94 (s, 4H), 11.85 (brs, 1H)

Synthesis Example 182
4-[2-{5-(3-Bromo-4,5,7-trimethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 2.27 (s, 3H), 2.50 (s, 3H), 2.61 (s, 3H), 6.88–6.91 (m, 1H), 6.98–7.00 (m, 1H), 7.04–7.07 (m, 1H), 7.94 (s, 4H), 11.85 (brs, 1H)

Synthesis Example 183
4-[2-{5-(5-Fluoro-4-methylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 2.40 (s, 3H), 6.72–6.75 (m, 1H), 6.83–6.86 (m, 1H), 7.04 (dd, 1H, J=9.2, 9.6 Hz), 7.29 (s, 1H), 7.39 (dd, 1H, J=3.6, 8.4 Hz), 7.90 (d, 2H, J=8.4 Hz), 7.95 (d, 2H, J=8.4 Hz), 11.93 (brs, 1H)

Synthesis Example 184
4-[2-{5-(5-Chloro-4,7-dimethylbenzofuran-2-yl)pyrrolyl}]benzoic Acid The title compound was obtained by the same procedure as the one of Synthesis Example 1.
$^1$H-NMR (DMSO-d$_6$, 400 MHz) δ; 3.24 (s, 3H) 3.39 (s, 3H) 6.73–6.75 (m, 1H), 6.84–6.86 (m, 1H), 7.12 (s, 1H), 7.27 (s, 1H), 7.88–7.90 (d, 2H, J=8.8 Hz), 7.94–7.96 (d, 2H, J=8.8 Hz), 11.59 (brs, 1H)

Synthesis Example 185
4-[2-{5-(5-Chloro-3-fluoro-4,7-dimethylbenzofuran-2-yl)pyrrolyl}]benzoic Acid The title compound was obtained by the same procedure as the one of Synthesis Example 1.

¹H-NMR (DMSO-d₆, 400 MHz) δ; 2.49 (s, 3H), 2.54 (s, 3H), 6.68–6.69 (m, 1H), 6.91–6.92 (m, 1H), 7.26 (s, 1H), 7.94 (s, 4H), 11.59 (brs, 1H)

Synthesis Example 186

4-[2-{5-(3-Bromo-5-chloro-4,7-methylbenzofuran-2-yl)pyrrolyl}]benzoic Acid

The title compound was obtained by the same procedure as the one of Synthesis Example 1.

¹H-NMR (DMSO-d₆, 400 MHz) δ; 2.53 (s, 3H), 2.73 (s, 3H), 6.91–6.92 (m, 1H), 7.10–7.11 (m, 1H), 7.27 (s, 1H), 7.95 (s, 4H), 11.59 (brs, 1H)

Synthesis Example 187

4-[2-{5-(5-Bromo-3,4,7-trimethylbenzofuran-2-yl)pyrrolyl}]benzoic Acid.

The title compound was obtained by the same procedure as the one of Synthesis Example 1.

¹H-NMR (DMSO-d₆, 400 MHz) δ; 2.52 (s, 3H), 2.62 (s, 3H), 3.29 (s, 3H), 6.61–6.62 (m, 1H), 6.86–6.88 (m, 1H), 7.15 (s, 1H), 7.89–7.91 (d, 2H, J=8.8 Hz), 7.92–7.94 (d, 2H, J=8.8 Hz), 11.56 (brs, 1H)

Synthesis Example 188

4-[2-{5-(5-Bromo-4-methylbenzofuran-2-yl)pyrrolyl}]benzoic Acid

The title compound was obtained by the same procedure as the one of Synthesis Example 1.

¹H-NMR (DMSO-d₆, 400 MHz) δ; 2.48 (s, 3H), 6.75–6.76 (m, 1H, 6.84–6.86 (m, 1H), 7.12 (d, 1H, J=1.2 Hz), 7.17 (s, 1H), 7.54 (d, 1H, J=1.6 Hz), 7.88–7.96 (m, 4H), 11.90 (s, 1H), 12.80 (brs, 1H)

Synthesis Example 189

4-[2-{5-(3-Bromo-5-fluoro-7-methylbenzofuran-2-yl)pyrrolyl}]benzoic Acid

The title compound was obtained by the same procedure as the one of Synthesis Example 1.

¹H-NMR (DMSO-d₆, 400 MHz) δ; 0.94 (t, 3H, J=7.2 Hz), 1.66 (q, 2H, J=7.2 Hz), 2.78 (t, 2H, J=7.2 Hz), 6.74–6.77 (m, 1H), 6.82–6.85 (m, 1H), 7.29 (d, 1H, J=10.0 Hz), 7.41 (s, 1H), 7.87 (d, 2H, J=8.4 Hz), 7.95 (d, 2H, J=8.4 Hz), 11.91 (brs, 1H)

Synthesis Example 190

4-[2-{5-(3-Fluoro-6-methylbenzofuran-2-yl)pyrrolyl}]benzoic Acid

The title compound was obtained by the same procedure as the one of Synthesis Example 1.

¹H-NMR (DMSO-d₆, 400 MHz) δ; 2.31 (s, 3H), 6.68–6.72 (m, 1H), 6.82–6.85 (m, 1H), 7.15 (s, 1H), 7.40 (d, 1H, J=10.0 Hz), 7.47 (d, 1H, J=6.4 Hz), 7.88 (d, 2H, J=8.4 Hz), 7.94 (d, 2H, J=8.4 Hz), 11.90 (brs, 1H)

Synthesis Example 191

4-[2-{5-(5,7-Difluorobenzofuran-2-yl)pyrrolyl}]benzoic Acid

The title compound was obtained by the same procedure as the one of Synthesis Example 1.

¹H-NMR (DMSO-d₆, 400 MHz) δ; 6.78–6.81 (m, 1H), 6.85–6.88 (m, 1H), 7.18–7.25 (m, 1H), 7.29 (d, 1H, J=3.2 Hz), 7.37 (dd, 1H, J=2.4, 8.4 Hz), 7.89 (d, 2H, J=8.4 Hz), 7.95 (d, 2H, J=8.8 Hz), 12.02 (brs, 1H)

Synthesis Example 192

4-[2-{5-(4-Ethyl-5-fluorobenzofuran-2-yl)pyrrolyl}]benzoic Acid

The title compound was obtained by the same procedure as the one of Synthesis Example 1.

¹H-NMR (DMSO-d₆, 400 MHz) δ; 1.25 (t, 3H, J=7.6 Hz), 2.80–2.88 (m, 2H), 6.72–6.75 (m, 1H), 6.83–6.86 (m, 1H), 7.00–7.06 (m, 1H), 7.33 (s, 1H), 7.38–7.42 (m, 1H), 7.89 (d, 2H, J=8.8 Hz), 7.95 (d, 2H, J=8.8 Hz), 11.91 (brs, 1H)

Synthesis Example 193

4-[2-{5-(5-Chloro-7-ethyl-3-fluorobenzofuran-2-yl)pyrrolyl}]benzoic Acid

The title compound was obtained by the same procedure as the one of Synthesis Example 1.

¹H-NMR (DMSO-d₆, 400 MHz) δ; 1.32 (t, 3H, J=7.6 Hz), 2.69 (q, 2H, J=7.6 Hz), 6.69–6.72 (m, 1H), 6.90–6.93 (m, 1H), 7.26–7.28 (m, 1H), 7.54–7.57 (m, 1H), 7.90–7.96 (m, 4H), 11.95 (brs, 1H)

Synthesis Example 194

4-[2-{5-(5-Chloro-7-methylmethylenedioxymethylbenzofuran-2-yl)pyrrolyl}]benzoic Acid The title compound was obtained by the same procedure as the one of Synthesis Example 1.

¹H-NMR (DMSO-d₆, 400 MHz) (;3.36 (s, 3H), 4.74 (s, 2H), 4.85 (s, 2H), 6.74–6.75 (m, 1H), 6.85–6.87 (m, 1H), 7.22 (s, 1H), 7.25 (d, 1H, J=2 Hz), 7.69 (d, 1H, J=2 Hz), 7.88 (d, 2H, J=8.4 Hz), 7.95 (d, 2H, J=8.4 Hz), 11.93 (brs, 1H)

Synthesis Example 195

4-[2-{5-(5-Chloro-7-nitrobenzofuran-2-yl)pyrrolyl}]benzoic Acid

The title compound was obtained by the same procedure as the one of Synthesis Example 1.

¹H-NMR (DMSO-d₆, 400 MHz) δ; 6.87–6.88 (m, 1H), 6.92–6.93 (m, 1H), 7.26 (s, 1H), 7.64 (s, 1H), 7.89 (d, 2H, J=8.4 Hz), 7.92 (s, 1H), 8.00 (d, 2H, J=8.4 Hz), 12.09 (brs, 1H)

Synthesis Example 196

4-[2-{5-(7-Chloro-4-ethyl-5-fluorobenzofuran-2-yl)pyrrolyl}]benzoic Acid

The title compound was obtained by the same procedure as the one of Synthesis Example 1.

¹H-NMR (DMSO-d₆, 400 MHz) δ; 1.22 (t, 3H, J=7.2 Hz), 2.81 (q, 2H, J=7.2 Hz), 6.76–6.79 (m, 1H), 6.86–6.89 (m, 1H), 7.30 (d, 1H, J=10.0 Hz), 7.42 (s, 1H), 7.90 (d, 2H, J=8.4 Hz), 7.96 (d, 2H, J=8.4 Hz), 11.96 (s, 1H), 12.84 (brs, 1H)

What is claimed is:

1. A method for preventing, inhibiting or treating graft-versus-host disease or graft rejection reactions in organ transplantation by administering an efficacious amount of a retinoic acid receptor (RAR) agonist to a patient in need thereof.

2. The method as claimed in claim 1, wherein the retinoic acid receptor (RAR) agonist is a retinoic acid receptor subtype α (RARα) agonist.

3. A method for preventing, inhibiting or treating graft-versus-host disease or graft rejection reactions in organ transplantation in a patient in need thereof comprising administering an efficacious amount of a retinoic acid receptor (RAR) agonist selected from the group consisting of:

(1) a fused-ring carboxylic acid derivative of the formula (I):

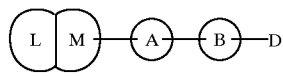

wherein rings L and M, which have been fused, are the same as or different from each other and represent an optionally substituted aromatic hydrocarbon ring or an optionally substituted heterocycle; rings A and B independently each represent an optionally substituted aromatic hydrocarbon ring or a heterocycle; and D represents optionally protected carboxy;

(2) a heterocyclic carboxylic acid derivative of the formula (II):

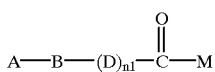

wherein A is a group of the formula:

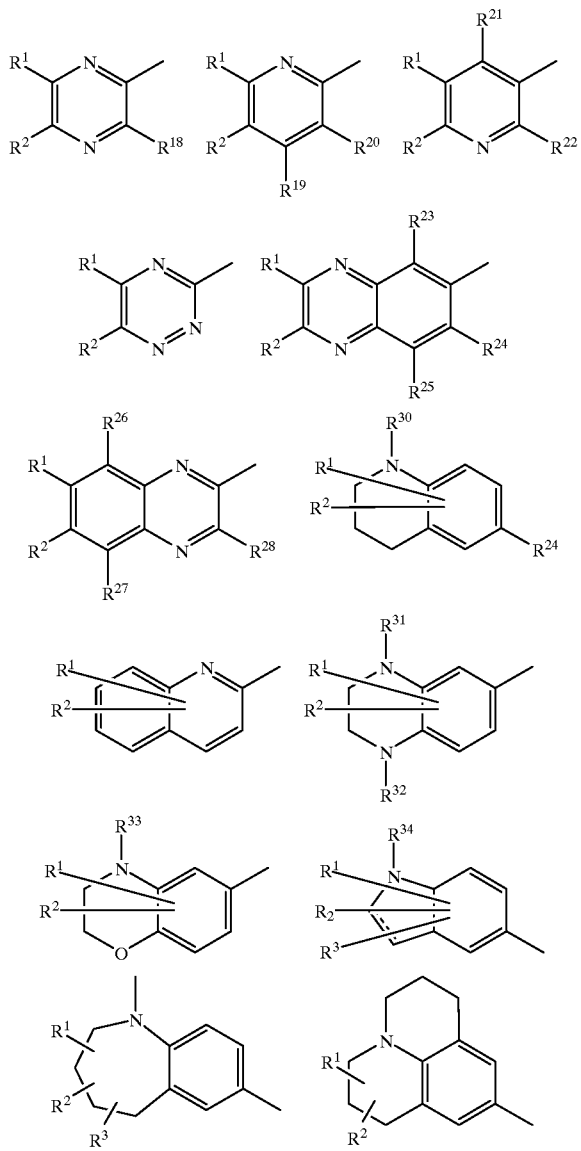

-continued

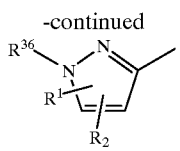

wherein $R^1$ to $R^3$, $R^{18}$ to $R^{28}$ and $R^{30}$ to $R^{36}$ are the same as or different from each other and represent hydrogen, halogeno, lower alkyl or optionally substituted phenyl; and ==== represents either a single bond or a double bond;

B represents optionally substituted heteroarylene, optionally substituted arylene, a group represented by the formula —COHN— or a group represented by the formula —$CR^6$=$CR^7$— where $R^6$ and $R^7$ are the same as or different from each other and represent hydrogen, lower alkyl or halogeno;

D represents optionally substituted arylene, optionally substituted heteroarylene or a group represented by the formula —$CR^6$=$CR^7$— wherein $R^6$ and $R^7$ are each as defined above;

$n_1$ represents 0 or 1; and

M represents hydroxy, lower alkoxy or a group represented by the formula —$NR^{16}R^{17}$ where $R^{16}$ and $R^{17}$ are the same as or different from each other and represent hydrogen, hydroxy, lower alkyl, hydroxyalkyl, aryl or heteroaryl, or $R^{16}$ and $R^{17}$ may form a ring with the nitrogen atom to which they are bonded, and the ring may optionally contain oxygen or sulfur;

(3) 4-[(5,6,7,8-tetrahydro-5,5,8,8-tetramethylnaphthalen-2-yl)pyrrolyl]benzoic acid, 4-[(5,6,7,8-tetrahydro-5,5,8,8-tetramethylnaphthanlen-2-yl)furanyl]benzoic acid, 4-[(5,6,7,8-tetrahydro-5,5,8,8-tetramethylnaphthalen-2-yl)thiophenyl]benzoic acid or 4-[(5,6,7,8-tetrahydro-5,5,8,8-tetramethylnaphthalen-2-yl)pyrazolyl]benzoic acid;

(4) a 3,4-dihydro-2H-1-benzopyranylpropenylbenzoic acid derivative, 3,4,-dihydro-2H-1-benzothiopyranylpropenylbenzoic acid derivative, 1,2,3,4-tetrahydroquinolinylpropenylbenzoic acid derivative, (3,4-dihydro-2H-1-benzopyrancarboxamido)benzoic acid derivative, (3,4-dihydro-2H-1-benzothiopyrancarboxamido)benzoic acid derivative or (1,2,3,4-tetrahydroquinolinecarboxamido)benzoic acid derivative;

(5) a 3,4-dihydro-2H-1-benzopyranylacetylene derivative, 3,4-dihydro-2H-1-benzothiopyranylacetylene derivative or 1,2,3,4-tetrahydroquinolinylacetylene derivative;

(6) a tetrahydronaphthylpropenylphenol derivative;

(7) a phenylpolyene derivative; and (8) all-trans-retinoic acid.

4. The method as claimed in claim 3, wherein a retinoic acid receptor (RAR) agonist selected from the group consisting of the following ones is used as the active ingredient:

1) fused-ring carboxylic acid derivatives represented by the following formula (I):

wherein

represents naphthyl, benzofuranyl or benzothiophenyl substituted by lower alkyl, halogeno, halo (lower alkyl) or a combination thereof; A represents pyrrole; B represents benzene; and D represents optionally protected carboxy; and 2) heterocyclic carboxylic acid derivatives represented by the following formula (II):

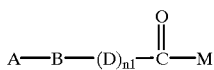

wherein B represents pyrrolylene or pyrazolylene; $n_1$ represents 1; and A, D and M are each as defined above.

5. The method as claimed in claim 3, wherein a retinoic acid receptor (RAR) agonist selected from the group consisting of the following ones is used as the active ingredient:

1) 4-{2-[5-(5,8-dimethylnaphthalen-2-yl)pyrrolyl]} benzoic acid;
2) 4-{2-[5-(8-methylnaphthalen-2-yl)pyrrolyl]}benzoic acid;
3) 4-{2-[5-(8-ethylnaphthalen-2-yl)pyrrolyl]}benzoic acid;
4) 4-{2-[5-(8-isopropylnaphthalen-2-yl)pyrrolyl]}-benzoic acid;
5) 4-{2-[5-(8-naphthalen-2-yl)pyrrolyl]}benzoic acid;
6) 4-{2-[5-(8-phenylnaphthalen-2-yl)pyrrolyl]}benzoic acid;
7) 4-{2-[5-(4,7-dimethylbenzofuran-2-yl)pyrrolyl]} benzoic acid;
8) 4-{2-[5-(4,7-dichlorobenzofuran-2-yl)pyrrolyl]} benzoic acid;
9) 4-{2-[5-(5-chloro-7-ethylbenzofuran-2-yl)pyrrolyl]} benzoic acid;
10) 4-{2-[5-(4,7-dimethylbenzothiophen-2-yl))pyrrolyl]} benzoic acid;
11) 4-{2-{5-[2-(5,6,7,8-tetrahydro-5,5,8,8-tetramethylquinoxalyl)pyrrolyl]}benzoic acid;
12) 4-{2-{5-[3-(1-tert-butyl-5-isopropylpyrazolyl)pyrrolyl]}benzoic acid;
13) 4-{4-{2-[2-(5,6,7,8-tetrahydro-5,5,8,8-tetramethylquinoxalyl)furyl]}benzoic acid;
14) 4-{2-{5-[2-5,6-diisopropylpyrazinyl]}pyrrolyl}benzoic acid;
15) 4-{2-{5-[2-(5,5,7,7-tetramethylcyclopenta[b]pyrazinyl)]pyrrolyl}}-benzoic acid;
16) 4-{2-{5-[7-(1,5,5-trimethyl-2,3,4,5-tetrahydro-1H-benzazepinyl)]pyrrolyl}benzoic acid;
17) 4-{2-[5-(5,6,7,8-tetrahydro-5,5,8,8-tetramethylnaphthalen-2-yl)pyrrolyl}benzoic acid;
18) 9-(4-methoxy-2,3,6-trimethylphenyl)-7,8-dimethyl-nona-2,4,6,8-tetraen-1-oic acid;
19) 4-[(E)-2-(5,6,7,8-tetrahydro-5,5,8,8-tetramethylnaphthalen-2-yl)propenyl]benzoic acid;
20) 4-{2-[5-(3-fluoro-4,7-dimethylbenzofuran-2-yl)pyrroyl]}benzoic acid:
21) 4-{2-[5-(7-ethyl-4-methylbenzofuran-2-yl)pyrrolyl]} benzoic acid;
22) 4-{2-[5-(7-fluoro-4-trifluoromethylbenzofuran-2-yl)pyrroyl]}benzoic acid;
23) 6-[2-(4,4-dimethylthiochroman-6-yl)ethynyl] nicotinic acid; and
24) all-trans-retinoic acid.

6. The method as claimed in claim 3, wherein a retinoic acid receptor (RAR) agonist selected from the group consisting of the following ones is used as the active ingredient:

1) 4-{2-[5-(5,8-dimethylnaphthalen-2-yl)pyrrolyl]} benzoic acid;
2) 4-{2-[5-(8-methylnaphthalen-2-yl)pyrrolyl]}benzoic acid;
3) 4-{2-[5-(8-ethylnaphthalen-2-yl)pyrrolyl]}benzoic acid;
4) 4-{2-[5-(8-isopropylnaphthalen-2-yl)pyrrolyl]}-benzoic acid;
5) 4-{2-[5-(8-naphthalen-2-yl)pyrrolyl]}benzoic acid;
6) 4-{2-[5-(8-phenylnaphthalen-2-yl)pyrrolyl]}benzoic acid;
7) 4-{2-[5-(4,7-dimethylbenzofuran-2-yl)pyrrolyl]} benzoic acid;
8) 4-(2-[5-(4,7-dichlorobenzofuran-2-yl)pyrrolyl]} benzoic acid;
9) 4-{2-[5-(5-chloro-7-ethylbenzofuran-2-yl)pyrrolyl]} benzoic acid;
10) 4-{2-[5-(4,7-dimethylbenzothiophen-2-yl))pyrrolyl]} benzoic acid;
11) 4-{2-[5-(3-fluoro-4,7-dimethylbenzofuran-2-yl)pyrrolyl]}benzoic acid;
12) 4-{2-[5-(7-ethyl-4-methylbenzofuran-2-yl)pyrrolyl]} benzoic acid; and
13) 4-{2-[5-(7-fluoro-4-trifluoromethylbenzofuran-2-yl)pyrrolyl]}benzoic acid.

7. The method as claimed in claim 3, wherein a retinoic acid receptor (RAR) agonist selected from the group consisting of the following ones is used as the active ingredient:

1) 4-{2-[5-(4,7-dimethylbenzofuran-2-yl)pyrrolyl]} benzoic acid;
2) 4-{2-[5-(5-chloro-7-ethylbenzofuran-2-yl))pyrrolyl]} benzoic acid;
3) 4-{2-[5-(4,7-dimethylbenzothiophen-2-yl)pyrrolyl]} benzoic acid;
4) 4-{2-[5-(3-fluoro-4,7-dimethylbenzofuran-2-yl)pyrrolyl]}benzoic acid;
5) 4-{2-[5-(7-ethyl-4-methylbenzofuran-2-yl)pyrrolyl]} benzoic acid, and
6) 4-{2-[5-(7-fluoro-4-trifluoromethylbenzofuran-2-yl)pyrrolyl]}benzoic acid.

* * * * *